US011884726B2

(12) United States Patent
Cataldi et al.

(10) Patent No.: US 11,884,726 B2
(45) Date of Patent: *Jan. 30, 2024

(54) DOSAGE REGIMEN FOR MADCAM ANTAGONISTS

(71) Applicant: PFIZER INC., New York, NY (US)

(72) Inventors: Fabio Cataldi, Beverly, MA (US); Robert A. Clare, Wayne, PA (US); Gail M. Comer, Phoenixville, PA (US); Vivekananda Pradhan, Acton, MA (US); Alaa Ahmad, Arlington, MA (US); Mina Hassan-Zahraee, Cambridge, MA (US); Mera Krishnan Tilley, Medford, MA (US); Weidong Zhang, Acton, MA (US); Anindita Banerjee, Canton, MA (US); Karen Michelle Page, Merrimack, NH (US); Michael Steven Vincent, Newton, MA (US); David J. Von Schack, Arlington, MA (US)

(73) Assignee: Pfizer Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 17/107,228

(22) Filed: Nov. 30, 2020

(65) Prior Publication Data

US 2021/0324070 A1    Oct. 21, 2021

Related U.S. Application Data

(62) Division of application No. 15/542,110, filed as application No. PCT/IB2016/050047 on Jan. 6, 2016, now Pat. No. 10,851,163.

(60) Provisional application No. 62/101,877, filed on Jan. 9, 2015, provisional application No. 62/263,910, filed on Dec. 7, 2015, provisional application No. 62/263,197, filed on Dec. 4, 2015.

(51) Int. Cl.
| | |
|---|---|
| *A61K 39/00* | (2006.01) |
| *A61K 39/395* | (2006.01) |
| *C07K 16/28* | (2006.01) |
| *A61P 29/00* | (2006.01) |
| *A61P 1/04* | (2006.01) |
| *C12Q 1/6883* | (2018.01) |
| *G01N 33/68* | (2006.01) |

(52) U.S. Cl.
CPC .... *C07K 16/2803* (2013.01); *A61K 39/39541* (2013.01); *A61P 1/04* (2018.01); *A61P 29/00* (2018.01); *C12Q 1/6883* (2013.01); *G01N 33/6893* (2013.01); *A61K 2039/505* (2013.01); *A61K 2039/545* (2013.01); *C07K 2317/565* (2013.01); *C12Q 2600/156* (2013.01); *C12Q 2600/158* (2013.01); *G01N 2800/065* (2013.01); *G01N 2800/7095* (2013.01)

(58) Field of Classification Search
None
See application file for complete search history.

(56) References Cited

U.S. PATENT DOCUMENTS

| 5,698,679 A | 12/1997 | Nemazee |
|---|---|---|
| 6,551,593 B1 | 4/2003 | Ringler et al. |
| 10,851,163 B2* | 12/2020 | Cataldi ............ A61K 39/39541 |
| 2002/0147314 A1 | 10/2002 | Briskin et al. |
| 2002/0172679 A1 | 11/2002 | Ringler et al. |
| 2004/0243058 A1 | 12/2004 | Barbut et al. |
| 2009/0238820 A1 | 9/2009 | Allan et al. |
| 2011/0027262 A1 | 2/2011 | Das |

FOREIGN PATENT DOCUMENTS

| EP | 2177537 A2 | 9/2012 |
|---|---|---|
| JP | 6779621 B2 | 11/2020 |
| WO | WO2004/081049 A1 | 9/2004 |
| WO | WO2005/067620 A3 | 7/2005 |
| WO | WO2006/096490 A2 | 9/2006 |
| WO | WO2007/007145 A2 | 1/2007 |
| WO | WO2007/007151 A2 | 1/2007 |
| WO | WO2007/007152 A2 | 1/2007 |
| WO | WO2007/007159 A2 | 1/2007 |
| WO | WO2007/007160 A2 | 1/2007 |
| WO | WO2007007173 A2 | 1/2008 |
| WO | WO2014/160753 A1 | 10/2014 |

OTHER PUBLICATIONS

PDB, 4HCR Crystal structure of human MAdCAM-1 D1D2 complexed with Fab PF-547659. Jan. 23, 2013. (Year: 2013).*
Clinical Trial Study NCT01771809, A Multicenter Open-Label Extension Study to Assess Long-Term Safety of PF-00547659 in Subjects With Ulcerative Colitis (Turandot II). pp. 1-12, Dec. 2013. (Year: 2013).
Clinical Trial Study NCT01298492, A Multicenter Open-Label Extension Study to Assess Long-Term Safety of Pf-00547659 in Subjects With Crohn's Disease (Opera II). pp. 1-15, Nov. 2013 (Year: 2013).
Desai et al., "Review article: biological activity markers in inflammatory bowel disease", Alimentary Pharmacology & Therapeutics., 25(3): 247-2553 (Nov. 3, 2006).
EU Clinical Trials Register. EudraCT No. 2012-002030-37. A Double-Blind, Randomized, Placebo-Controlled, Parallel, Dose-Ranging Study to Evaluate the Efficacy and Safety of PF-00547659 in Patients With Moderate to Severe Ulcerative Colitis (Turandot). May 29, 2013, pp. 1-6. (Year: 2013).
Faubion et al., "Emerging Biomarkers in Inflammatory Bowel Disease (EMBARK) Study Identifies Fecal Calprotectin, Serum MMP9, and Serum IL-22 as a Novel Combination of Biomarkers for Crohn's Disease Activity: Role of Cross-Sectional Imaging", American Journal of Gastroenterology, 108(12): 1891-19001 (Dec. 15, 2013).

(Continued)

*Primary Examiner* — Maher M Haddad
(74) *Attorney, Agent, or Firm* — Proskauer Rose LLP

(57) ABSTRACT

The present invention provides a method for the treatment of a patient comprising administering to the patient an initial dose of between about 1 mg and about 150 mg of a MAdCAM antagonist antibody. Biomarkers for assessing a patient's response to anti-MAdCAM treatment are also provided.

10 Claims, 21 Drawing Sheets

Specification includes a Sequence Listing.

(56) References Cited

OTHER PUBLICATIONS

Leal et al., "Adhesion Molecules as a Therapeutic Target in IBD", EMJ Gastroenterol., vol. 1, pp. 62-73 (Dec. 1, 2013).

Martin et al. Mechanistic Population Pharmacokinetics (PK) Model of PF-00547659, a Fully Human IgG2 Anti-MAdCAM Antibody, in Ulcerative Colitis Patients: Results of a First in Human (Fih) Study. Abstract W1042. Gastroenterology, Jun. 2009, vol. 136(5), Suppl. 1, A641 (Year: 2009).

Protein Data Bank (PDB). Remediated Sequence—4HCR: Crystal structure of human MAdCAM-1 D1D2 complexed with Fab PF-547659. pp. 1-3, May 23, 2019 (Year: 2019).

Rotival et al., "Integrating Genome-Wide Genetic Variations and Monocyte Expression Data Reveals TransRegulated Gene Modules in Humans", PLOS Genetics, 7(12): p. e1002367, (Dec. 1, 2011).

Sandborn et al. Target Mediated Disposition (TMD) Model Based Dose Selection for Fixed SC Doses of Anti-MAdCAM-1 Monoclonal Antibody (PF-00547659) in Crohn's Disease. 76th Annual Scientific Meeting of American College of Gastroenterology. Washington, DC, United States. Oct. 28-Nov. 2, 2011 (Year: 2011).

Sarlos et al., "Genetic update on inflammatory factors in ulcerative colitis: Review of the current literature", World Journal of Gastrointestinal Pathophysiology, 5(3): p. 304, (Jan. 1, 2014).

Vaughn et al., "Novel treatment options for ulcerative colitis", Clinical Nvestigation, UK, 3(11): 1057-1069 (Nov. 1, 2013).

Vermeire et al., "The mucosal addressing cell adhesion molecule antibody PF-00547,659 in ulcerative colitis: a randomized study", Gut, British Medical Association, London, UK, 60(8): 1068-1075 (Jan. 1, 2011).

Vermiere et al., "Correlation between fecal calprotectin levels and clinical activity in ulcerative colitis in a phase I study with an anti-MAdCAM-1 monoclonal antibody", J Crohns Colitis, vol. 6, No. S1, pp. S103-S104 (Feb. 1, 2012).

Williams, Jason and Comer, Gail. Target mediated disposition (TMD) model based dose selection for fixed sc doses of Anti-MAdCAM-1 monoclonal antibody (PF-00547659) in chron's disease. American Journal of Gastroenterology, (Oct. 2011) vol. 106, Supp. Suppl. 2, pp. S454-S455. Abstract #: 1207. (Year: 2011).

Ha C. et al. "Vedolizumab as a Treatment for Crohn's Disease and Ulcerative Colitis" Gastroenterol Hepatol (N Y); v.10, No. 12, p. 793-800 (2014).

* cited by examiner

DOSAGE REGIMEN FOR MADCAM ANTAGONISTS

CROSS REFERENCE TO RELATED APPLICATIONS

This application is a Divisional Application of U.S. application Ser. No. 15/542,110, filed Jul. 7, 2017, which is a National Stage Application filed under 35 U.S.C. § 371, of International Application No. PCT/IB2016/050047, filed Jan. 6, 2016, which claims priority to and the benefit of U.S. Application No. 62/101,877 filed Jan. 9, 2015, U.S. Application No. 62/263,197 filed Dec. 4, 2015, and U.S. Application No. 62/263,910 filed Dec. 7, 2015, the disclosures of each of which are hereby incorporated by reference.

INCORPORATION BY REFERENCE OF SEQUENCE LISTING

The content of the text file named "SHR-1258US2_ST25.txt", which was created on Jun. 29, 2017 and is 80 kilobytes in size, is hereby incorporated by reference in its entirety.

FIELD OF THE INVENTION

The present invention relates to dosage regimens of MAdCAM antagonist antibodies.

BACKGROUND OF THE INVENTION

Mucosal addressing cell adhesion molecule (MAdCAM; also known as addressing) is a member of the immunoglobulin superfamily of cell adhesion receptors. The selectivity of lymphocyte homing to specialized lymphoid tissue and mucosal sites of the gastrointestinal tract is determined by the endothelial expression of MAdCAM. MAdCAM is uniquely expressed on the cell surface of high endothelial venules of organized intestinal lymphoid tissue, such as Peyer's patches and mesenteric lymph nodes, but also in other lymphoid organs, such as pancreas, gall bladder and splenic venules and marginal sinus of the splenic white pulp.

While MAdCAM plays a physiological role in gut immune surveillance, it appears to facilitate excessive lymphocyte extravasation in inflammatory bowel disease under conditions of chronic gastrointestinal tract inflammation. TNFα and other pro-inflammatory cytokines increase endothelial MAdCAM expression and, in biopsy specimens taken from patients with Crohn's disease and ulcerative colitis (UC), there is an approximate 2-3 fold focal increase in MAdCAM expression at sites of inflammation. Similar patterns of elevated expression have been observed in experimental models of colitis. In other pre-clinical models for inflammatory conditions, such as insulin-dependent diabetes graft versus host disease, chronic liver disease, inflammatory encephalopathy, and gastritis, there is also reawakening of fetal MAdCAM expression and participation of activated $\alpha_4\beta_7^+$ lymphocytes in disease pathogenesis. In these inflammatory models as well as hapten-mediated (e.g., TNBS, DSS, etc.) or adoptive transfer (CD4$^+$CD45Rb$^{high}$) mouse colitic models, the rat anti-mouse MAdCAM monoclonal antibody (mAb), MECA-367, which blocks the binding of $\alpha_4\beta_7^+$ lymphocytes to MAdCAM, reduces the lymphocyte recruitment, tissue extravasation, inflammation and disease severity.

WO2005067620 discloses MAdCAM antagonist antibodies and uses thereof. WO2006096490 discloses MAdCAM antagonist antibodies and compositions thereof.

SUMMARY OF THE INVENTION

The invention provides embodiments as set forth below, each of which is indicated by E thereto:
E1. A method for treating a patient susceptible to or diagnosed with a condition associated with an increase in MAdCAM expression comprising administering to the patient an initial dose of between about 5 mg and about 150 mg of MAdCAM antagonist antibody.
E2. A method for treating a patient susceptible to or diagnosed with a condition associated with an increase in MAdCAM expression, comprising administering to the patient an initial dose of between about 5 mg and less than about 150 mg of MAdCAM antagonist antibody.
E3. A method for treating a patient susceptible to or diagnosed with ulcerative colitis (UC), comprising administering to the patient an initial dose of between about 5 mg and about 150 mg of MAdCAM antagonist antibody.
E4. A method for treating a patient susceptible to or diagnosed with UC, comprising administering to the patient an initial dose of between about 5 mg and less than about 150 mg of MAdCAM antagonist antibody.

Further embodiments are set forth below, where embodiments are indicated by "E".
E5. The method as set forth in any one of the preceding embodiments, comprising administering to the patient an initial dose of between about 7.5 mg and about 75 mg of MAdCAM antagonist antibody.
E6. The method as set forth in any one of the preceding embodiments, comprising administering to the patient an initial dose of between about 20 mg and about 75 mg of MAdCAM antagonist antibody.
E7. The method as set forth in any one of the preceding embodiments, comprising administering to the patient an initial dose of between about 22.5 mg and about 75 mg of MAdCAM antagonist antibody.
E8. The method as set forth in any one of the preceding embodiments, comprising administering to the patient an initial dose of between about 25 mg and about 75 mg of MAdCAM antagonist antibody.
E9. The method as set forth in any one of the preceding embodiments, comprising administering to the patient an initial dose of about 50 mg of MAdCAM antagonist antibody.
E10. The method as set forth in any one of the preceding embodiments, comprising administering to the patient an initial dose of between about 50 mg and about 150 mg of MAdCAM antagonist antibody.
E11. The method as set forth in any one of the preceding embodiments, comprising administering to the patient an initial dose of between about 75 mg and about 125 mg of MAdCAM antagonist antibody.
E12. The method as set forth in any one of the preceding embodiments, comprising administering to the patient an initial dose of between about 100 mg of MAdCAM antagonist antibody.
E13. The method as set forth in any one of the preceding embodiments, wherein the MAdCAM antagonist antibody is dosed at a range whose lower limit is selected from the group consisting of about 5 mg, about 6 mg, about 7 mg, about 7.5 mg, about 8 mg, about 9 mg, about 10 mg, about 12 mg, about 15 mg, about 20 mg, about 22.5 mg, about 25 mg, about 30 mg, about 35 mg, about 45 mg, about 50 mg, about 55 mg, about 65 mg, about 65 mg about 70 mg, about 75 mg, about 80 mg, about 85 mg, about 90 mg about 95 mg, about 100 mg and whose upper limit is selected from the group consisting of about 22.5 mg, about 25 mg, about 30 mg, about 35 mg, about 40 mg, about 45 mg, about 50 mg, about 55 mg, about 60 mg, about 65 mg, about 70 mg, less than about 75 mg, about 75 mg, about 80 mg, about 85 mg, about 90 mg, about 95 mg, about 100 mg, about 105 mg, about 110 mg, about 115 mg, about 120 mg, 125 mg, about 130 mg, about 135 mg, about 140 mg, about 145 mg, less than about 150 mg, and about 150 mg.

E14. The method as set forth in any one of the preceding embodiments, comprising administering to the patient one or more subsequent doses of the MAdCAM antagonist antibody.

E15. The method as set forth in E14, wherein the one or more subsequent doses of the MAdCAM antagonist antibody is administered in an amount that is about the same or less than the initial dose.

E16. The method as set forth in E14, wherein the one or more subsequent doses of the MAdCAM antagonist antibody is administered in an amount that is about the same as the initial dose.

E17. The method as set forth in any one of the preceding embodiments, comprising administering to the patient a subsequent dose of between about 5 mg and about 150 mg of MAdCAM antagonist antibody.

E18. The method as set forth in any one of the preceding embodiments, comprising administering to the patient a subsequent dose of between about 20 mg and about 75 mg of MAdCAM antagonist antibody.

E19. The method as set forth in any one of the preceding embodiments, comprising administering to the patient a subsequent dose of between about 22.5 mg and about 75 mg of MAdCAM antagonist antibody.

E20. The method as set forth in any one of the preceding embodiments, comprising administering to the patient a subsequent dose of between about 25 mg and about 75 mg of MAdCAM antagonist antibody.

E21. The method as set forth in any one of the preceding embodiments, comprising administering to the patient a subsequent dose of about 50 mg of MAdCAM antagonist antibody.

E22. The method as set forth in any one of the preceding embodiments, comprising administering to the patient a subsequent dose of between about 50 mg and about 150 mg of MAdCAM antagonist antibody.

E23. The method as set forth in any one of the preceding embodiments, comprising administering to the patient a subsequent dose of between about 75 mg and about 125 mg of MAdCAM antagonist antibody.

E24. The method as set forth in any one of the preceding embodiments, comprising administering to the patient a subsequent dose of between about 100 mg of MAdCAM antagonist antibody.

E25. The method as set forth in any one of the preceding embodiments, comprising administering to the patient a subsequent dose of MAdCAM antagonist antibody at a range whose lower limit is selected from the group consisting of about 5 mg, 6 mg, about 7 mg, about 7.5 mg, about 8 mg, about 9 mg, about 10 mg, about 12 mg, about 15 mg, about 20 mg, about 22.5 mg, about 25 mg, about 30 mg, about 35 mg, about 45 mg, about 50 mg, about 55 mg, about 65 mg, about 65 mg about 70 mg, about 75 mg, about 80 mg, about 85 mg, about 90 mg about 95 mg, and about 100 mg and whose upper limit is selected from the group consisting of 22.5 mg, about 25 mg, about 30 mg, about 35 mg, about 40 mg, about 45 mg, about 50 mg, about 55 mg, about 60 mg, about 65 mg, about 70 mg, less than about 75 mg, about 75 mg, about 80 mg, about 85 mg, about 90 mg, about 95 mg, about 100 mg, about 105 mg, about 110 mg, about 115 mg, about 120 mg, 125 mg, about 130 mg, about 135 mg, about 140 mg, about 145 mg, less than about 150 mg, and about 150 mg.

E26. The method as set forth in any one of the preceding embodiments, wherein a subsequent dose is administered in an amount that is about the same or less than the initial dose, said subsequent dose being provided between about 1 week and about 12 weeks after the initial dose.

E27. The method as set forth in any one of the preceding embodiments, wherein a subsequent dose is administered in an amount that is about the same or less than the initial dose, said subsequent dose being provided between about 4 weeks and about 12 weeks after the initial dose.

E28. The method as set forth in any one of the preceding embodiments, wherein a subsequent dose is administered in an amount that is about the same or less than the initial dose, said subsequent dose being provided between about 2 weeks and about 8 weeks after the initial dose.

E29. The method as set forth in any one of the preceding embodiments, wherein a subsequent dose is administered in an amount that is about the same or less than the initial dose, said subsequent dose being provided between about 4 weeks and about 8 weeks after the initial dose.

E30. The method as set forth in any one of the preceding embodiments, wherein a subsequent dose is administered in an amount that is about the same or less than the initial dose, said subsequent dose being provided about 4 weeks after the initial dose.

E31. The method as set forth in any one of the preceding embodiments, wherein a subsequent dose is administered in an amount that is about the same or less than the initial dose, said subsequent dose being provided about 1 month after the initial dose.

E32. The method as set forth in any one of the preceding embodiments, wherein a subsequent dose is administered in an amount that is about the same or less than the initial dose, said subsequent dose being provided about 6 weeks after the initial dose.

E33. The method as set forth in any one of the preceding embodiments, wherein a subsequent dose is administered in an amount that is about the same or less than the initial dose, said subsequent dose being provided about 8 weeks after the initial dose.

E34. The method as set forth in any one of the preceding embodiments, wherein a subsequent dose is administered in an amount that is about the same or less than the initial dose, said subsequent dose being provided about 2 months after the initial dose.

E35. The method as set forth in any one of the preceding embodiments, wherein the observed clinical remission rate at about 12 weeks after initial dose, as determined using the MAYO score, is at least about 3%.

E36. The method as set forth in any one of the preceding embodiments, wherein the observed clinical remission rate at about 12 weeks after initial dose, as determined using the MAYO score, is at least about 5%.

E37. The method as set forth in any one of the preceding embodiments, wherein the observed clinical remission rate at about 12 weeks after initial dose, as determined using the MAYO score, is at least about 10%.

E38. The method as set forth in any one of the preceding embodiments, wherein the observed clinical remission rate at about 12 weeks after initial dose, as determined using the MAYO score, is at least about 11%.

E39. The method as set forth in any one of the preceding embodiments, wherein the observed clinical remission rate at about 12 weeks after initial dose, as determined using the MAYO score, is at least about 12%.

E40. The method as set forth in any one of the preceding embodiments, wherein the observed clinical remission rate at about 12 weeks after initial dose, as determined using the MAYO score, is at least about 14%.

E41. The method as set forth in any one of the preceding embodiments, wherein the observed clinical remission rate at about 12 weeks after initial dose, as determined using the MAYO score, is at least about 15%.

E42. The method as set forth in any one of the preceding embodiments, wherein the observed clinical remission rate at about 12 weeks after initial dose, as determined using the MAYO score, is at least about 16%.

E43. The method as set forth in any one of the preceding embodiments, wherein the observed clinical remission rate at about 12 weeks after initial dose, as determined using the MAYO score, is at least about 18%.

E44. The method as set forth in any one of the preceding embodiments, wherein the observed clinical remission rate at about 12 weeks after initial dose, as determined using the MAYO score, is at least about 20%.

E45. The method as set forth in any one of the preceding embodiments, wherein the observed clinical remission rate at about 12 weeks after initial dose, as determined using the MAYO score, is at least about 23%.

E46. The method as set forth in any one of the preceding embodiments, wherein the clinical response rate at about 12 weeks after the initial dose is at least about 28%.

E47. The method as set forth in any one of the preceding embodiments, wherein the clinical response rate at about 12 weeks after the initial dose is at least about 30%.

E48. The method as set forth in any one of the preceding embodiments, wherein the clinical response rate at about 12 weeks after the initial dose is at least about 35%.

E49. The method as set forth in any one of the preceding embodiments, wherein the clinical response rate at about 12 weeks after the initial dose is at least about 38%.

E50. The method as set forth in any one of the preceding embodiments, wherein the clinical response rate at about 12 weeks after the initial dose is at least about 40%.

E51. The method as set forth in any one of the preceding embodiments, wherein the clinical response rate at about 12 weeks after the initial dose is at least about 45%.

E52. The method as set forth in any one of the preceding embodiments, wherein the clinical response rate at about 12 weeks after the initial dose is at least about 50%.

E53. The method as set forth in any one of the preceding embodiments, wherein the mucosal healing rate at about 12 weeks after the initial dose is at least about 10%.

E54. The method as set forth in any one of the preceding embodiments, wherein the mucosal healing rate at about 12 weeks after the initial dose is at least about 14%.

E55. The method as set forth in any one of the preceding embodiments, wherein the mucosal healing rate at about 12 weeks after the initial dose is at least about 15%.

E56. The method as set forth in any one of the preceding embodiments, wherein the mucosal healing rate at about 12 weeks after the initial dose is at least about 20%.

E57. The method as set forth in any one of the preceding embodiments, wherein the mucosal healing rate at about 12 weeks after the initial dose is at least about 25%.

E58. The method as set forth in any one of the preceding embodiments, wherein the mucosal healing rate at about 12 weeks after the initial dose is at least about 27%.

E59. The method as set forth in any one of the preceding embodiments, wherein the mucosal healing rate at about 12 weeks after the initial dose is at least about 30%.

E60. The method as set forth in any one of the preceding embodiments, wherein the mucosal healing rate at about 12 weeks after the initial dose is at least about 35%.

E61. The method as set forth in any one of the preceding embodiments, wherein the mucosal healing rate at about 12 weeks after the initial dose is at least about 37%.

E62. The method as set forth in any one of the preceding embodiments, wherein the patient is not taking a TNF antagonist or TNF inhibitor.

E63. The method as set forth in E62, wherein the TNF inhibitor is one or more selected from the group consisting of infliximab, etanercept, adalimumab, psoralen combined with ultraviolet A treatment (PUVA), certolizumab pegol, methotrexate, ciclosporin, curcumin, catechins, *cannabis*, and *Echinacea purpurea*.

E64. The method as set forth in any one of the preceding embodiments, wherein the MAdCAM antagonist antibody is administered subcutaneously.

E65. The method as set forth in any one of the preceding embodiments, wherein the patient is also treated with another pharmaceutical agent selected from the group consisting of AMG-181, adalimumab, alicaforsam, abatacept, aspirin, acetaminophen, azathioprine, AVX 470, AEB-071, amitriptyline, anthralin, acitretin, alefacept, alosetron, abatacept, amelubant, anakinra, apremilast, apilimod, aceclofenac, actarit, amoxapinet, budesonide, beclomethasone, betamethasone, balsalazide, benzothiazinone, benzocaine, belimumab, buprenorphine, celecoxib, cyclosporine, cortisone, certolizumab pegol, curcurmin, *cannabis*, ciprofloxacin; calcipotriene; cyclobenzaprine; clobetasol propionate, codeine, camphor, dexamethasone, doxepin, denosumab, diacerein, diclofenac, diflunisal, deflazacort, dipyridamole, dihydrocodeine, deracoxib, duloxetine, etrolizumab, etanercept, efalizumab, etodolac, eculizumab, etoricoxib, fluoxetine, fontolizumab, felbinac, fenoprofen, fentanyl, golimumab, gabapentin, hmpl- 004, hydromorphone, hydrocodone, indomethacin, Ibuprofen, Infliximab, interleukin-2, imipramine, iberogast, imidazole salicylate, iguratimod, immunoglobulin, hydroxycortisone, hydroxyurea, hylauronic acid, kappaproct, krp-203, loperamide, lornoxicam, lumericoxib, leflunomide, licofelone, lumiracoxib, lidocaine, methylprednisolone 6-mercaptopurine, methotrexate, metronidazole, mesalamine, melatonin, mesalamine, meloxicam, misoprostol, methyl salicylate, naproxen sodium, nicotine, nortriptyline, nambumetone, nepafenac, noradrenaline, norepinephrine, olsalazine, OM-89, Otzela, oprelvekin, ofatumumab, ocrelizumab, oxycodone, oxymorphone, Prednisone, prednisolone, phosphatidyl choline, paroxetine, paclitaxel, prosorba, pelubiprofen, piroxicam, pegsunercept, pralnacasan, prinaberel, parecoxib, pregabalin, rimexolone, risedronate sodium, rosiglitazone, rofecoxib, ropivacaine, reboxetine, (S,S)-reboxetine, reumacon, sulfasalazine, sulfasalazineloperamide, sertraline, sildenafil, tramadol, triamcinolone, tacrolimus, thalidomide, tofacitinib, *trichuris suis*, trazodone, tazarotene, tegaserod, tocilizumab, temsirolimus, tenoxicam, valdecoxib, vedolizumab, Xeljanz, zolpidem, zoledronic acid, 153Sm-EDTMP, and SK-1306X and 10rT1 antibody, CP-481715, ABN-912, MLN-3897, HuMax-IL-15, RA-1, Org-37663, Org 39141, AED-9056, AMG-108, GW-274150, AT-001, 681323 (GSK) K-832, R-1503, DE-096, Cpn10, THC+CBD (GW Pharma), 856553 (GSK), ReN-1869, mm-093, SCIO-469, ABT-874, LenkoVAX, LY-2127399, TRU-015, KC-706, and TAK-715, PG 760564, VX-702, PMX-53, CF-101, tgAAV-TNFR:Fc, R-788, PMI-001, S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S, 5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, N-[({2-[4-(2-ethyl-4,6-dimethyl-1H-imidazo[4,5-c]pyridin-1-yl)phenyl]ethyl}amino)-carbonyl]-4-methylbenzenesulfonamide, 4-[(1S)-1-({[5-chloro-2-(3-fluorophenoxy)pyridin-3-yl]carbonyl}amino)ethyl] benzoic acid, and 1-(3-biphenyl-4-ylmethyl-4-hydroxy-chroman-7-yl)-cyclopentanecarboxylic acid.

E66. The method as set forth in E65, wherein the patient is treated concurrently with the MAdCAM antibody and the other pharmaceutical agent.

E67. The method as set forth in E65, wherein the patient is treated sequentially with the MAdCAM antibody and the other pharmaceutical agent.

E68. The method as set forth in any one of the preceding embodiments, wherein the MAdCAM antagonist antibody comprises a light chain whose CDRs are according to the CDRs of SEQ ID NO:3, and a heavy chain whose CDRs are according to the CDRs of SEQ ID NO:4.

E69. The method as set forth in any one of the preceding embodiments, wherein the MAdCAM antagonist antibody comprises SEQ ID NO:3 and SEQ ID NO:4.

E70. The method as set forth in any one of the preceding embodiments, wherein the MAdCAM antagonist antibody comprises SEQ ID NO:1 and SEQ ID NO:2.

E71. The method as set forth in any one of the preceding embodiments, comprising administering to the patient an initial dose of between about 22.5 mg and about 75 mg of MAdCAM antagonist antibody, followed by one or more subsequent doses of the MAdCAM antagonist antibody in an amount that is about the same as the initial dose, wherein the one or more subsequent doses are doses about every 4 weeks.

E72. The method as set forth in any one of the preceding embodiments, comprising administering to the patient an initial dose of about 50 mg of MAdCAM antagonist antibody, followed by one or more subsequent doses of the MAdCAM antagonist antibody in an amount that is about the same as the initial dose, wherein the one or more subsequent doses are doses about every 4 weeks.

E73. The method as set forth in any one of embodiments E1-E71, comprising administering to the patient an initial dose of about 40 mg of MAdCAM antagonist antibody, followed by one or more subsequent doses of the MAdCAM antagonist antibody in an amount that is about the same as the initial dose, wherein the one or more subsequent doses are doses about every 4 weeks.

E74. The method as set forth in any one of embodiments E1-E71, comprising administering to the patient an initial dose of about 30 mg of MAdCAM antagonist antibody, followed by one or more subsequent doses of the MAdCAM antagonist antibody in an amount that is about the same as the initial dose, wherein the one or more subsequent doses are doses about every 4 weeks.

E75. The method as set forth in any one of embodiments E1-E71, comprising administering to the patient an initial dose of between about 50 mg and about 150 mg of MAdCAM antagonist antibody, followed by one or more subsequent doses of the MAdCAM antagonist antibody in an amount that is about the same as the initial dose, wherein the one or more subsequent doses are doses about every 8 weeks.

E76. The method as set forth in any one of embodiments E1-E71, comprising administering to the patient an initial dose of between about 75 mg and about 125 mg of MAdCAM antagonist antibody, followed by one or more subsequent doses of the MAdCAM antagonist antibody in an amount that is about the same as the initial dose, wherein the one or more subsequent doses are doses about every 8 weeks.

E77. The method as set forth in any one of embodiments E1-E71, comprising administering to the patient an initial dose of about 100 mg of MAdCAM antagonist antibody, followed by one or more subsequent doses of the MAdCAM antagonist antibody in an amount that is about the same as the initial dose, wherein the one or more subsequent doses are doses about every 8 weeks.

E78. The method as set forth in any one of the preceding embodiments, wherein the a condition associated with an increase in MAdCAM expression is selected from the group consisting of ulcerative colitis (UC), Crohn's disease (CD), Irritable bowel syndrome (IBS), irritable bowel disease (IBD), rheumatoid arthritis, reactive arthritis, osteoarthritis, infectious arthritis, psoriatic arthritis, polyarthritis, juvenile arthritis, juvenile rheumatoid arthritis, juvenile reactive arthritis, juvenile psioriatic arthritis, pain, fibrosis, fibromyalgia syndrome, ankylosing spondylitis, undifferentiated spondyloarthropathy, juvenile onset spondylarthritis, psoriasis, gout, Castleman's disease, sepsis, type I diabetes, type II diabetes, multiple myeloma, and renal cell carcinoma.

E79. The MAdCAM antagonist antibody for use in a method as set forth in any one of embodiments E1-E78.

E80. A pharmaceutical composition comprising an antibody as set forth in E79.

E81. The pharmaceutical composition as set forth in E80 comprising the MAdCAM antagonist antibody as dry formulation for dissolution such as a lyophilized powder, freeze-dried powder or water free concentrate.

E82. The pharmaceutical composition as set forth in E80, comprising the MAdCAM antagonist antibody as liquid formulation.

E83. Use of a MAdCAM antagonist antibody as set forth in E79 in the preparation of a medicament for the treatment of a condition selected from the group consisting of ulcerative colitis (UC), Crohn's disease (CD), Irritable bowel syndrome (IBS), irritable bowel disease (IBD), Celiac disease, primary sclerosing cholangitis, biliary disease, rheumatoid arthritis, reactive arthritis, osteoarthritis, infectious arthritis, psioriatic arthritis, polyarthritis, juvenile arthritis, juvenile rheumatoid arthritis, juvenile reactive arthritis, juvenile psioriatic arthritis, pain, fibrosis, fibromyalgia syndrome, ankylosing spondylitis, undifferentiated spondyloarthropathy, juvenile onset spondylarthritis, psoriasis, gout, Castleman's disease, sepsis, type I diabetes, type II diabetes, multiple myeloma, and renal cell carcinoma.

E84. Use of a MAdCAM antagonist antibody as set forth in E79 in the preparation of a medicament for the treatment of ulcerative colitis.

E85. Use of a MAdCAM antagonist antibody as set forth in E79 in the preparation of a medicament for the treatment of Crohn's Disease E86. The method of any one of embodiments E1-E78, further comprising:
(a) measuring the level of a biomarker in a biological sample from said patient, wherein said biomarker is: (i) any one or combination of the biomarkers selected from the group consisting of: Fecal calprotectin, sMAdCAM, hsCRP, AR, CHI3L1, CXCL1, CXCL11, CXCL13, CXCL9. Dkk-1, EGF, EN-RAGE, EPO, FGF-21, GH, IL-17C, IL-6, IL-7, IL-8, MIP-1 alpha, MMP-1, MMP-10, MMP-12, MMP-3, NT-pro-BNP, OSM, PTPN22, PTX3, REG-4, RETN, TNFRSF4, TRANCE, and VEGF-A; (ii) CCR9; (iii) circulating α4β7+ cells; or (iv) any combination of the foregoing; and
(b) comparing said level with a control;
such that a change in the level of the biomarker, as compared to the control, is predictive of a beneficial therapeutic response in the condition.

E87. A method for assessing the presence or absence of a beneficial response in an ulcerative colitis (UC) patient after administering a MAdCAM antagonist antibody, comprising: (a) measuring the level of a biomarker in a biological sample from said patient, wherein said biomarker is: (i) any one or combination of the biomarkers selected from the group consisting of: Fecal calprotectin, sMAdCAM, hsCRP, AR, CHI3L1, CXCL1, CXCL11, CXCL13, CXCL9. Dkk-1, EGF, EN-RAGE, EPO, FGF-21, GH, IL-17C, IL-6, IL-7, IL-8, MIP-1 alpha, MMP-1, MMP-10, MMP-12, MMP-3, NT-pro-BNP, OSM, PTPN22, PTX3, REG-4, RETN, TNFRSF4, TRANCE, and VEGF-A; (ii) CCR9; (iii) circulating α4β7+ cells; or (iv) any combination of the foregoing; and
(b) comparing said level with a control;
wherein a change in the level of biomarker, as compared to the control, is predictive of a beneficial response in said patient.

E88. A method for identifying an ulcerative colitis (UC) patient who would benefit from treatment with a MAdCAM antagonist antibody, comprising:
(a) measuring the level of a biomarker in a biological sample from said patient, wherein said biomarker is: (i) any one or combination of the biomarkers selected from the group consisting of: Fecal calprotectin, sMAdCAM, hsCRP, AR, CHI3L1, CXCL1, CXCL11, CXCL13, CXCL9. Dkk-1, EGF, EN-RAGE, EPO, FGF-21, GH, IL-17C, IL-6, IL-7, IL-8, MIP-1 alpha, MMP-1, MMP-10, MMP-12, MMP-3, NT-pro-BNP, OSM, PTPN22, PTX3, REG-4, RETN, TNFRSF4, TRANCE, and VEGF-A; (ii) CCR9; (iii) circulating α4β7+ cells; or (iv) any combination of the foregoing;
(b) comparing said level with a control; wherein a change in the level of biomarker, as compared to the control, predicts that said patient would benefit from treatment with a MAdCAM antagonist antibody; and
(c) selecting said patient for treatment with a MAdCAM antagonist antibody.

E89. The method of any one of embodiments E86-E88, wherein said biomarker is selected from the group consisting of: Fecal calprotectin, sMAdCAM, hsCRP, AR, CHI3L1, CXCL1, CXCL11, CXCL13, CXCL9. Dkk-1, EGF, EN-RAGE, EPO, FGF-21, GH, IL-17C, IL-6, IL-7, IL-8, MIP-1 alpha, MMP-1, MMP-10, MMP-12, MMP-3, NT-pro-BNP, OSM, PTPN22, PTX3, REG-4, RETN, TNFRSF4, TRANCE, VEGF-A, and any combination of the foregoing.

E90. The method of any one of embodiments E86-E89, wherein said biomarker is selected from the group consisting of: Fecal calprotectin, sMAdCAM, hsCRP, CHI3L1, CXCL1, CXCL13, CXCL9. Dkk-1, EGF, EN-RAGE, EPO, IL-17C, IL-6, IL-7, MIP-1 alpha, MMP-1, MMP-10, MMP-12, MMP-3, NT-pro-BNP, PTPN22, PTX3, RETN, TNFRSF4, TRANCE, and any combination of the foregoing.

E91. The method of any one of embodiments E86-E90, wherein said biomarker is selected from the group consisting of: Fecal calprotectin, sMAdCAM, hsCRP, AR, CXCL11, CXCL13, EPO, FGF-21, GH, IL-6, IL-7, IL-8, MMP-1, MMP-10, MMP-3, OSM, PTPN22, REG-4, RETN, VEGF-A, and any combination of the foregoing.

E92. The method of any one of embodiments E86-E91, wherein said biomarker is selected from the group consisting of: Fecal calprotectin, sMAdCAM, hsCRP, CXCL13, EPO, IL-6, IL-7, MMP-1, MMP-10, MMP-3, PTPN22, RETN, and any combination of the foregoing.

E93. The method of any one of embodiments E86-E92, wherein said biomarker is selected from the group consisting of: Fecal calprotectin, sMAdCAM, hsCRP, CXCL13, IL-7, PTPN22, RETN, and any combination of the foregoing.

E94. The method of any one of embodiments E86-E93, wherein said biomarker is selected from the group consisting of: Fecal calprotectin, sMAdCAM, hsCRP, and any combination of the foregoing.

E95. The method of any one of embodiments E86-E94, wherein said biomarker is: (i) fecal Calprotectin, sMAdCAM, or hsCRP; (ii) CCR9; (iii) circulating α4β7+ cells; or (iv) any combination of the foregoing.

E96. The method of any one of embodiments E86-E95, wherein said biomarker is fecal Calprotectin, and wherein a decrease in fecal Calprotectin level, as compared to a control, predicts that said patient would benefit from treatment with a MAdCAM antagonist antibody.

E97. The method of any one of embodiments E86-E95, wherein said biomarker is sMAdCAM, and wherein a decrease in sMAdCAM level, as compared to a control, predicts that said patient would benefit from treatment with a MAdCAM antagonist antibody.

E98. The method of any one of embodiments E86-E95, wherein said biomarker is hsCRP, and wherein a decrease in hsCRP level, as compared to a control, predicts that said patient would benefit from treatment with a MAdCAM antagonist antibody.

E99. The method of any one of embodiments E86-E88 and E95, wherein said biomarker is CCR9, and wherein an increase in CCR9 level, as compared to a control, predicts that said patient would benefit from treatment with a MAdCAM antagonist antibody.

E100. The method of any one of embodiments E86-E88 and E95, wherein said biomarker is circulating α4β7+ cells, and wherein an increase in circulating α4β7+ cell level, as compared to a control, predicts that said patient would benefit from treatment with a MAdCAM antagonist antibody.

E101. The method of any one of embodiments E86-E100, wherein said biological sample is obtained at least about 4 weeks after administering a MAdCAM antagonist antibody.

E102. The method of any one of embodiments E86-E101, wherein said biological sample is obtained from about 4 weeks to about 12 weeks after administering a MAdCAM antagonist antibody.

E103. The method of any one of embodiments E86-E102, wherein said biological sample is obtained about 12 weeks after administering a MAdCAM antagonist antibody.

E104. The method of any one of embodiments E1-E78 and E86-E103, wherein said patient further comprises risk allele (C) at rs11171739.

E105. A method for identifying an ulcerative colitis (UC) patient who would benefit from treatment with a MAdCAM antagonist antibody, comprising:
(a) assaying a biological sample that comprises genomic DNA from said patient; and
(b) obtaining SNP rs11171739 sequence from said genomic DNA;
wherein the presence of risk allele (C) at rs11171739 predicts that said patient would benefit from treatment with a MAdCAM antagonist antibody.

E106. A method of treating a patient susceptible to or diagnosed with a condition associated with an increase in MAdCAM expression comprising administering to the patient an initial dose of between about 5 mg and about 150 mg of MAdCAM antagonist antibody, wherein said patient comprises risk allele (C) at rs11171739.

E107. A method of treating a patient susceptible to or diagnosed with a condition associated with an increase in MAdCAM expression comprising administering to the patient an initial dose of between about 5 mg and about 150 mg of MAdCAM antagonist antibody, wherein said is identified by any one of the method of embodiments E86-E105.

E108. A kit comprising:
(a) a detection agent for detecting the presence of a biomarker, or for measuring the level of a biomarker in a biological sample, wherein said biomarker is: (i) any one of the biomarkers listed in Tables 12, 13, 15; (ii) circulating α4β7+ cells; (iii) rs11171739 risk allele; or (iv) any combination of the foregoing; and
(b) instructions to use said detection agent.

The invention provides as a further embodiment that may be used independent or in combination with any of the previous embodiments, a method for the treatment of a patient susceptible to or diagnosed with a condition associated with an increase in MAdCAM expression comprising administering to the patient an initial dose of between about 5 mg and about 150 mg of MAdCAM antagonist antibody following one or more doses of tofacitinib.

BRIEF DESCRIPTION OF THE DRAWINGS

FIG. 2: Analysis results of placebo corrected clinical remission rate, clinical response rate and mucosal healing rate based on total mayo score at week 12 (cmh method, central read, mitt population).

FIG. 1: Analysis results of placebo corrected clinical remission rate, clinical response rate and mucosal healing rate based on total mayo score at week 12 (cmh method, local read, mitt population).

FIG. 2: Analysis results of proportion of subjects with decrease from baseline in partial mayo score of ≤2 with no individual subscore >1 at weeks 4, 8, 12 (cmh method, mitt population).

FIG. 3: Proportions (and 90% confidence interval) of subjects with clinical remission (defined as a total sccai score of <2 points) at weeks 4, 8 and 12. *the confidence intervals are computed using exact method.

DETAILED DESCRIPTION

Figure 1A:
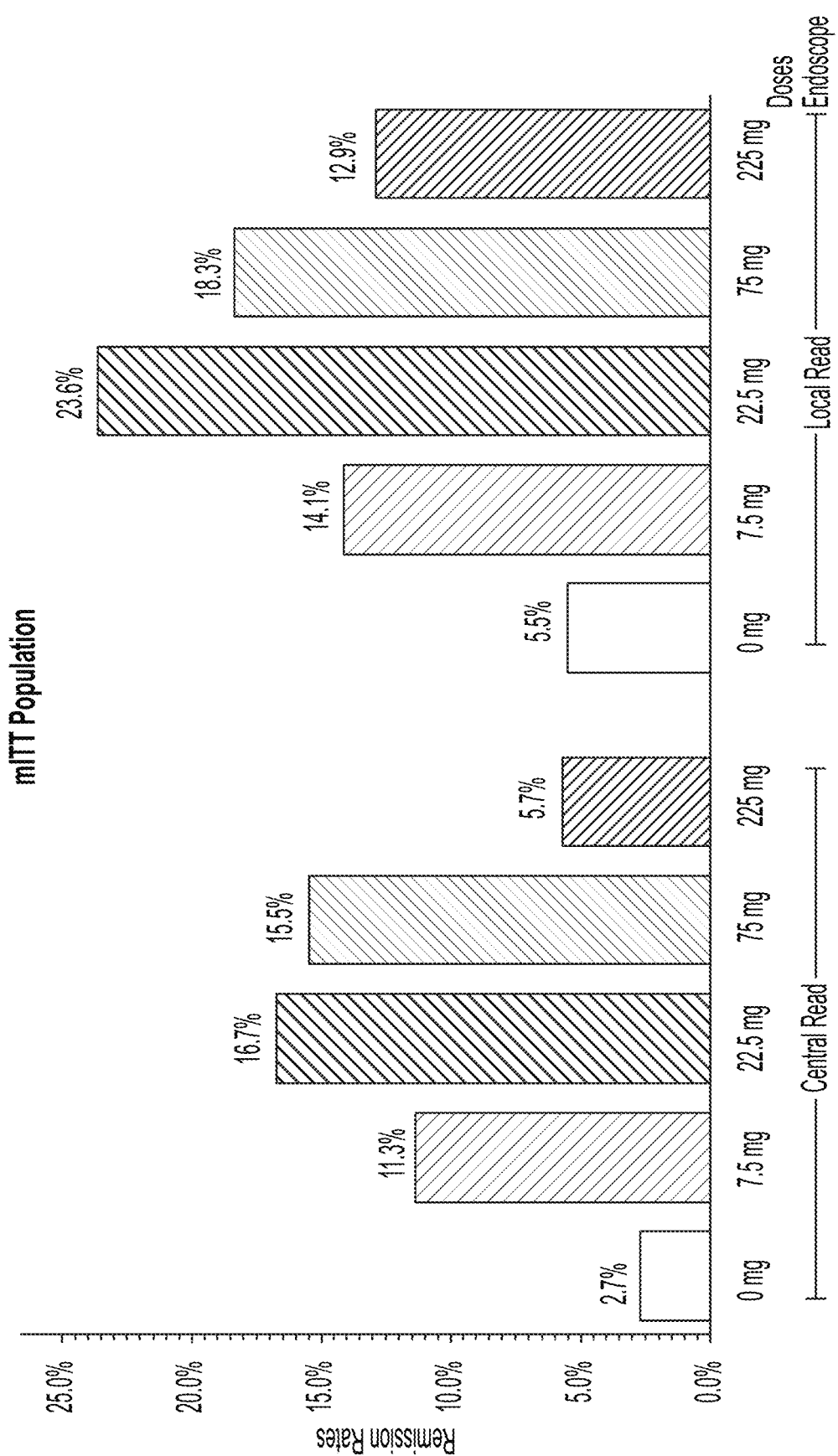
FIG. 1A and FIG. 1B: Clinical remission rate based on total mayo score at week 12 (treatment failure approach).

The present invention provides a method for the treatment of a patient, comprising administering to the patient susceptible to or diagnosed with ulcerative colitis (UC), comprising an initial dose of between about 5 mg and about 75 mg of MAdCAM antagonist antibody. The present invention provides a method for the treatment of a patient susceptible to or diagnosed with a condition associated with an increase in MAdCAM expression comprising administering to the patient an initial dose of between about 5 mg and about 150 mg of MAdCAM antagonist antibody. In some aspects, the increase in MAdCAM expression is as compared to MAdCAM in healthy individuals.

In a phase II randomized, multicenter double-blind, placebo-controlled study of the safety and efficacy of mAb 7.16.6 in patients with moderate to severe ulcerative colitis, emission and mucosal healing were significantly greater in the 22.5 mg and 75 mg dose groups vs placebo, while response was significantly greater for 22.5 mg and 225 mg groups vs placebo.

The MAdCAM antagonist antibody may be dosed at 25 mg (initial and/or subsequent dose(s)). The MAdCAM antagonist antibody may be dosed at 50 mg (initial and/or subsequent dose(s)). The MAdCAM antagonist antibody may be dosed at 75 mg. The MAdCAM antagonist antibody may be dosed at 25 mg (initial and/or subsequent dose(s)).

mAb 7.16.6 met the primary efficacy endpoint in the study. Clinical remission rates based on the Total Mayo score were statistically significant in three of four treatment groups (7.5 mg, 22.5 mg and 75 mg). Clinical remission rates by stratum of anti-TNF exposure (experienced or naïve) were higher among naïve patients. Key secondary endpoint results for Clinical Response, Mucosal Healing and Partial Mayo score generally supported the findings of primary endpoint analysis. mAb 7.16.6 appears safe and well-tolerated in this patient population.

In some aspects, the patient is not taking a TNF antagonist or TNF inhibitor. In some aspects, the patent has not taken a TNF antagonist or TNF inhibitor for at least about 1 week prior to the initial dose. In some aspects, the patent has not taken a TNF antagonist or TNF inhibitor for at least about 2 weeks prior to the initial dose. In some aspects, the patent has not taken a TNF antagonist or TNF inhibitor for at least about 3 weeks prior to the initial dose. In some aspects, the patent has not taken a TNF antagonist or TNF inhibitor for at least about 4 weeks prior to the initial dose. In some aspects, the patent has not taken a TNF antagonist or TNF inhibitor for at least about 5 weeks prior to the initial dose. In some aspects, the patent has not taken a TNF antagonist or TNF inhibitor for at least about 6 weeks prior to the initial dose. In some aspects, the patent has not taken a TNF antagonist or TNF inhibitor for at least about 7 weeks prior to the initial dose. In some aspects, the patent has not taken a TNF antagonist or TNF inhibitor for at least about 8 weeks prior to the initial dose. In some aspects, the patent has never taken a TNF antagonist or TNF inhibitor prior to the initial dose.

Using centrally read endoscopic subscores in the total Mayo score calculation (henceforth central read) at week 12, the observed Clinical Remission rates (mITT population) in placebo, 7.5 mg, 22.5 mg, 75 mg and 225 mg of mAb 7.16.6 were 2.7%, 11.3%, 16.7%, 15.5%, and 5.7%, respectively; and the difference from placebo and the corresponding two-sided 90% confidence intervals (CIs) using CMH test were 8.0% (1.9%, 14%), 12.8% (5.6%, 19.9%), 11.8% (4.8%, 18.8%) and 2.6% (−1.2%, 6.4%), respectively.

Using locally read endoscopic subscores in the total Mayo score calculation (henceforth local read), the observed Clinical Remission rates (mITT population) of placebo, 7.5 mg, 22.5 mg, 75 mg and 225 mg of mAb 7.16.6 were 5.5%, 14.1%, 23.6%, 18.3%, and 12.9% respectively; and the difference from placebo and the corresponding 90% CIs using CMH test were 8.0% (0.2%, 15.9%), 17.8% (8.3%, 27.2%), 12.2% (3.6%, 20.8%) and 6.6% (−0.9%, 14.2%), respectively.

Accordingly, in the some aspects, the observed Clinical Remission rate at about 12 weeks after initial dose, as determined using the MAYO score, may be selected from the group consisting of at least about 3%, at least about 5%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 21%, at least about 22%, and at least about 23%.

Using central read subscores at week 12, the observed response rates of placebo, 7.5 mg, 22.5 mg, 75 mg and 225 mg were 28.8%, 38.0%, 54.2%, 45.1% and 50.0%, respectively; and the corresponding Mucosal Healing rates were 8.2%, 15.5%, 27.8%, 25.4% and 14.3%, respectively. When using local read subscores, the observed rates were higher than the central read; for placebo, 7.5 mg, 22.5 mg, 75 mg and 225 mg the Clinical Response rates were 32.9%, 38.6%, 54.2%, 48.6% and 51.4%, respectively, and the Mucosal Healing rates were 21.9%, 22.5%, 37.5%, 35.2% and 28.6%, respectively. Clinical Response rates for 22.5 mg and 225 mg treatment groups over placebo group were significantly different from placebo regardless of endoscopic subscore source. The Mucosal Healing rates using central read are in general lower than the local read, and the trend is consistent with the other endpoints.

Accordingly, in the some aspects, the observed Clinical Response rate at about 12 weeks after initial dose, as determined using the MAYO score, may be selected from the group consisting of at least about 25%, at least about 27%, at least about 28%, at least about 30%, at least about 32%, at least about 33%, at least about 35%, at least about 37%, at least about 38%, at least about 40%, at least about 42%, at least about 43%, at least about 45%, at least about 47%, at least about 48%, and at least about 50%.

Accordingly, in some aspects, the Mucosal Healing rate at about 12 weeks after initial dose, as determined using the MAYO score, may be selected from the group consisting of at least about 10%, at least about 14%, at least about 15%, at least about 20%, at least about 25%, at least about 27%, at least about 30%, at least about 35%, and at least about 37%.

mAb 7.16.6 appears safe and well-tolerated in this patient population. Most common adverse events were related to the underlying disease, and occurred during the first month of treatment in the placebo and 7.5 mg treatment arms.

Serum mAb 7.16.6 exposure was consistent with that observed in the UC Phase I study (ClinicalTrials.gov Identifier: NCT00928681) and adequately predicted by the preliminary population pharmacokinetic model describing target mediated drug disposition. These PK levels corresponded to suppression of soluble MAdCAM (at week 12) ranging from 68 to 98%, consistent with model predictions during the design of the study. The overall confirmatory antidrug antibody (ADA) positive rate was approximately 6.4%. There was no indication of treatment boosted ADA response. Preliminary evaluation in subjects with confirmatory positive ADAs post-baseline indicated no discernable effect of ADAs on exposure, safety or efficacy.

Biomarkers

The invention further provides molecular biomarkers, such as genetic mutations, transcriptomic RNA expression, cellular protein markers and various measures of response to anti-MAdCAM treatment in patients, especially those with ulcerative colitis (UC). For example, biomarkers can be used to establish the underlying mechanistic basis for the observed non-monotonic dose response observed in subjects with ulcerative colitis after treatment with mAb 7.16.6. mAb 7.16.6 treatment results in preferential inhibition of immune effector over regulatory cells at the lower clinically efficacious doses, which normalizes at the higher clinically less efficacious doses. Accordingly, biomarkers related to regulatory cells can be used to optimize future dose selection. Further, biomarkers can also be used to select sub-populations of UC patients that are particularly responsive to anti-MAdCAM antibody treatment.

For example, a UC patient may be administered with at least an initial dose of a MAdCAM antagonist antibody, and optionally one or more subsequent doses at a fixed interval (in the examples, the patients were dosed at every 4 weeks). Optionally at or at least about 4 weeks, at or at least about 8 weeks, at or at least about 12 weeks, after initial dose, one or more biomarkers in said patient may be assessed to predict whether a future beneficial therapeutic response is likely. A positive biomarker assay result would suggest that the patient would benefit from continuing with anti-MAdCAM treatment. Biomarkers may be assessed prior to anti-MAdCAM treatment, to select sub-populations of patients who would likely benefit from anti-MAdCAM treatment. Biomarkers may also be continuously monitored during the course of treatment, e.g. to either adjust dose or to determine whether treatment should continue.

Four types of biomarkers are provided herein: genetic biomarkers (such as SNP rs11171739), RNA transcript markers (such as CCR9 transcript), protein biomarkers (such as Fecal Calprotectin, sMAdCAM, and hsCRP), and cellular biomarkers (such as α4β7+ cells). Any of these biomarkers can be used, singularly or in any combination, to assess therapeutic effect and/or patient sub-population.

In one aspect, the invention provides a method for assessing the presence or absence of a beneficial response in a patient after administration of a MAdCAM antagonist antibody, comprising: (a) measuring the level of a biomarker in a biological sample from said patient; (b) comparing said level with a control; wherein a change in the level of biomarker, as compared to the control, is predictive of a beneficial response in said patient. In another aspect, the invention provides a method for assessing the presence or absence of a beneficial response in a patient after administration of a MAdCAM antagonist antibody, comprising: (a) obtaining or receiving a biological sample from said patient; (b) measuring the level of a biomarker in said biological sample; (c) comparing said level with a control; wherein a change in the level of biomarker, as compared to the control, is predictive of a beneficial response in said patient. Such patient may continue with MAdCAM antagonist antibody treatment. Further dosage may be adjusted according to changes in biomarker levels to achieve desired therapeutic effect. For example, the dose may be increased if changes in biomarker levels in a patient have not reached a minimal threshold.

A skilled artisan will be able to determine what an appropriate control is. In certain embodiments, a control is the level of said biomarker prior to anti-MAdCAM treatment. In certain embodiments, a control is the level of said biomarker at certain time points during treatment (e.g., 1 week after initial dose, 2 weeks after initial dose). In certain embodiments, a control is a predetermined value (e.g., a threshold value, or an average level in patient population).

In certain embodiments, said biomarker is any one or any combination of protein biomarkers in Table 12, and Fecal calprotectin, sMAdCAM, and hsCRP. In certain embodiments, said biomarker is any one or any combination of protein biomarkers in Table 13, and Fecal calprotectin, sMAdCAM, and hsCRP. In certain embodiment, said biomarker is any one or any combination of RNA transcript biomarkers in Table 15, such as CCR9. In certain embodiments, said biomarker is circulating α4β7+ cells. Any combination of protein, RNA, and cell biomarkers disclosed herein may also be used.

In certain embodiments, the biomarker is: (i) any one or combination of the biomarkers selected from the group consisting of: Fecal calprotectin, sMAdCAM, hsCRP, AR, CHI3L1, CXCL1, CXCL11, CXCL13, CXCL9. Dkk-1, EGF, EN-RAGE, EPO, FGF-21, GH, IL-17C, IL-6, IL-7, IL-8, MIP-1 alpha, MMP-1, MMP-10, MMP-12, MMP-3, NT-pro-BNP, OSM, PTPN22, PTX3, REG-4, RETN, TNFRSF4, TRANCE, and VEGF-A; (ii) CCR9; (iii) circulating α4β7+ cells; or (iv) any combination of the foregoing.

In one aspect, the invention provides a method for identifying a patient who would benefit from treatment of a MAdCAM antagonist antibody, comprising: (a) obtaining a biological sample from said patient; (b) detecting the presence of rs11171739 risk allele in said sample; wherein the presence of rs11171739 risk allele is predictive of a beneficial response to MAdCAM antagonist antibody treatment in said patient. rs11171739 is a SNP at 12q13.2 locus (position 56076841), and is reportedly associated with expression of the MADCAM1 gene, and certain autoimmune diseases. Normal allele (oriented to the dbSNP entry) is (T) (allele frequency 55.5%), and risk allele is (C) (allele frequency 44.5%). For genotype frequencies, (T;T) is 40.9%, (C;T) is 32.8%, and (C;C) is 26.3%.

Variations combinations of the disclosed genomic, RNA, protein and cell biomarkers may be used. For example, patient subpopulation may be identified by combination of CCR9 transcript and sMAdCAM, or combination of rs11171739 risk allele, CCR9, and sMAdCAM.

In some aspects, the invention provides for a method of assessing patient's suitability for a treatment regime for a condition, comprising:

measuring the gene expression levels of one or more genes selected from the group consisting of Fecal Calprotectin, sMAdCAM, and hsCRP prior to treatment;

measuring the expression levels of the genes measured in step (i) after the patient has been treated with the MAdCAM antagonist antibodies according to the invention, comparing the gene expression levels from steps (i) and (ii) and identifying increases or decreases in expression;

continuing treatment of the patient based on a change in gene expression of one or more of the genes.

In some aspects, the gene is Fecal Calprotectin. In some aspects, the gene is soluble MAdCAM (sMAdCAM). In some aspects, the gene is hsCRP.

In another aspect, the invention provides a kit for assessing the presence or absence of a beneficial response in a patient after administration of a MAdCAM antagonist antibody, comprising: (a) a detection agent for detecting the presence of a biomarker described herein, or for measuring the level of a biomarker described herein; (b) instructions to use said detection agent. The detection agent can comprise a probe that specifically binds to the biomarker.

The biomarker can be any biomarker from Tables 12, 13, 15; Fecal calprotectin, sMAdCAM, hsCRP; α4β7+ cells, rs11171739; or any combination thereof, as disclosed herein.

The probe can be an oligonucleotide (e.g., for binding to a DNA or RNA biomarker), an antibody (e.g., for binding to a protein biomarker), or a ligand, aptamer, or small molecule that specifically binds to said biomarker. The probe can be labeled with a detectable marker (e.g., a fluorescent tag) for determining the presence or absence of said biomarker, or to quantify the level of said biomarker.

In another aspect, the invention provides a method for treating a patient susceptible to or diagnosed with a condition associated with an increase in MAdCAM expression comprising administering to the patient an initial dose of between about 5 mg and about 150 mg of MAdCAM antagonist antibody, wherein said patient is identified by: (a) administering an initial dose of a MAdCAM antagonist antibody to said patient; (b) assaying a biological sample from said patient about 4 weeks or longer (e.g., about 8 weeks, about 12 weeks, about 16 weeks, or about 20 weeks) after the initial administration, comprising the steps of: (i) measuring the level of a biomarker in said biological sample; (ii) comparing said level with a control; wherein a change in the level of biomarker, as compared to the control, is predictive of the presence of a beneficial response in said patient. In another aspect, the invention provides a method for treating a patient susceptible to or diagnosed with a condition associated with an increase in MAdCAM expression comprising administering to the patient an initial dose of between about 5 mg and about 150 mg of MAdCAM antagonist antibody, wherein said patient is identified by: (a) administering an initial dose of a MAdCAM antagonist antibody to said patient; (b) obtaining or receiving a biological sample from said patient about 4 weeks or longer (e.g., about 8 weeks, about 12 weeks, about 16 weeks, or about 20 weeks) after the initial administration; (c) measuring the level of a biomarker in said biological sample; (d) comparing said level with a control; wherein a change in the level of biomarker, as compared to the control, is predictive of the presence of a beneficial response in said patient. Such patient may continue with MAdCAM antagonist antibody treatment. Further dosage may be adjusted according to changes in biomarker levels to achieve desired therapeutic effect. For example, the dose may be increased if changes in biomarker levels in a patient have not reached a minimal threshold. Again, various controls can be used, such as level of said biomarker prior to anti-MAdCAM treatment, or certain time points during treatment, or a predetermined value.

Subsequent doses may also be administered during biomarker assessment. For example, anti-MAdCAM antagonist antibody may be administered every 4 weeks, and the biological samples may be taken at 4 week, 8 week, and 12 week after initial dose. In some aspects, the methods of the invention provide for a reduction in Fecal Calprotectin about 12 weeks after the initial dose, of at least about 20%. In some aspects, the methods of the invention provide for a reduction in Fecal Calprotectin about 12 weeks after the initial dose, of at least about 25%. In some aspects, the methods of the invention provide for a reduction in Fecal Calprotectin about 12 weeks after the initial dose, of at least about 30%. In some aspects, the methods of the invention provide for a reduction in Fecal Calprotectin about 12 weeks after the initial dose, of at least about 35%. In some aspects, the methods of the invention provide for a reduction in Fecal Calprotectin about 12 weeks after the initial dose, of at least about 40%. In some aspects, the methods of the invention provide for a reduction in Fecal Calprotectin about 12 weeks after the initial dose, of at least about 45%. In some aspects, the methods of the invention provide for a reduction in Fecal Calprotectin about 12 weeks after the initial dose, of at least about 50%. In some aspects, the methods of the invention provide for a reduction in Fecal Calprotectin about 12 weeks after the initial dose, of at least about 55%. The foregoing % values may be as compared against a control (such as the pre-treatment Fecal Calprotectin level). In some aspects, the methods of the invention provide for a reduction in Fecal Calprotectin about 12 weeks after the initial dose, of at least about 60%, of at least about 65%, of at least about 70%, of at least about 75%, of at least about 80%, of at least about 85%, of at least about 90%, or of at least about 95%, as compared to a control (such as the pre-treatment Fecal Calprotectin level).

In some aspects, the methods of the invention provide for a reduction in sMAdCAM about 12 weeks after the initial dose. In some aspects, the methods of the invention provide for a reduction in sMAdCAM about 12 weeks after the initial dose, of at least about 25%. In some aspects, the methods of the invention provide for a reduction in sMAdCAM about 12 weeks after the initial dose, of at least about 50%. In some aspects, the methods of the invention provide for a reduction in sMAdCAM about 12 weeks after the initial dose, of at least about 60%. In some aspects, the methods of the invention provide for a reduction in sMAdCAM about 12 weeks after the initial dose, of at least about 65%. In some aspects, the methods of the invention provide for a reduction in sMAdCAM about 12 weeks after the initial dose, of at least about 70%. In some aspects, the methods of the invention provide for a reduction in sMAdCAM about 12 weeks after the initial dose, of at least about 75%. In some aspects, the methods of the invention provide for a reduction in sMAdCAM about 12 weeks after the initial dose, of at least about 80%. In some aspects, the methods of the invention provide for a reduction in sMAdCAM about 12 weeks after the initial dose, of at least about 85%. In some aspects, the methods of the invention provide for a reduction in sMAdCAM about 12 weeks after the initial dose, of at least about 90%. The foregoing % values may be as compared against a control (such as the pre-treatment sMAdCAM level). In some aspects, the methods of the invention provide for a reduction in sMAdCAM about 12 weeks after the initial dose, of at least about 95%, as compared to a control (such as the pre-treatment sMAdCAM level).

In some aspects, the methods of the invention provide for a reduction in hsCRP about 12 weeks after the initial dose. In some aspects, the methods of the invention provide for a reduction in hsCRP about 12 weeks after the initial dose, of at least about 5%. In some aspects, the methods of the invention provide for a reduction in hsCRP about 12 weeks after the initial dose, of at least about 10%. In some aspects, the methods of the invention provide for a reduction in hsCRP about 12 weeks after the initial dose, of at least about 15%. In some aspects, the methods of the invention provide for a reduction in hsCRP about 12 weeks after the initial dose, of at least about 65%. In some aspects, the methods of the invention provide for a reduction in hsCRP about 12 weeks after the initial dose, of at least about 16%. In some aspects, the methods of the invention provide for a reduction in hsCRP about 12 weeks after the initial dose, of at least about 20%. The foregoing % values may be as compared against a control such as the pre-treatment hsCRP level. In some aspects, the methods of the invention provide for a reduction in hsCRP about 12 weeks after the initial dose, of at least about 25%, of at least about 30%, of at least about 35%, of at least about 40%, of at least about 45%, of at least about 50%, of at least about 55%, of at least about 60%, of at least about 65%, of at least about 70%, of at least about 75%, of at least about 80%, of at least about 85%, of at least about 90%, or of at least about 95%, as compared to a control (such as the pre-treatment hsCRP level).

In some aspects, the methods of the invention provide for an increase in CCR9 RNA transcript about 12 weeks after the initial dose. In some aspects, the methods of the invention provide for an increase in CCR9 RNA transcript about 12 weeks after the initial dose, of at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2.0 fold, at least about 2.1 fold, at least about 2.2 fold, at least about 2.3 fold, at least about 2.4 fold, at least about 2.5 fold, at least about 3.0 fold, at least about 3.5 fold, at least about 4.0 fold, at least about 4.5 fold, at least about 5.0 fold, at least about 5.5 fold, at least about 6.0 fold, at least about 6.5 fold, at least about 7.0 fold, at least about 7.5 fold, at least about 8.0 fold, at least about 8.5 fold, at least about 9.0 fold, at least about 9.5 fold, or at least about 10.0 fold, as compared to a control (such as the pre-treatment CCR9 level).

In some aspects, the methods of the invention provide for an increase in circulating $\alpha 4\beta 7+$ cells about 12 weeks after the initial dose. In some aspects, the methods of the invention provide for an increase in circulating $\alpha 4\beta 7+$ cells about 12 weeks after the initial dose, of at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2.0 fold, at least about 2.1 fold, at least about 2.2 fold, at least about 2.3 fold, at least about 2.4 fold, at least about 2.5 fold, at least about 3.0 fold, at least about 3.5 fold, at least about 4.0 fold, at least about 4.5 fold, at least about 5.0 fold, at least about 5.5 fold, at least about 6.0 fold, at least about 6.5 fold, at least about 7.0 fold, at least about 7.5 fold, at least about 8.0 fold, at least about 8.5 fold, at least about 9.0 fold, at least about 9.5 fold, or at least about 10.0 fold, as compared to a control (such as the pre-treatment circulating $\alpha 4\beta 7+$ cell level).

In certain aspect, the patient receiving treatment of a MAdCAM antagonist antibody comprises heterozygote rs11171739 risk allele (C;T). In certain aspect, the patient receiving treatment of a MAdCAM antagonist antibody comprises homozygote rs11171739 risk allele (C;C).

Any combination of the above disclosed changes are also encompassed by the invention. For example, to evaluate the presence of a beneficial response to anti-MAdCAM treatment, or to select a sub-population of patient, one may combine 50% decrease in sMAdCAM and 2-fold increase in CCR9 transcript as a criterion.

Articles of Manufacture

The invention further provides for an article of manufacture, comprising a container, a composition within the container comprising a MAdCAM antagonist antibody, and a package insert containing instructions to dose the antibody according the methods and uses described herein.

The invention also concerns a MAdCAM antagonist antibody, or antigen binding portion thereof, for use as a medicament.

The invention also relates to a MAdCAM antagonist antibody, or antigen binding portion thereof, for use as a medicament.

Dosage Intervals

In some aspects, the methods of the invention further provide for the administration of subsequent doses of the antibody in an amount that is approximately the same or less than the initial dose.

In some aspects, the first subsequent dose is provided between about 2 and about 12 weeks after the first dose. In some aspects, the first subsequent dose is provided about 4 weeks after the first dose.

In some aspects, the subsequent doses are given between about 4 and about 12 weeks apart. In some aspects, the subsequent doses are given between about 2 and about 8 weeks apart. In some aspects, the subsequent doses are given between about 2 and about 10 weeks apart. In some aspects, the subsequent doses are given between about 4 and about 10 weeks apart. In some aspects, the subsequent doses are given about 4 weeks apart.

In some aspects, the subsequent doses are given between about 1 and about 3 months apart. In some aspects, the subsequent doses are given about 1 month apart. In some aspects, the subsequent doses are given about 2 months apart.

In some aspects, the methods of the invention further provide for the administration of a maintenance dose of the antibody in an amount that is approximately the same or less than the initial dose, provided between the first and the first subsequent dose(s).

The antibody may be administered once, or may be administered multiple times.

In some aspects, the invention provides for a method of use of a MAdCAM antagonist antibody, a pharmaceutical composition comprising a MAdCAM antagonist antibody for treating a patient, wherein the MAdCAM antagonist antibody dose provided to a patient is sufficient for sustained reduction of MAdCAM levels over a period of at least about 1, at least about 2, at least about 3, at least about 4, at least about 5, at least about 6, at least about 7, at least about 8 weeks, at least about 9, at least about 10, at least about 11, at least about 12 weeks after administration, together with a pharmaceutically acceptable excipient or carrier.

In some aspects, the initial dosage is between whose lower limit is selected from the group consisting of about 5 mg, 6 mg, about 7 mg, about 7.5 mg, about 8 mg, about 9 mg, about 10 mg, about 12 mg, about 15 mg, about 20 mg, about 22.5 mg, about 25 mg, about 30 mg, about 35 mg, about 45 mg, about 50 mg, and whose upper limit is selected from the group consisting of about 50 mg, about 55 mg, about 60 mg, about 65 mg, about 70 mg, less than about 75 mg, and about 75 mg, and the subsequent dosage is delivered in an amount that is about the same or less than the initial dose, and the subsequent dose is administered between about 2 and about 6 weeks after the initial dose. In some aspects, the subsequent dose is administered about 4 weeks after the initial dose.

In some aspects, the initial dosage is between whose lower limit is selected from the group consisting of about 50 mg, about 55 mg, about 60 mg, about 65 mg about 70 mg, about 75 mg, about 80 mg, about 85 mg, about 90 mg about 95 mg, and about 100 mg, and whose upper limit is selected from the group consisting of about 75 mg, about 80 mg, about 85 mg, about 90 mg, about 95 mg, about 100 mg, about 105 mg, about 110 mg, about 115 mg, about 120 mg, 125 mg, about 130 mg, about 135 mg, about 140 mg, about 145 mg, less than about 150 mg, and about 150 mg, and the subsequent dosage is delivered in an amount that is about the same or less than the initial dose, and the subsequent dose is administered between about 6 and about 10 weeks after the initial dose. In some aspects, the subsequent dose is administered about 8 weeks after the initial dose.

Administration Route

Accordingly, the present invention provides a method for the treatment of a patient susceptible to diagnosed with a disorder characterized by overexpression of MAdCAM, comprising administering an initial dose of a therapeutically effective amount of MAdCAM antagonist antibody subcutaneously.

In some aspects, the present invention provides a method for the treatment of a patient susceptible to diagnosed with a disorder characterized by overexpression of MAdCAM, comprising administering an initial dose of a therapeutically effective amount of MAdCAM antagonist antibody intravenously.

In some aspects, the at least one subsequent dose are administered by subcutaneous injection. In some aspects, the at least one subsequent dose are administered by intravenous injection.

The antibody may also be administered continuously via a minipump. The antibody may be administered via a mucosal, buccal, intranasal, inhalable, intravenous, subcutaneous, intramuscular, parenteral, or intratumor route. The antibody may be administered once, at least twice or for at least the period of time until the condition is treated, palliated or cured. The antibody generally will be administered for as long as the condition is present.

MAdCAM Antibodies of the Invention

The invention relates to MAdCAM antibodies in general and their use. In some aspects, the antibody is mAb 7.16.6, or a variant thereof. In some aspects, the MAdCAM antagonist antibody comprises the CDRs of SEQ ID NO:1 and SEQ ID NO:2. In some aspects, the MAdCAM antagonist antibody comprises the CDRs of SEQ ID NO:3 and SEQ ID NO:4. In some aspects, the MAdCAM antagonist antibody comprises the variable domains of SEQ ID NO:3 and SEQ ID NO:4. In some aspects, the MAdCAM antagonist antibody comprises SEQ ID NO:1 and SEQ ID NO:2. In some aspects, alternative MAdCAM antagonist antibodies for use in methods and compositions of the invention may be used. Exemplary MAdCAM antagonist antibodies are listed in Table 1 and 2. The examples of WO2005067620 (herein incorporated by reference) describe fully the antibodies of Tables 1 and 2, and provide details of characterizing information such as binding affinities, $K_{on}$, $K_{off}$, $K_d$, and so on.

In some aspects, the antibody may be a MAdCAM antagonist antibody that cross competes with mAb 7.16.6 (SEQ ID NO:1 and 2).

In some aspects, the antibodies of the invention have one or more of the following characteristics:
 a half-life in human patients of between 20 and 60 days;
 SC bioavailability of at least 50%; and/or
 a $K_D$ of ≤10 nM.

In some aspects, the antibody may have a half-life in human patients of at least 30 days. In some aspects, the antibody may have a half-life in human patients of at least 35 days. In some aspects, the antibody may have a half-life in human patients of at least 40 days. In some aspects, the antibody may have a half-life in human patients of at least 45 days. In some aspects, the antibody may have a half-life in human patients of at least 50 days.

In some aspects, the antibody's SC bioavailability may be at least 60%. In some aspects, the antibody's SC bioavailabity may be at least 65%. In some aspects, the antibody's SC bioavailabity may be at least 70%. In some aspects, the antibody's SC bioavailabity may be at least 75%. In some aspects, the antibody's SC bioavailability may be at least 80%. In some aspects, the antibody's SC bioavailability may be at least 85%. In some aspects, the antibody's SC bioavailability may be at least 90%. In some aspects, the antibody's SC bioavailability may be at least 95%. In some aspects, the antibody's SC bioavailability may be at least 90%. In some aspects, the antibody's SC bioavailabity may be at least 99%.

In some aspects, the KD is measured by surface plasmon resonance. In some aspects, surface plasmon resonance may be measured using a Biocore. In some aspects, the SPR may be measured using Biacore with captured antibody and solution phase MAdCAM.

In some aspects, the antibody has a KD of ≤10 nM. In some aspects, the antibody has a KD of ≤1 nM. In some aspects, the antibody has a KD of ≤500 pM. In some aspects, the antibody has a KD of ≤200 pM. In some aspects, the antibody has a KD of ≤100 pM. In some aspects, the antibody has a KD of ≤50 pM. In some aspects, the antibody has a KD of ≤20 pM. In some aspects, the antibody has a KD of ≤10 pM. In some aspects, the antibody has a KD of ≤5 pM.

DEPOSIT INFORMATION

Hybridomas were deposited under terms in accordance with the Budapest Treaty in the European Collection of Cell Cultures (ECACC), H.P.A at CAMR, Porton Down, Salisbury, Wiltshire SP4 OJG on 9 Sep. 2003 with the following deposit numbers.

TABLE 1

MAdCAM antagonist antibody deposits.

| Antibody | Light Chain SEQ ID NO: | Heavy Chain SEQ ID NO: | ECACC designation of hybridoma |
|---|---|---|---|
| 1.7.2 | 17 | 18 | 03090901 |
| 1.8.2 | 19 | 20 | 3090902 |
| 6.14.2 | 21 | 22 | 03090903 |
| 6.22.2 | 23 | 24 | 03090904 |
| 6.34.2 | 25 | 26 | 03090905 |
| 6.67.1 | 27 | 28 | 03090906 |
| 6.73.2 | 29 | 30 | 03090907 |
| 6.77.1 | 31 | 32 | 03090908 |
| 7.16.6 | 1 | 2 | 03090909 |
| 7.20.5 | 33 | 34 | 03090910 |
| 7.26.4 | 35 | 36 | 03090911 |
| 9.8.2 | 37 | 38 | 03090912 |

The deposits were made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ECACC under the terms of the Budapest Treaty, and subject to an agreement between Pfizer Inc. and ECACC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Therapeutic Methods of the Invention

Therapeutic methods are provided by the invention. A therapeutic method comprises administering a compound or composition of the invention to a subject in need thereof.

As used herein, an "effective dosage" or "effective amount" of drug, compound, or pharmaceutical composition is an amount sufficient to affect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

"Therapeutically effective amount" refers to that amount of the therapeutic agent being administered which will relieve to some extent one or more of the symptoms of the disorder being treated.

"Treat", "treating" and "treatment" refer to a method of alleviating or abrogating a biological disorder and/or its attendant symptoms.

An "individual" or a "subject" is a mammal, more preferably, a human. Mammals also include, but are not limited to, farm animals, sport animals, pets, primates, and horses. In some aspects, the patient is a human patient.

Also provided are methods for inhibiting MAdCAM activity by administering a MAdCAM antagonist antibody to a patient in need thereof. Any of the antibodies or antigen-binding portions thereof described herein may be used therapeutically. In a preferred embodiment, the MAdCAM antagonist antibody is a human, chimeric or humanized antibody. In another preferred embodiment, the MAdCAM is human and the patient is a patient. Alternatively, the patient may be a mammal that expresses a MAdCAM that the MAdCAM antagonist antibody cross-reacts with. The antibody may be administered to a non-human mammal expressing MAdCAM purposes or as an animal model of human disease. Such animal models may be used for demonstrating the therapeutic efficacy of the antibodies.

In some aspects, a MAdCAM antagonist antibody or antibody portion thereof may be administered to a patient who expresses abnormally high levels of MAdCAM. The MAdCAM antibodies or antigen-binding portions thereof can be used to treat diseases in which MAdCAM is implicated. Examples of diseases that can be treated using the MAdCAM antibodies or antigen binding portions thereof include ulcerative colitis (UC), Crohn's disease (CD), Irritable bowel syndrome (IBS), irritable bowel disease (IBD), Celiac disease, primary sclerosing cholangitis, biliary disease, rheumatoid arthritis, reactive arthritis, osteoarthritis, infectious arthritis, psoriatic arthritis, polyarthritis, juvenile arthritis, juvenile rheumatoid arthritis, juvenile reactive arthritis, juvenile psioriatic arthritis, pain, fibrosis, fibromyalgia syndrome, ankylosing spondylitis, undifferentiated spondyloarthropathy, juvenile onset spondylarthritis, psoriasis, gout, Castleman's disease, adult-onset Still's disease, sepsis, type I diabetes, type II diabetes, multiple myeloma, and renal cell carcinoma. The MAdCAM antibodies or antigen-binding portions thereof can be used to treat UC.

MAdCAM antibodies or antigen-binding portions thereof can be used in combination with one or more other therapeutic agents. For example, an antibody or antigen-binding portions thereof can be used with a COX-2 inhibitor, such as celecoxib, for the treatment of diseases such as rheumatoid arthritis, osteoarthritis and pain. MAdCAM antibodies or antigen-binding portions thereof and the other therapeutic agents can be administered to the patient in the same dosage form or in different dosage forms. Moreover, they can be administered at the same time or at different times. Below are some examples of the diseases and their therapeutic agents that can be used in combination with anti-MAdCAM antibodies or antigen-binding portions thereof.

Ulcerative Colitis

In some aspects, the invention provides for compositions and methods for the treatment of ulcerative colitis. In some aspects, the compositions and methods of the invention provide for the use of a MAdCAM antagonist antibody in combination with one or more other additional therapeutic agents.

In some aspects, the one or more additional therapeutic agent may be selected from the group consisting of acetaminophen, naproxen sodium, ibuprofen, tramadol, aspirin, celecoxib, valdecoxib, indomethacin, and other NSAIDs. In some aspects, the one or more additional therapeutic agent may be selected from the group consisting of beclomethasone, hydroxycortisone, betamethasone, methylprednisolone, budesonide, prednisolone. cortisone, prednisone, dexamethasone, and triamcinolone, and other glucorticoids. In some aspects, the one or more additional therapeutic agent may be selected from the group consisting of 6-mercaptopurine, tacrolimus, azathioprine, thalidomide, cyclosporine, tofacitinib, methotrexate, and other immunosuppressants/immunomodulators. In some aspects, the one or more additional therapeutic agent may be selected from the group consisting of abatacept, etrolizumab, adalimumab, golimumab, AMG-181, infliximab, anti-ip-10 antibody, interleukin-2, AVX 470, vedolizumab, certolizumab pegol, and other biologics. In some aspects, the one or more additional therapeutic agent may be selected from the group consisting of AEB-071, melatonin, alicaforsam, mesalamine, benzothiazinone, nicotine, *cannabis*, phosphatidyl choline, curcurmin, stem cells, hmpl-004, sulfasalazine, iberogast, *trichuris suis*, kappaproct, krp-203, sulfasalazine, mesalamine, balsalazide, olsalazine; and loperamide.

Accordingly, in some aspects, the compositions and methods of the invention are specifically intended for use in combination with these agents, products and classes.

Crohn's Disease

In some aspects, the invention provides for compositions and methods for the treatment of Crohn's disease.

Products: analgesics such as acetaminophen, naproxen sodium, ibuprofen, tramadol, aspirin, celecoxib, valdecoxib, indomethacin, and other NSAIDs; anti-inflammatory drugs; sulfasalazine, mesalamine, balsalazide, and olsalazine; and corticosteroids such as prednisone and budesonide; immunosuppressant drugs such as azathioprine, mercaptopurine, TNF blockers such as infliximab and adalimumab, methotrexate, and cyclosporine; antibiotics such as metronidazole and ciprofloxacin; anti-diarrheals such as loperamide; and laxatives. Classes: analgesics; NSAIDs; COX-2 inhibitors; anti-inflammatory drugs; TNF blockers; antibiotics; anti-diarrheals; and laxatives.

Accordingly, in some aspects, the compositions and methods of the invention are specifically intended for use in combination with these products and classes.

Other Indications

In some aspects, the invention provides for compositions and methods for the treatment of Rheumatoid arthritis (RA), Reiter's syndrome (reactive arthritis), osteoarthritis, infectious arthritis, psioratic arthritis, polyarthritis, juvenile arthritis, juvenile rheumatoid arthritis, juvenile reactive arthritis, juvenile psoriatic arthritis, pain, fibrosis, fibromyalgia syndrome, ankylosing spondylitis, undifferentiated spondyloarthropathy (USpA), juvenile-onset spondyloarthritis (JSpA), psoriasis, gout, or Irritable bowel syndrome (IBS).

Other diseases are associated with high levels of MAdCAM may also be treated with methods and compounds of the invention, such as treatment-resistant depression, cancer cachexia, type-II diabetes, Takayasu's arteritis, Grave's ophthalmopathy, and muscle wasting in the elderly.

Pharmaceutical Compositions and Administration

Also provided are pharmaceutical compositions for the treatment a condition associated with an increase in MAdCAM expression in a mammal (such as ulcerative colitis, Crohn's disease), including a human, comprising an amount of a MAdCAM antagonist antibody or antigen binding portion thereof, as described herein, that is effective in treating abnormal cell infiltration, and a pharmaceutically acceptable carrier. The compositions provide a therapeutic benefit to patients with one of more of a variety of inflammatory and autoimmune diseases, such as rheumatoid arthritis, atherosclerosis, granulomatous diseases, multiple sclerosis, asthma and cancer.

MAdCAM antibodies and antigen-binding portions thereof can be incorporated into pharmaceutical compositions suitable for administration to a subject. Typically, the pharmaceutical composition comprises a MAdCAM antagonist antibody or antigen-binding portion thereof and a pharmaceutically acceptable carrier. As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The compositions of this invention may be in a variety of forms, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application. Typical compositions are in the form of injectable or infusible solutions, such as compositions similar to those used for passive immunization of humans. In one case the mode of administration is parenteral (e.g., intravenous, subcutaneous, intraperitoneal, intramuscular). In another case, the antibody is administered by intravenous infusion or injection. In another case, the antibody is administered by intramuscular or subcutaneous injection. Formulations for injection may be presented in unit dosage form, e.g., in ampoules or in multi-dose containers, with or without an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. Sterile injectable solutions can be prepared by incorporating the MAdCAM antagonist antibody in the required amount in an appropriate solvent with one or a combination of ingredients enumerated above, as required, followed by filter sterilization.

Dosage values may vary with the type and severity of the condition to be alleviated. In the case of sterile powders for the preparation of sterile injectable solutions, the suitable methods of preparation include vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain cases, the MAdCAM antagonist antibody compositions may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations may be used. See, e.g., Sustained and Controlled Release Drug Delivery Systems, J. R. Robinson, ed., Marcel Dekker, Inc., New York, 1978, which is incorporated herein by reference.

Additional active compounds also can be incorporated into the compositions (including any one or more of the previously disclosed additional therapeutic agents). In some cases, an inhibitory MAdCAM antagonist antibody is co-formulated with and/or co-administered with one or more additional therapeutic agents. These agents include, without limitation, antibodies that bind other targets, anti-tumor agents, anti-angiogenesis agents, signal transduction inhibitors, anti-proliferative agents, chemotherapeutic agents, or peptide analogues that inhibit MAdCAM. Such combination therapies may require lower dosages of the inhibitory MAdCAM antagonist antibody as well as the co-administered agents, thus avoiding possible toxicities or complications associated with the various monotherapies.

The compositions may include a "therapeutically effective amount" or a "prophylactically effective amount" of an antibody or antigen-binding portion. A "therapeutically effective amount" refers to an amount effective, at dosages and for periods of time necessary, to achieve the desired therapeutic result. A therapeutically effective amount of the antibody or antigen-binding portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antigen-binding portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

In one case, the antibody is administered in a formulation as a sterile aqueous solution having a pH that ranges from about 5.0 to about 6.5 and comprising from about 1 mg/ml to about 200 mg/ml of antibody, from about 1 millimolar to about 100 millimolar of histidine buffer, from about 0.01 mg/ml to about 10 mg/ml of polysorbate 80 or polysorbate 20, from about 100 millimolar to about 400 millimolar of a non-reducing sugar selected from but not limited to trehalose or sucrose, from about 0.01 millimolar to about 1.0 millimolar of disodium EDTA dihydrate and optionally comprise a pharmaceutically acceptable antioxidant in addition to a chelating agent. Suitable antioxidants include, but are not limited to, methionine, sodium thiosulfate, catalase, and platinum. For example, the composition may contain methionine in a concentration that ranges from 1 mM to about 100 mM, and in particular, is about 27 mM. In some cases, a formulation contains 5 mg/ml of antibody in a buffer of 20 mM sodium citrate, pH 5.5, 140 mM NaCl, and 0.2 mg/ml polysorbate 80.

In some aspects, the formulation is as set forth in WO2006/096490, the contents of which are hereby incorporated. In some aspects, the formulation comprises 75 mg/ml antibody, 10 mM histidine pH 5.5, 90 mg/ml trehalose, dihydrate, 0.1 mg/ml disodium EDTA dihydrate, and 0.4 mg/ml polysorbate 80.

In another aspect, the formulation comprises: 20 mM histidine, 7% Trehalose, 0.4 mg/mL polysorbate 80, 0.1 mg/mL EDTA, pH 5.5, and 25 mg/mL and 75 mg/mL anti-MAdCAM antibody.

Kits

Another aspect provided herein are kits comprising a MAdCAM antagonist antibody or antigen-binding portion or a composition comprising such an antibody or antigen-binding portion. A kit may include, in addition to the antibody or composition, or one or more additional therapeutic agents, and or one or more additional diagnostic agents. A kit can also include instructions for use in a diagnostic or therapeutic method. In one case, the kit includes the antibody or a composition comprising the antibody and a diagnostic agent that can be used in a method described herein. In another case, the kit includes the antibody or a composition comprising it and one or more therapeutic agents that can be used in a method described herein.

In some aspects, the invention provides an article of manufacture, comprising a container, a composition within the container comprising a MAdCAM antagonist antibody, and a package insert containing instructions according to a method of the invention. Another aspect provided herein are kits comprising a probe for detecting or quantifying a biomarker described herein. Said kits can be used to assess the presence or absence of a beneficial response to anti-MAdCAM treatment. The kits are useful for determining whether a patient should continue with anti-MAdCAM treatment, identifying a sub-population of patients who are likely to benefit from anti-MAdCAM treatment, or adjusting the dose of anti-MAdCAM antagonist antibody.

Definitions

Antibodies

An "Antibody" is an immunoglobulin molecule capable of specific binding to a target or antigen, such as a carbohydrate, polynucleotide, lipid, polypeptide, etc., through at least one antigen-binding site, located in the variable region of the immunoglobulin molecule.

As used herein, unless otherwise indicated by context, the term is intended to encompass not only intact polyclonal or monoclonal antibodies comprising two identical full-length heavy chain polypeptides and two identical light chain polypeptides, but also fragments thereof (such as Fab, Fab', F(ab')2, Fv), single chain (ScFv) and domain antibodies (dAbs), including shark and camelid antibodies, and fusion proteins comprising an antibody portion, multivalent antibodies, multispecific antibodies (e.g. bispecific antibodies so long as they exhibit the desired biological activity) and antibody fragments as described herein, and any other modified configuration of the immunoglobulin molecule that comprises an antigen recognition site, for example without limitation, minibodies, maxibodies, monobodies, peptibodies, intrabodies, diabodies, triabodies, tetrabodies, v-NAR and bis-scFv.

Antigen-binding portions may be produced by recombinant DNA techniques or by enzymatic or chemical cleavage of intact antibodies. Antigen-binding portions include, inter alia, Fab, Fab', F(ab')2, Fv, dAb, and complementarity determining region (CDR) fragments, single-chain antibodies (scFv), chimeric antibodies, diabodies and polypeptides that contain at least a portion of an Ig that is sufficient to confer specific antigen binding to the polypeptide.

An immunoglobulin (Ig) is a heteromultimeric molecule. In a naturally occurring Ig, each multimer is composed primarily of identical pairs of polypeptide chains, each pair having one "light" (about 25 kDa) and one "heavy" chain (about 50-70 kDa).

The amino-terminal portion of each chain includes a variable region, of about 100 to 110 or more amino acids primarily responsible for antigen recognition. The carboxy-terminal portion of each chain defines a constant region primarily responsible for effector function. Human light chains are classified as κ and λ light chains. Heavy chains are classified as α, δ, ε, γ, and μ, and define the antibody's isotype as IgA, IgD, IgE, IgG, IgM, respectively. Several of these classes may be further subdivided into isotypes: IgG1, IgG2, IgG3, IgG4, IgA1, and IgA2.

Within light and heavy chains, the variable and constant regions are joined by a "J" region of about 12 or more amino acids, with the heavy chain also including a "D" region of about 10 more amino acids (in the context of an entire antibody sequence, the D and J regions are sometimes considered as parts of the variable region after they have been joined). The variable regions of each light/heavy chain pair form the antibody binding site such that an intact Ig has 2 binding sites.

Variable domains exhibit the same general structure of relatively conserved framework regions (FR) joined by 3 hypervariable regions, also called complementarity determining regions or CDRs. The CDRs from the 2 chains of each pair are aligned by the framework regions, enabling binding to a specific epitope. From N-terminus to C-terminus, both light and heavy chains comprise the domains FR1, CDR1, FR2, CDR2, FR3, CDR3 and FR4.

The identity of the amino acid residues in a particular antibody that make up a CDR can be determined using methods well known in the art. For example, antibody CDRs may be identified as the hypervariable regions originally defined by Kabat et al (Kabat et al., 1991, Sequences of Proteins of Immunological Interest, 5th ed., Public Health Service, NIH, Washington D.C., NIH Publication No. 91-3242). The positions of the CDRs may also be identified as the structural loop structures described by Chothia and others (Chothia et al., 1989, Nature 342:877-883). Other approaches to CDR identification include the "AbM definition," which is a compromise between Kabat and Chothia and is derived the Abysis program (www.abysis.org), or the "contact definition" of CDRs based on observed antigen contacts, set forth in MacCallum et al., 1996, J. Mol. Biol., 262:732-745. North has identified canonical CDR conformations using a different preferred set of CDR definitions (North et al., 2011, J. Mol. Biol, 406: 228-256). In another approach, referred to herein as the "conformational definition" of CDRs, the positions of the CDRs may be identified as the residues that make enthalpic contributions to antigen binding (Makabe et al., 2008, Journal of Biological Chemistry, 283:1156-1166). Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs (or other residue of the antibody) may be defined in accordance with any of Kabat, Chothia, North, extended, AbM, contact, and/or conformational definitions.

Mammalian light chains are of two types, K and A, and in any given naturally occurring antibody molecule only one type occurs. Approximately twice as many K as A molecules are produced in humans but in other mammals this ratio can vary. Each free light chain molecule contains approximately 220 amino acids in a single polypeptide chain that is folded to form the constant and variable region domains.

Constant kappa ($CL_K$) regions are encoded by a single gene, whereas lambda constant (CLλ) regions are encoded by multiple genes, and undergo splicing. Several markers associated with particular polymorphic species of CLλ are known: IgCLλ1 (Mcg marker); IgLC2
  IgCLλ2 (Kern-Oz-marker); IgCLλ 3 (Kern-Oz+ marker), and IgCLλ7, for example. The skilled person can easily establish all of the polymorphisms so far identified in human CLλ chains. The sequences of the present invention encompass other known polymorphisms of the $CL_K$ and CLλ, and antibodies in general. Two polymorphic loci have been identified in the $CL_K$; $CL_K$-V/A$^{153}$ and $CL_K$-L/V$^{191}$. The three polymorphisms so far identified are: Km(1): $CL_K$-V$^{153}$/L$^{191}$-Km(1,2): $CL_K$-A$^{153}$/L$^{191}$; and Km(3): $CL_K$-A$^{153}$/v$^{191}$.

The term "Fc region" as used herein generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. The Fc sequence of an immunoglobulin generally comprises two constant domains, a $C_H2$ domain and a $C_H3$ domain, and optionally comprises a $C_H4$ domain. The term "Fc polypeptide" is used herein to refer to one of the polypeptides that makes up an Fc region. In some embodiments, an Fc polypeptide may be obtained or derived from any suitable immunoglobulin, such as from at least one of the various IgG1, IgG2, IgG3, or IgG4 subtypes, or from IgA, IgE, IgD or IgM. In some embodiments, an Fc polypeptide comprises part or all of a wild-type hinge sequence (generally at its N terminus). In some embodiments, an Fc polypeptide does not comprise a wild-type hinge sequence. An Fc polypeptide may comprise native or variant Fc sequences.

The "immunoglobulin-like hinge region," "immunoglobulin-like hinge sequence," and variations thereof, as used herein, refer to the hinge region and hinge sequence of an immunoglobulin-like or an antibody-like molecule (e.g. immunoadhesins). In some embodiments, the immunoglobulin-like hinge region can be from or derived from any IgG1, IgG2, IgG3, or IgG4 subtype, or from IgA, IgE, IgD or IgM, including chimeric forms thereof, e.g. a chimeric IgG1/2 hinge region.

"Antibody fragments" comprise only a portion of an intact antibody, wherein the portion preferably retains at least one, preferably most or all, of the functions normally associated with that portion when present in an intact antibody.

A "bivalent antibody" comprises two antigen binding sites per molecule (e.g. IgG). In some instances, the two binding sites have the same antigen specificities. However, bivalent antibodies may be bispecific (see below).

A "monovalent antibody" comprises one antigen binding site per molecule (e.g. IgG). In some instances, a monovalent antibody can have more than one antigen binding site, but the binding sites are from different antigens.

A "multispecific antibody" is one that targets more than one antigen or epitope. A "bispecific," "dual-specific" or "bifunctional" antibody is a hybrid antibody having two different antigen binding sites. Bispecific antibodies are a species of multispecific antibody and may be produced by a variety of methods including, such as fusion of hybridomas or linking of Fab' fragments. See, e.g. Songsivilai and Lachmann (1990), Clin. Exp. Immunol. 79:315-321; and Kostelny et al. (1992), J. Immunol. 148:1547-1553. The two binding sites of a bispecific antibody will bind to two different epitopes, which may reside on the same or different protein targets.

The phrase "antigen binding arm," "target molecule binding arm," and variations thereof, as used herein, refers to a component part of an antibody of the invention that has an ability to specifically bind a target molecule of interest. Generally and preferably, the antigen binding arm is a complex of immunoglobulin polypeptide sequences, e.g. CDR and/or variable domain sequences of an immunoglobulin light and heavy chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Further, in contrast to polyclonal antibody preparations that typically include different antibodies directed against different determinants (epitopes), each monoclonal antibody is directed against a single determinant on the antigen.

A Fab fragment is a monovalent fragment consisting of the $V_L$, $V_H$, $C_L$ and $C_H1$ domains; a F(ab')2 fragment is a bivalent fragment comprising two Fab fragments linked by a disulfide bridge at the hinge region; a Fd fragment consists of the $V_H$ and $C_H1$ domains; an Fv fragment consists of the $V_L$ and $V_H$ domains of a single arm of an antibody; and a dAb fragment consists of a $V_H$ domain or a $V_L$ domain (e.g. human, camelid, or shark).

A single-chain antibody (scFv) is an antibody in which a VL and VH region are paired to form a monovalent molecule via a synthetic linker that enables them to be made as a single protein chain. Diabodies are bivalent, bispecific antibodies in which VH and VL domains are expressed on a single polypeptide chain, but using a linker that is too short to allow for pairing between the 2 domains on the same chain, thereby forcing the domains to pair with complementary domains of another chain and creating 2 antigen binding sites. One or more CDRs may be incorporated into a molecule either covalently or noncovalently to make it an immunoadhesin. An immunoadhesin may incorporate the CDR (s) as part of a larger polypeptide chain, may covalently link the CDR (s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring antibody has 2 identical binding sites, a single-chain antibody or Fab fragment has one binding site, while a "bispecific" or "bifunctional" antibody has 2 different binding sites.

An "isolated antibody" is an antibody that (1) is not associated with naturally-associated components, including other naturally-associated antibodies, that accompany it in its native state, (2) is free of other proteins from the same species, (3) is expressed by a cell that does not naturally express the antibody, or is expressed by a cell from a different species, or (4) does not occur in nature.

The term "human antibody" includes all antibodies that have one or more variable and constant regions derived from human Ig sequences. In some embodiments of the present invention, all of the variable and constant domains of the antibody are derived from human Ig sequences (a fully human antibody).

A humanized antibody is an antibody that is derived from a non-human species, in which certain amino acids have been mutated so as to avoid or abrogate an immune response in humans. Alternatively, a humanized antibody may be produced by fusing the constant domains from a human antibody to the variable domains of a non-human species.

The term "chimeric antibody" refers to an antibody that contains one or more regions from one antibody and one or more regions from one or more other antibodies. Each antibody may originate from separate species (such as human and mouse).

The term "epitope" includes any molecular determinant capable of specific binding to an Ig or T-cell receptor. Epitopic determinants usually consist of surface groupings of atoms such as amino acids or sugar side chains and usually have specific 3 dimensional structural characteristics, as well as specific charge characteristics. An antibody "specifically" binds an antigen when the dissociation constant is <1 uM, preferably <100 nM, or <10 nM.

Fully human antibodies are expected to minimize the immunogenic and allergic responses intrinsic to mouse or mouse-derivatized monoclonal antibodies (Mabs) and thus to increase the efficacy and safety of the administered antibodies. The use of fully human antibodies can be expected to provide a substantial advantage in the treatment of chronic and recurring human diseases, such as inflammation and cancer, which may require repeated antibody administrations.

In addition, fusion antibodies can be created in which 2 (or more) single-chain antibodies are linked to one another. This is useful if one wants to create a divalent or polyvalent antibody on a single polypeptide chain, or if one wants to create a bispecific antibody.

One type of derivatized antibody is produced by cross-linking 2 or more antibodies (of the same type or of different types; e. g. to create bispecific antibodies). Suitable cross-linkers include those that are heterobifunctional, having 2 distinctly reactive groups separated by an appropriate spacer (e. g., m-maleimidobenzoyl-N-hydroxysuccinimide ester) or homobifunctional (e. g. disuccinimidyl suberate).

Another type of derivatized antibody is a labelled antibody. Useful detection agents with which an antibody or antibody portion of the invention may be derivatized include fluorescent compounds, including fluorescein, fluorescein isothiocyanate, rhodamine, 5-dimethylamine-1-napthalene-sulfonyl chloride, phycoerythrin, lanthanide phosphors and the like. An antibody may also be labelled with enzymes that are useful for detection, such as horseradish peroxidase, galactosidase, luciferase, alkaline phosphatase, glucose oxidase and the like. An antibody may also be labelled with biotin, and detected through indirect measurement of avidin or streptavidin binding. An antibody may be labelled with a magnetic agent, such as gadolinium. An antibody may also be labelled with a predetermined polypeptide epitope recognized by a secondary reporter (e. g. leucine zipper pair sequences, binding sites for secondary antibodies, metal binding domains, epitope tags). In some embodiments, labels are attached by spacer arms of various lengths to reduce potential steric hindrance.

As used herein, a "full antagonist" is an antagonist which, at an effective concentration, essentially completely blocks a measurable effect of MAdCAM. By a partial antagonist is meant an antagonist that is capable of partially blocking a measurable effect, but that, even at a highest concentration is not a full antagonist. By essentially completely is meant at least about 80%, preferably, at least about 90%, more preferably, at least about 95%, and most preferably, at least about 98% or 99% of the measurable effect is blocked.

As used herein, an "anti-MAdCAM antagonist antibody" or "MAdCAM antagonist antibody" refers to a MAdCAM antagonist antibody that is able to inhibit MAdCAM biological activity and/or downstream pathway(s) mediated by MAdCAM signaling. A MAdCAM antagonist antibody encompasses antibodies that block, antagonize, suppress or reduce (to any degree including significantly) MAdCAM biological activity, including downstream pathways mediated by MAdCAM signaling, or elicitation of a cellular response to MAdCAM. For purpose of the present invention, it will be explicitly understood that the term "MAdCAM antagonist antibody" encompasses all the previously identified terms, titles, and functional states and characteristics whereby the MAdCAM itself, a MAdCAM biological activity, or the consequences of the biological activity, are substantially nullified, decreased, or neutralized in any meaningful degree. In some embodiments, a MAdCAM antagonist antibody binds MAdCAM. Examples of MAdCAM antagonist antibodies are provided in, e.g., WO2005067620, which is herein incorporated by reference in its entirety.

General Terms

As used herein, "biological activity" refers to the in vivo activities of a compound, composition, or mixture, or physiological responses that result upon in vivo administration of a compound, composition or other mixture. Biological activity encompasses therapeutic effects, diagnostic effects and pharmaceutical activity of such compounds, compositions, and mixtures.

The term "biologically compatible" as used herein means something that is biologically inert or non-reactive with intracellular and extra cellular biological molecules, and non-toxic.

"About" or "approximately," when used in connection with a measurable numerical variable, refers to the indicated value of the variable and to all values of the variable that are within the experimental error of the indicated value (e.g. within the 95% confidence interval for the mean) or within 10 percent of the indicated value, whichever is greater. Numeric ranges are inclusive of the numbers defining the range. Where the term "about" is used within the context of a time period (years, months, weeks, days etc.), the term "about" means that period of time plus or minus one amount of the next subordinate time period (e.g. about 1 year means 11-13 months; about 6 months means 6 months plus or minus 1 week; about 1 week means 6-8 days; etc.), or within 10 percent of the indicated value, whichever is greater.

The term "compete" means that a first antibody, or an antigen-binding portion thereof, competes for binding with a second antibody, or an antigen-binding portion thereof, where binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies can be useful for the methods disclosed herein.

The term "identity," as known in the art, refers to a relationship between the sequences of two or more polypeptide molecules or two or more nucleic acid molecules, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model of computer programs (i. e. "algorithms").

The term "similarity" is a related concept, but in contrast to "identity", refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10 out of 20 identical amino acids, and the remainder are all nonconservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

The term "conservative amino acid substitution" refers to a substitution of a native amino acid residue with a nonnative residue such that there is little or no effect on the polarity, charge, and approximate volume of the amino acid residue at that position. For example, a conservative substitution results from the replacement of a non-polar residue in a polypeptide with any other non-polar residue. The term may also refer to a substitution identified as frequently occurring between highly similar proteins, as in the BLOSUM62 matrix or related matrices (Proc. Natl. Acad. Sci. USA 89(22), 10915-9, 1992).

A reference to a nucleotide sequence as used herein encompasses its complement unless otherwise specified. Thus, a reference to a nucleic acid having a particular sequence should be understood to encompass its complementary strand, with its complementary sequence, unless otherwise defined by context.

The term "purify," and grammatical variations thereof, is used to mean the removal, whether completely or partially, of at least one impurity from a mixture containing the polypeptide and one or more impurities, which thereby improves the level of purity of the polypeptide in the composition (i.e. by decreasing the amount (ppm) of impurity(ies) in the composition).

The term "$K_D$" refers to the binding affinity equilibrium constant of a particular antibody-antigen interaction. An antibody is said to specifically bind an antigen when the $K_D$ is 1 mM, preferably ≤100 nM, and most preferably s 10 nM. A $K_D$ binding affinity constant can be measured by surface plasmon resonance (SPR), for example using the BIACORE™ system. In some aspects, the SPR used a captured antibody, and solution phase target. In some aspects, the SPR used a captured target, and solution phase antibody.

The term "$k_{off}$" refers to the dissociation rate constant of a particular antibody-antigen interaction. A $k_{off}$ dissociation rate constant can be measured by surface plasmon resonance, for example using the BIACORE™ system.

The term "surface plasmon resonance" refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson U. et al., Ann. Biol. Clin. 51:19-26 (1993); Jonsson U. et al., Biotechniques 11:620-627 (1991); Jonsson B. et al., J. Mol. Recognit. 8:125-131 (1995); and Johnsson B. et al., Anal. Biochem. 198:268-277 (1991).

The binding affinity and dissociation rate of a MAdCAM antagonist antibody to MAdCAM can be determined by any suitable method. The binding affinity can be measured by ELISAs, RIAs, flow cytometry, and surface plasmon resonance, such as BIACORE™. The dissociate rate can be measured by surface plasmon resonance. One can determine whether an antibody has substantially the same $K_D$ as a MAdCAM antagonist antibody by using any suitable method. Example 7 of U.S. Pat. No. 8,188,235 (herein incorporated by reference) exemplifies a method for determining affinity constants of anti-MAdCAM monoclonal antibodies.

One can determine whether an antibody binds to the same epitope or cross-competes for binding with a MAdCAM antagonist antibody by using any suitable method. In one example, one allows a MAdCAM antagonist antibody to bind to MAdCAM under saturating conditions and then measures the ability of the test antibody to bind to MAdCAM. If the test antibody is able to bind to MAdCAM at the same time as the MAdCAM antagonist antibody, then the test antibody binds to a different epitope as the MAdCAM antagonist antibody. However, if the test antibody is not able to bind to MAdCAM at the same time, then the test antibody binds to the same epitope, an overlapping epitope, or an epitope that is in close proximity to the epitope bound by the huma MAdCAM antagonist antibody. This experiment can be performed using an ELISA, a RIA, BIACORE™, or flow cytometry (FACS).

To test whether a MAdCAM antagonist antibody cross-competes with another MAdCAM antagonist antibody, one may use the competition method described herein in two directions, i.e., determining if the reference antibody blocks the test antibody and vice versa. In one example, the experiment is performed using an ELISA.

MAdCAM antibodies or antigen-binding portions thereof can be produced by a variety of techniques, including conventional monoclonal antibody methodology, for example the standard somatic cell hybridization technique of Kohler and Milstein (1975) Nature 256: 495. Other techniques for producing monoclonal antibodies can also be employed such as viral or oncogenic transformation of B lymphocytes.

MAdCAM antibodies or antigen-binding portions thereof can be prepared by recombinant expression of immunoglobulin light and heavy chain genes in a host cell. For example, to express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Various recombinant DNA methodologies are used to obtain antibody heavy and light chain genes, to incorporate these genes into recombinant expression vectors and to introduce the vectors into host cells, such as those described in Sambrook, Fritsch and Maniatis (eds), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397, the disclosures of which are incorporated herein by reference.

To express MAdCAM antibodies and antigen-binding portions thereof, DNAs encoding partial or full-length light and heavy chains, obtained as described herein, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. Expression vectors include, for example, plasmids, retroviruses, adenoviruses, adeno-associated viruses (AAV), plant viruses such as cauliflower mosaic virus, tobacco mosaic virus, cosmids, YACs, and EBV derived episomes. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or both genes are inserted into the same expression vector. The antibody genes are inserted into the expression vector by various methods (e.g., ligation of complementary restriction sites on the antibody gene fragment and vector, or blunt end ligation if no restriction sites are present).

In another aspect, the MAdCAM antibodies or antigen binding portions thereof may be deimmunized to reduce their immunogenicity using the techniques described in, e.g., PCT Publication Nos.: WO98/52976 and WO00/34317 (incorporated herein by reference).

Unless otherwise indicated, the "Clinical Remission" is defined as a Total Mayo score of 2 with no individual subscore >1 and rectal bleed subscore of 0 or 1. Where indicated, Clinical Remission may based on SCCAI, in which case the Clinical Remission is defined as a total SCCAI score <2.

"Clinical Response Rate" is defined as a decrease from baseline of at least 3 points in Total Mayo score with at least a 30% change, accompanied by at least 1 point decrease or absolute score of 0 or 1 in rectal bleeding subscore "Mucosal Healing" is defined as absolute Mayo subscore for endoscopy of 0 or 1

Structural Alignments

Structural alignments, which are usually specific to protein and sometimes RNA sequences, use information about the secondary and tertiary structure of the protein or RNA molecule to aid in aligning the sequences. Structural alignments are used as the "gold standard" because they explicitly align regions of the protein sequence that are structurally similar rather than relying exclusively on sequence information. A commonly used algorithm for structural alignments is TM-ALIGN (Zhang and Skolnick, Nucleic Acids Research, 33: 2302-2309 (2005)), which assigns increased weight to the most similar regions of the structure during superposition.

Sequence Alignment

Where structural alignment with protein sequences of the invention is not possible, for example due to an absence of target sequence NMR or crystal structure data, sequence alignment may be used. The skilled person is familiar with sequence alignment tools (such as BLAST, CLUSTAL and others known to the skilled person, such as those described herein), and is able to align sequences, particularly antibody constant domain sequences according to known structural motifs, especially due to the large number of exemplary structural studies already existent for immunoglobulin domains, antibodies and antibody constant domains in particular, across subtype and species.

For specific protein families with conserved structure, other alignment algorithms are available. In the case of antibodies, various algorithms for assigning Kabat numbering are available. The algorithm implemented in the 2012 release of Abysis (www.abysis.org) is used herein to assign Kabat numbering to variable regions unless otherwise noted.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wisconsin. FASTA, which includes, e.g. the programs FASTA2 and FASTA3, provides alignments and percent sequence identity of the regions of the best overlap between the query and search sequences (Pearson, *Methods Enzymol.* 183:63-98 (1990); *Pearson, Methods Mol. Biol.* 132:185-219 (2000); *Pearson, Methods Enzymol.* 266:227-258 (1996); *Pearson, J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

24-month follow-up period (6 monthly visits followed by 18 month extended contact (every 6 month telephone contacts).

In order to observe at least 300 subjects with 12 weeks of data, 357 subjects were randomized and treated at 105 sites across 21 countries.

Subjects were randomly assigned to one of the following arms: (1) 7.5 mg SC (n=60); (2) 22.5 mg SC (n=60); (3) 75 mg SC (n=60); (4) 225 mg SC (n=60); and placebo (n=60). Patients received an initial dose at week-0 (after a 6-week screening period), and received subsequent doses at week-4 and week-8.

Example 2 Study Endpoints

The primary objective of this study was to characterize the dose-response and efficacy of mAb 7.16.6 in inducing Clinical Remission based upon Total Mayo score in subjects with moderate to severe ulcerative colitis.

The total Mayo score consists of 4 components, each scored 0-3, with 3 being the worst. Two of the components, stool count and rectal bleeding, were obtained from daily diaries entered by patients into an interactive voice response system (IVRS). The third component of the Mayo score is a physician's global assessment. The final component is an endoscopic score (see MAYO scoring, below). All endoscopic scores were assessed by the investigator (local reader) as well as by a blinded central reader. Historically, clinical studies of ulcerative colitis patients have calculated the total Mayo score using a locally read endoscopy.

TABLE 2 mAb 7.16.6 VH, VL, and CDR Sequences

| SEQ ID | Description | Sequence |
|---|---|---|
| 3 | mAb 7.16.6 VL CDRs underlined SEQ IDs 11, 12, 13 | DIVMTQTPLS LSVTPGQPAS ISC<u>KSSQSLL HTDGTTYLYW</u> YLQKPGQPPQ LLIY<u>EVSNRF</u> SGVPDRFSGS GSG<u>T</u>DFTLKI SRVEAEDVGI YYC<u>MQNIQLP WTFGQGTKVE</u> IK |
| 4 | mAb 7.16.6 VH CDRs underlined SEQ IDs 14, 15, 16 | QVQLVQSGAE VKKPGASVKV SCKASGYTFT <u>SYGINWVRQA</u> PGQGLEWMGW ISVYSGNTNY AQKVQGRVTM TADTSTSTAY <u>MDLRSLRSDD</u> TAVYYCAR<u>EG SSSSGDYYYG MDV</u>WGQGTTV TVSS |

Examples

Example 1 Study Design

The Study was a Phase 2B proof of concept (POC), randomized, double-blind, placebo-controlled, parallel, dose ranging study being conducted to evaluate the efficacy, safety and PK of mAb 7.16.6. Subjects with moderate to severe ulcerative colitis were randomized in a 1:1:1:1 ratio to subcutaneous (SC) dose levels (7.5, 22.5, 75 and 225 mg) of mAb 7.16.6 or placebo. Participation in this study was for approximately 38 months which included up to a 6-week screening period, a 12-week treatment period, and a

| MAYO scoring | |
|---|---|
| Stool frequency†: | 0 = Normal no. of stools for this subject |
| | 1 = 1 to 2 stools more than normal |

-continued

| MAYO scoring | |
|---|---|
| | 2 = 3 to 4 stools more than normal |
| | 3 = 5 or more stools more than normal |
| | Subscore, 0 to 3 |
| Rectal bleeding‡: | 0 = No blood seen |
| | 1 = Streaks of blood with stool less than half the time |
| | 2 = Obvious blood with stool most of the time |
| | 3 = Blood alone passes |
| | Subscore, 0 to 3 |

MAYO scoring

| | |
|---|---|
| Findings on endoscopy: | 0 = Normal or inactive disease<br>1 = Mild disease (erythema, decreased vascular pattern, mild friability)<br>2 = Moderate disease (marked erythema, lack of vascular pattern, friability, erosions)<br>3 = Severe disease (spontaneous bleeding, ulceration)<br>Subscore, 0 to 3 |
| Physician's global assessment§: | 0 = Normal<br>1 = Mild disease<br>2 = Moderate disease<br>3 = Severe disease<br>Subscore, 0 to 3 |

\* The Mayo score ranges from 0 to 12, with higher scores indicating more severe disease. Data are from Schroeder et al.
†Each subject serves as his or her own control to establish the degree of abnormality of the stool frequency.
‡The daily bleeding score represents the most severe bleeding of the day.
§The physician's global assessment acknowledges the three other criteria, the subject's daily recollection of abdominal discomfort and general sense of wellbeing, and other observations, such as physical findings and the subject's performance status.

Efficacy Endpoints
Primary Efficacy Endpoint:
Proportion of subjects in Clinical Remission at Week 12 (defined as a Total Mayo score of ≤2 with no individual subscore >1 and rectal bleed subscore of 0 or 1).

Key Secondary Efficacy Endpoints:
Proportion of subjects with a Clinical Response at Week 12 (defined as a decrease from baseline of at least 3 points in Total Mayo score with at least a 30% change, accompanied by at least 1 point decrease or absolute score of 0 or 1 in rectal bleeding subscore).
Proportion of subjects with Mucosal Healing at Week 12 (defined as absolute Mayo subscore for endoscopy of 0 or 1).
Proportion of subjects with decrease from baseline in Partial Mayo score of 2 with no individual subscore >1 at Weeks 4, 8, 12.
Change from baseline (CFB) in Total Mayo score at Week 12, and CFB in individual Mayo subscores at Weeks 4, 8, 12.
CFB in Fecal Calprotectin and hsCRP at Weeks 4, 8, 12.

Safety and PK, and PK/PD Endpoints:
Safety and tolerability evaluated by the frequency of AEs, SAEs, AEs leading to discontinuation of study treatment
mAb 7.16.6 concentration-time profile
Pharmacokinetic and anti-drug anti-body data summary, including preliminary population PK.

Exploratory Endpoints:
Proportion of subjects with Clinical Remission (defined as a total SCCAI Score of ≤2 points) at Weeks 4, 8 and 12
Soluble MAdCAM in blood at baseline and Week 12 and CFB.

Example 3 Analysis Methods

Analyses of Primary Endpoint
The pre-specified primary endpoint analysis was based on 1) Emax model; 2) Linear in dose model; or 3) CMH method using minimum risk weights (Mehrotra and Railkar, 2000). Since the observed data did not support the monotonic increasing dose-response trend for either Emax and linear in dose model, the CMH method stratified by the previous anti-TNF therapy experience was used for the analysis of primary endpoint. The 1-sided adjusted p-values using Hochberg's step up method, although not pre-specified, are presented in this report to support adjustment for multiple comparisons.

Analyses of Secondary Endpoints
The key secondary and exploratory endpoints using binary data at week 4, 8 or 12 were analyzed using the CMH method. Continuous endpoints at week 4, 8 or 12 were analysed using the analysis of covariance (ANCOVA) model and/or Linear Mixed Model (LMM).

Imputation of Missing Values in Binary Endpoints
A treatment failure approach was used for missing value imputation for dropout subjects in analyses of binary endpoints in primary, secondary, and exploratory endpoints where the CMH method was used. For ANCOVA and LMM models, only observed data were used; no imputation was done. For longitudinal analysis, since Generalized Linear Mixed model is valid under the assumption of Missing at Random, no imputation was done, data as observed were used.

Analysis Population Sets
Based on the study design, the original randomization was preserved from Week 0-12 but not after Week 12. The Week 0-12 analysis set was performed on the following populations:
Modified Intent-to-Treat (mITT) Population: the full analysis set consisting of all randomized subjects who received at least one dose of investigational product.
Safety Analysis Population: includes all enrolled subjects who received at least one dose of study drug. This population includes subjects who were treated but for various reasons did not receive randomly assigned investigational product.
Per Protocol (PP) Population: a subset of mITT analysis population but excludes all subjects identified with key protocol violations.
PK Population: includes all subjects received 1 dose of investigational product and have data on at least one PK concentration timepoint.

Example 4 Subject Disposition and Demographics

A total of 587 subjects were screened to obtain 357 randomized subjects, all of whom received at least 1 dose of study drug. These 357 subjects constitute the mITT analysis population and the safety analysis population. There were 2 subjects that received different treatment from that assigned for all 3 doses. These two subjects were both randomly assigned to 22.5 mg dose group and both received the 75 mg dose group which is reflected in Table 3 below.

To support the analyses of the primary and secondary endpoints, sensitivity analyses were done using the PP population which constitutes 320 subjects. A total of 37 subjects were excluded from the PP analysis set due to identification of key protocol deviations. Twelve of these subjects received one or more incorrect dose(s).

TABLE 3

Subject Disposition and Evaluation by Treatment Group

| Subjects Screened (n = 587) | Placebo | mAb 7.16.6 7.5 mg | mAb 7.16.6 22.5 mg | mAb 7.16.6 75 mg | mAb 7.16.6 225 mg |
|---|---|---|---|---|---|
| Assigned to Study Treatment | 73 | 71 | 72 | 71 | 70 |
| mITT Set | 73 | 71 | 72 | 71 | 70 |
| PP Set | 67 | 56 | 66 | 65 | 66 |

TABLE 3-continued

Subject Disposition and Evaluation by Treatment Group

| Subjects Screened (n = 587) | Placebo | mAb 7.16.6 7.5 mg | mAb 7.16.6 22.5 mg | mAb 7.16.6 75 mg | mAb 7.16.6 225 mg |
|---|---|---|---|---|---|
| Safety Set | 73 | 71 | 70* | 73* | 70 |
| Completed 12 week treatment period | 68 | 63 | 69 | 70 | 66 |
| Ongoing treatment at time of snapshot | 0 | 0 | 0 | 0 | 0 |
| Reasons for discontinuation (N): | 5 | 8 | 1 | 3 | 4 |
| Insufficient Clinical Response | 1 | 1 | 0 | 0 | 0 |
| No longer willing to participate | 2 | 0 | 0 | 0 | 2 |
| AE | 2 | 6 | 0 | 3 | 1 |
| Other | 0 | 1 | 1 | 0 | 1 |

*Two subjects assigned to 22.5 mg treatment group received 75 mg treatment group treatment for all 3 doses.

TABLE 4

Demographic and Baseline Characteristics

| | Placebo | mAb 7.16.6 7.5 mg | mAb 7.16.6 22.5 mg | mAb 7.16.6 75 mg | mAb 7.16.6 225 mg |
|---|---|---|---|---|---|
| N | 73 | 71 | 70 | 73 | 70 |
| Age (years): mean (SD) | 38.6 (12.7) | 41.3 (12.5) | 42.1 (14.7) | 37.7 (12.4) | 41.3 (13.3) |
| Gender (Female, Male) | (29, 44) | (32, 39) | (25, 45) | (35, 38) | (28, 42) |
| Race: n(%) | | | | | |
| White | 65 (89.0%) | 64 (90.1%) | 64 (91.4%) | 64 (87.7%) | 57 (81.4%) |
| Black | 3 (4.1%) | 1 (1.4%) | 0 | 0 | 2 (2.9%) |
| Asian | 3 (4.1%) | 5 (7.0%) | 5 (7.1%) | 7 (9.6%) | 8 (11.4%) |
| Other | 2 (2.7%) | 1 (1.4%) | 1 (1.4%) | 2 (2.7%) | 3 (4.3%) |
| Weight (kg) (SD) | 76.9 (21.2) | 70.7 (16.3) | 72.4 (16.9) | 74.2 (18.7) | 75.5 (17.5) |
| BMI (kg/m$^2$) (SD) | 25.5 (6.0) | 24.3 (4.2) | 24.3 (4.5) | 25.4 (6.0) | 25.4 (5.8) |
| Height (cm) (SD) | 173.2 (9.3) | 169.8 (9.7) | 172.3 (10.1) | 170.8 (8.7) | 172.5 (9.9) |
| Anti-TNF experience | | | | | |
| Naive | 31 (42.5%) | 30 (42.3%) | 30 (42.9%) | 31 (42.5%) | 30 (42.9%) |
| Experienced | 42 (57.5%) | 41 (57.7%) | 40 (57.1%) | 42 (57.5%) | 40 (57.1%) |
| Current use of IS therapy: n(%) | | | | | |
| Azathioprine (AZA) | 12 (16.4%) | 18 (25.4%) | 15 (21.4%) | 17 (23.3%) | 17 (24.3%) |
| 6-Mercaptopurine (6-MP) | 1 (1.4%) | 4 (5.6%) | 4 (5.7%) | 4 (5.5%) | 2 (2.9%) |
| Methotrexate (MTX) | 2 (2.7%) | 1 (1.4%) | 4 (5.7%) | 0 | 1 (1.4%) |
| No Immunosuppressives | 58 (79.5%) | 48 (67.6%) | 47 (67.1%) | 52 (71.2%) | 50 (71.4%) |
| Current use of Corticosteroids: n(%) | | | | | |
| Corticosteroids | 31 (42.5%) | 38 (53.5%) | 37 (52.9%) | 37 (50.7%) | 36 (51.4%) |
| No use of Corticosteroids | 42 (57.5%) | 33 (46.5%) | 33 (47.1%) | 36 (49.3%) | 34 (48.6%) |
| Current use of 5-ASA/Mesalazine | | | | | |
| 5-ASA/Mesalazine | 47 (64.4%) | 37 (52.1%) | 35 (50%) | 45 (61.6% 0 | 35 (50.0%) |
| No use of 5-ASA/Mesalazine | 26 (35.6%) | 34 (47.9%) | 35 (50%) | 28 (38.4%) | 35 (50.0%) |
| Smoking Status | | | | | |
| Never smoked | 47 | 40 | 46 | 48 | 45 |
| Smoker | 4 | 4 | 2 | 5 | 5 |
| Ex Smoker | 22 | 27 | 22 | 20 | 20 |
| Baseline Total Mayo score (SD) | 8.4 (1.71) | 8.7 (1.65) | 8.1 (1.63) | 8.4 (1.94) | 8.7 (1.60) |
| Baseline SCCAI score (SD) | 7.4 (2.91) | 7.9 (2.79) | 7.4 (2.79) | 7.2 (2.55) | 7.4 (2.36) |

Example 5 Efficacy

Primary Efficacy Endpoint—Clinical Remission at Week 12
Key Secondary Efficacy Endpoints—Clinical Response and Mucosal Healing at Week 12

Figure 1B:
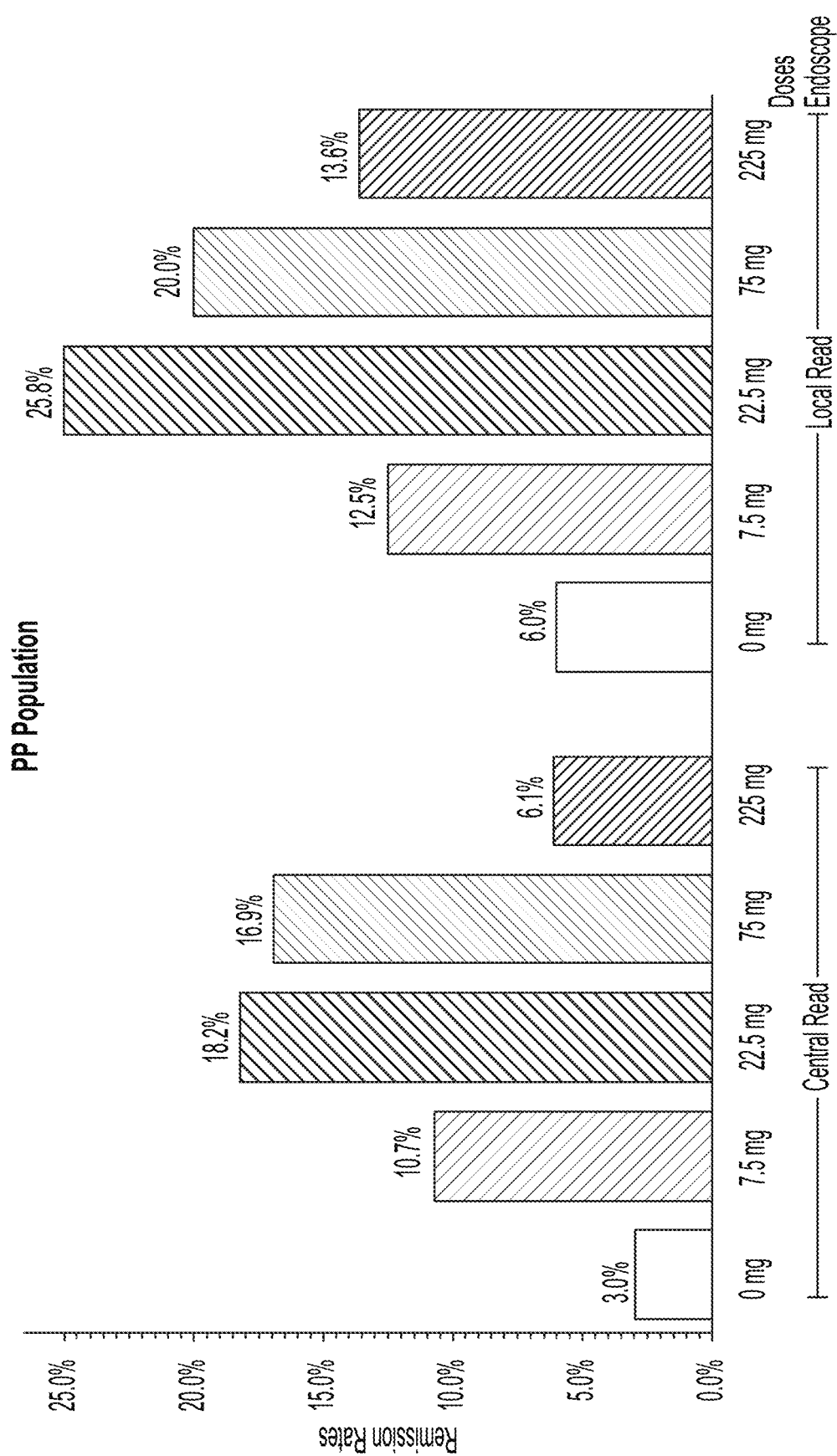
Figure 2A:
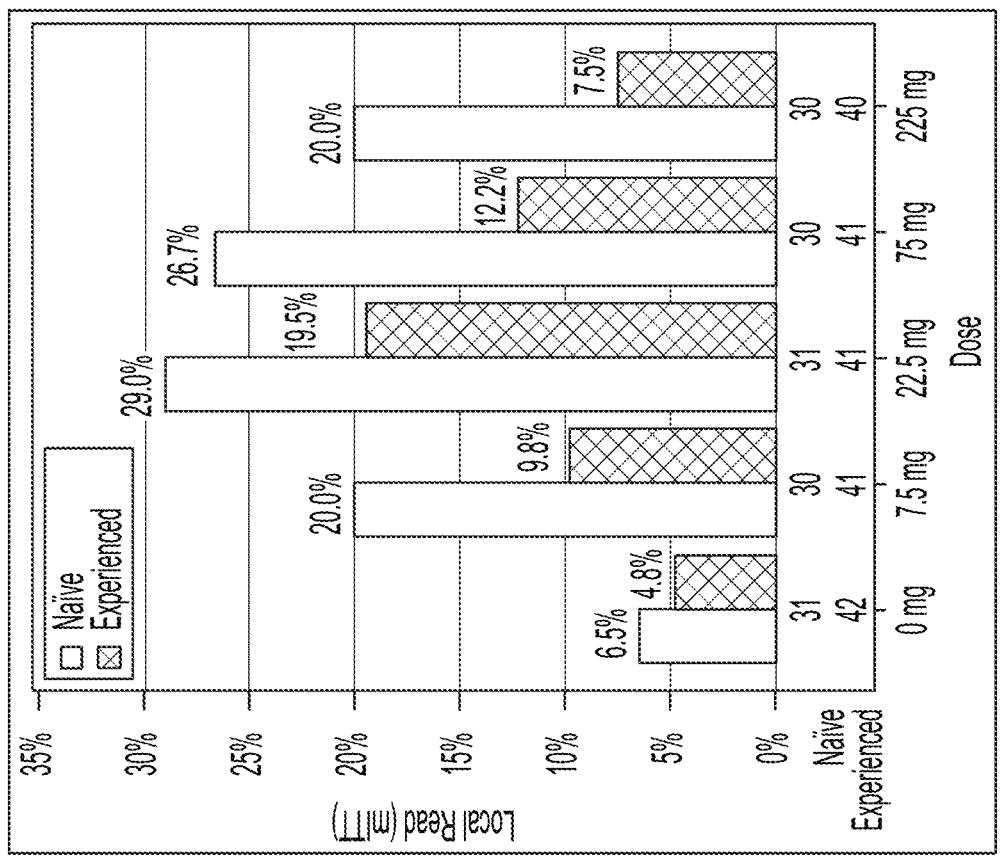
FIG. 2A, FIG. 2B, FIG. 2C, and FIG. 2D: Clinical remission rate based on naïve and experience population at week 12 (treatment failure approach).
Figure 2B:
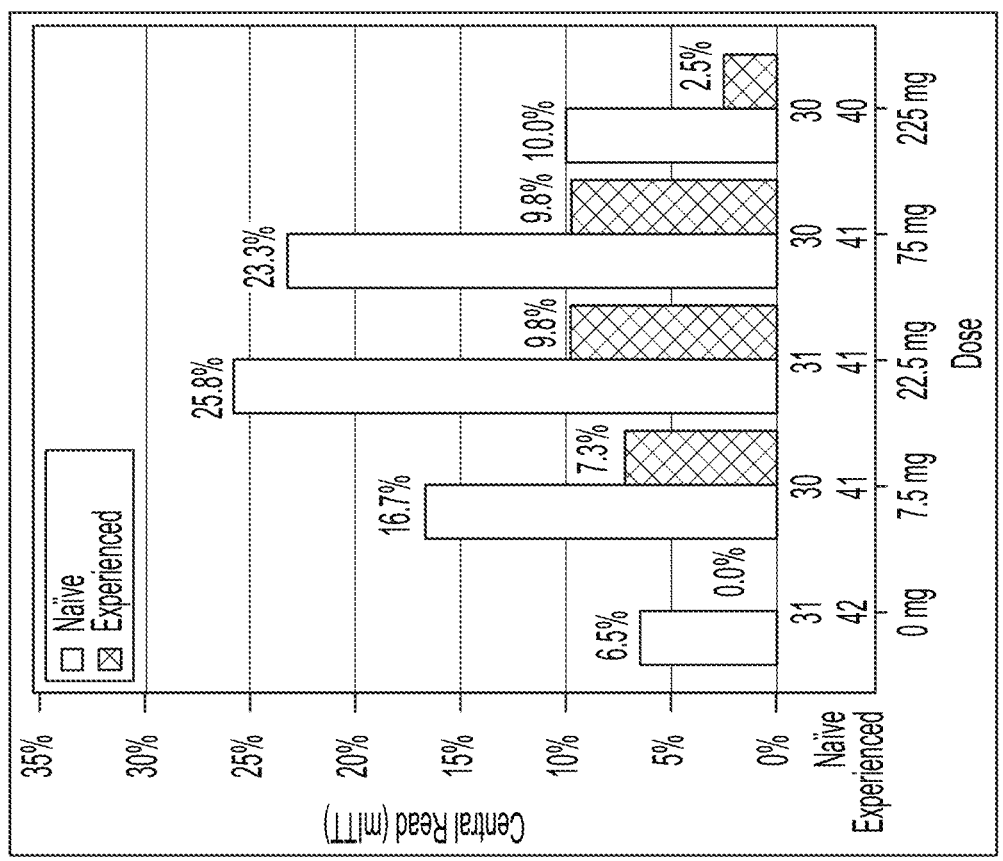
Figures 2C, 2D:
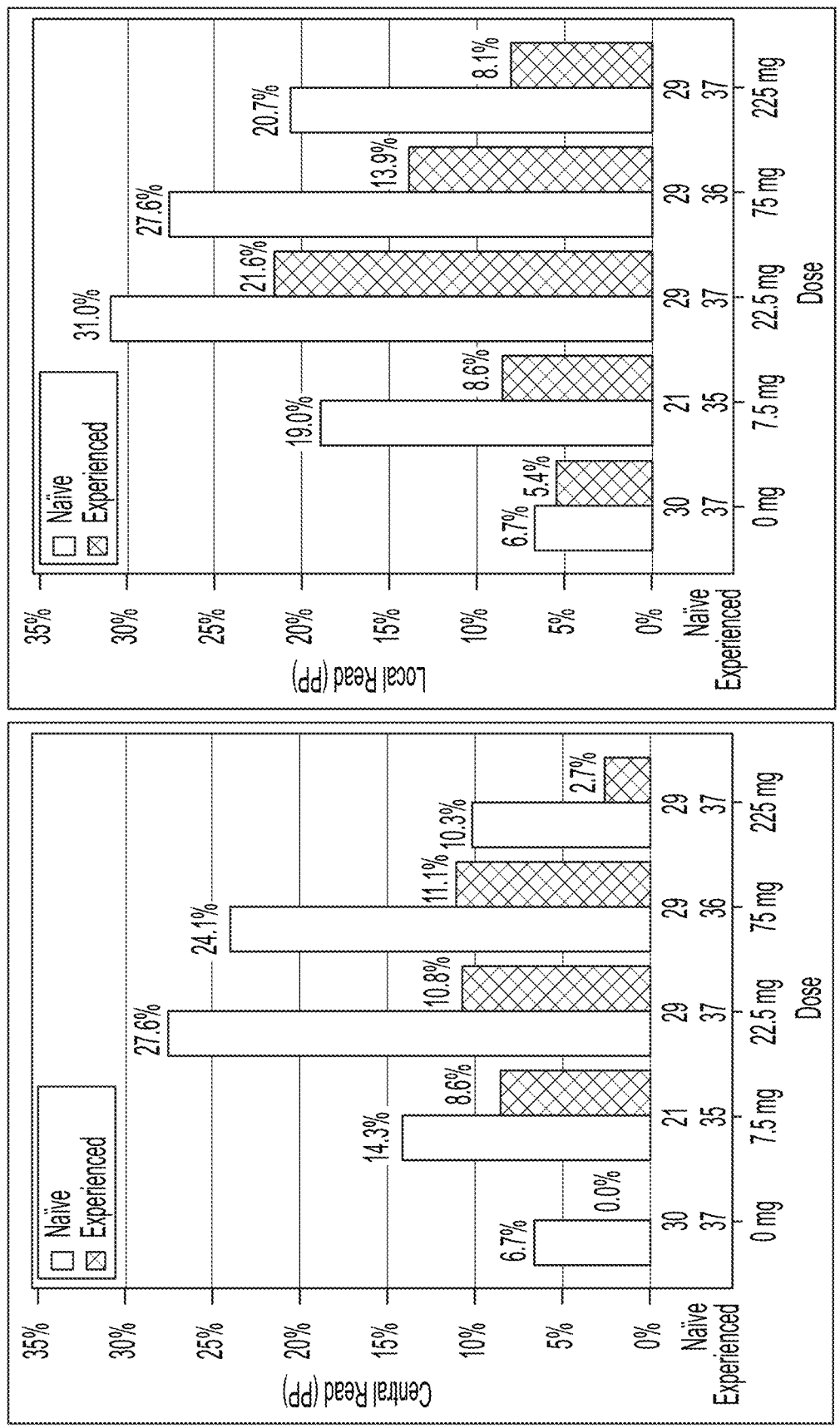
Figures 3A, 3B:
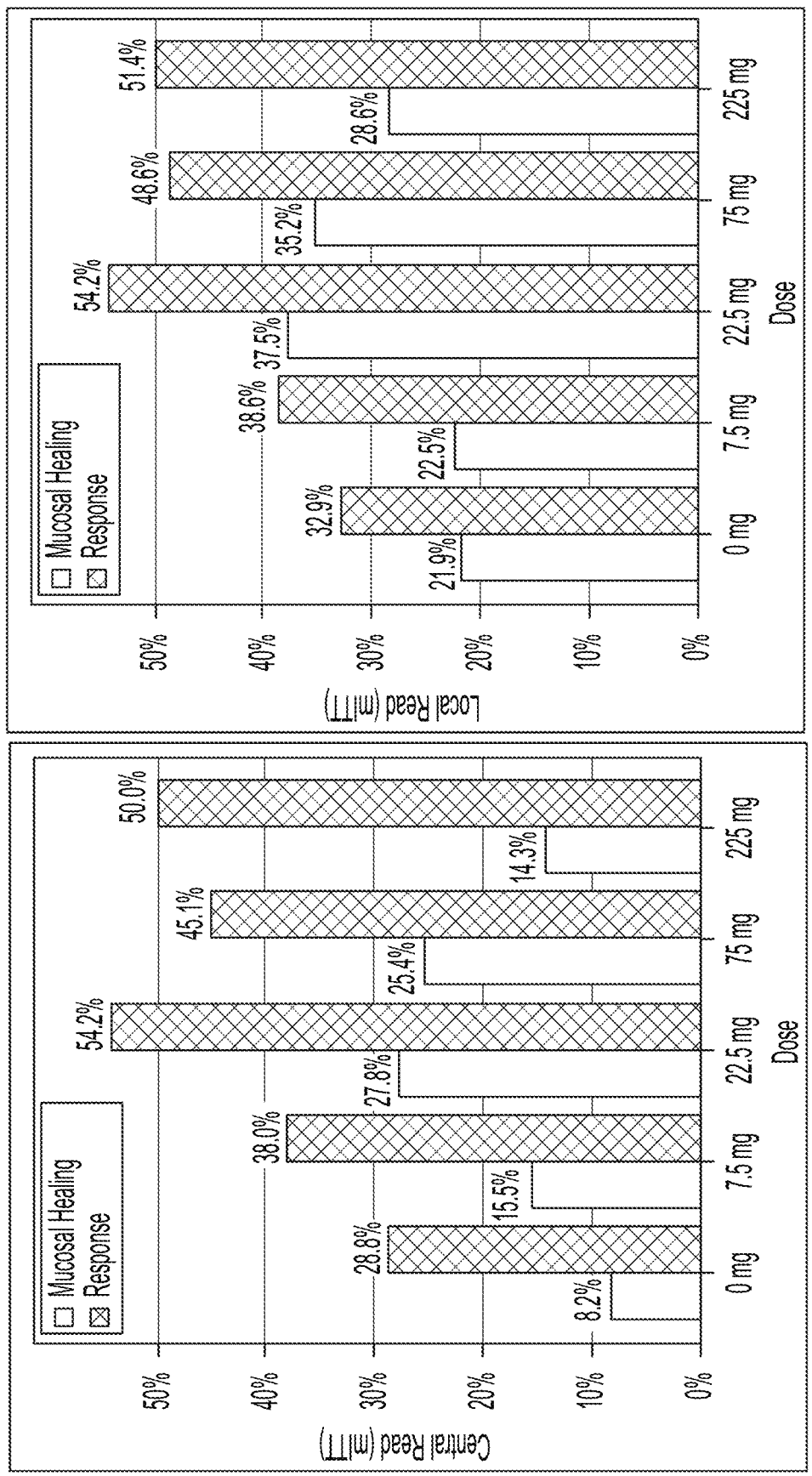
FIG. 3A and FIG. 3B: Clinical response and mucosal healing rates at week 12 (treatment failure approach).

FIG. 1A and FIG. 1B show the observed Clinical Remission rates at week 12 for each treatment group derived from central and local read for both mITT and PP populations. In general, remission rates using the local read are higher than those using the central read. Remission rates in mITT population calculated using the central read for placebo, 7.5 mg, 22.5 mg, 75 mg and 225 mg of mAb 7.16.6 were 2.7%, 11.3%, 16.7%, 15.5%, and 5.7%, respectively; whereas remission rates calculated using local reads were 5.5%, 14.1%, 23.6%, 18.3%, and 12.9%, respectively, In PP population corresponding rates were slightly higher, but preserving the same trend, where 22.5 mg was the highest among four treatment groups, followed by the rate from 75 mg.

The observed Clinical remission rates by stratum of anti-TNF exposure (experienced or naïve) at week 12 were analyzed and presented in FIG. 2A, FIG. 2B, FIG. 2C, and FIG. 2D. In general, the observed Clinical Remission rates in the mITT population showed a similar trend, and showed higher rates among naïve patients vs. experienced patients. PP analysis results supported the same findings as the mITT population, but showed greater effect sizes between treatment and placebo groups.

Figure 4:
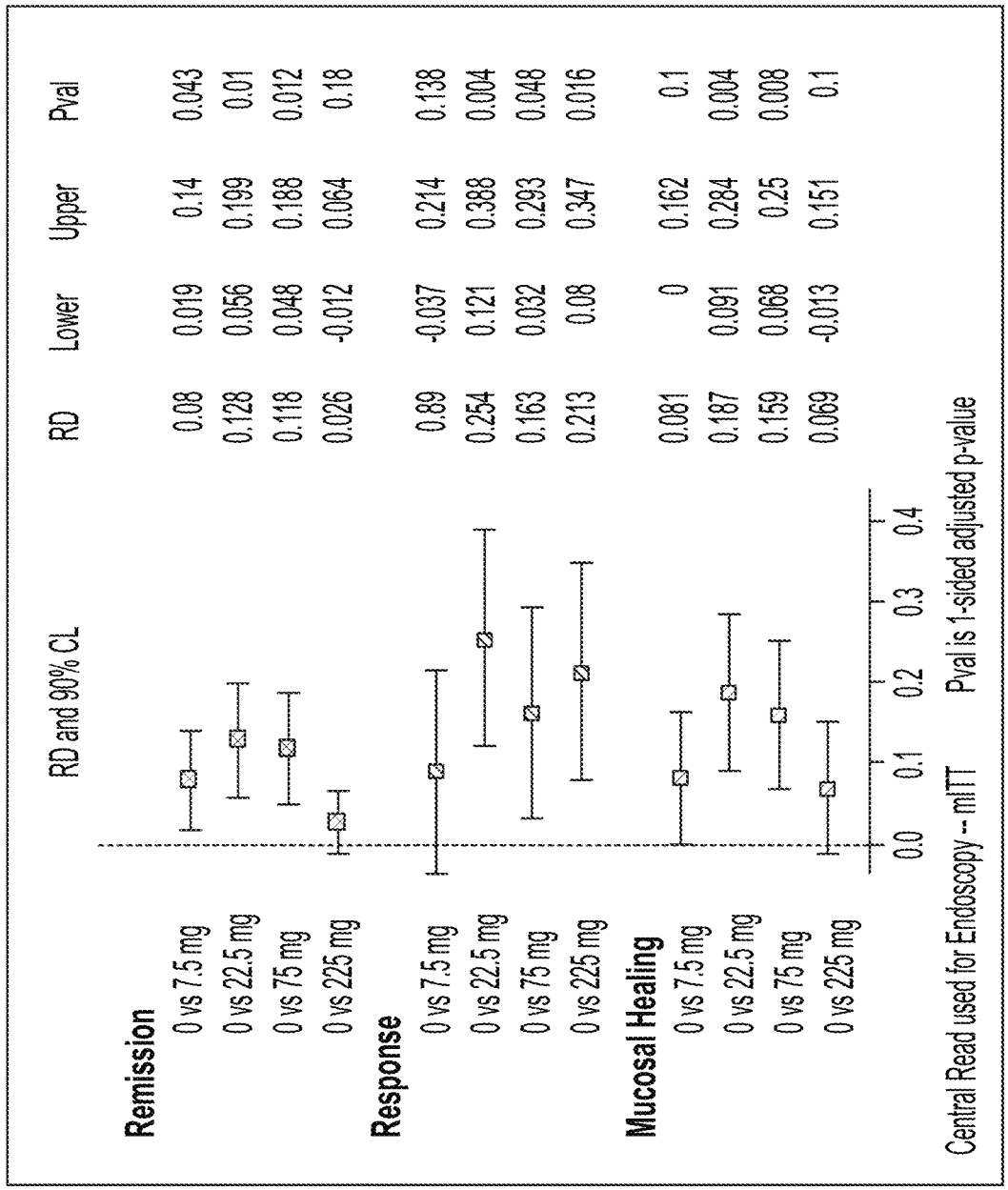
FIG. 4: Geometric mean (and 90% confidence interval) of percent change from baseline in fecal calprotectin (ug/g) (mitt, observed cases).

Analyses for the primary endpoint (Clinical Remission) and the key secondary endpoints (Clinical Response and Mucosal Healing) based on the central read are shown in FIG. 4. For the primary endpoint Clinical Remission, three out of four treatment groups (7.5 mg, 22.5 mg, and 75 mg) showed statistically significant efficacy benefit over placebo group. The Clinical Remission rates of 7.5 mg, 22.5 mg and 75 mg over placebo at week 12 were 8.0% (p=0.043), 12.8% (p=0.010) and 11.8% (p=0.012), respectively. In terms of Clinical Response, three of four treatment groups, 22.5 mg, 75 mg and 225 mg, have shown statistical efficacy compared with placebo with effect sizes (RD=Risk Difference) of 25.4% (p=0.004), 16.3% (p=0.048) and 21.3% (p=0.016), respectively. Mucosal Healing rates for 22.5 mg and 75 mg over placebo are significantly different from placebo with effect sizes of 18.7% (p=0.004) and 15.9% (p=0.008), respectively. The Clinical Remission and Mucosal Healing rates for the highest dose 225 mg compared to placebo are the lowest among all dose groups. In contrast, Clinical Response for the 225 mg dose group is the second highest, and is significantly different from placebo.

Figure 5:
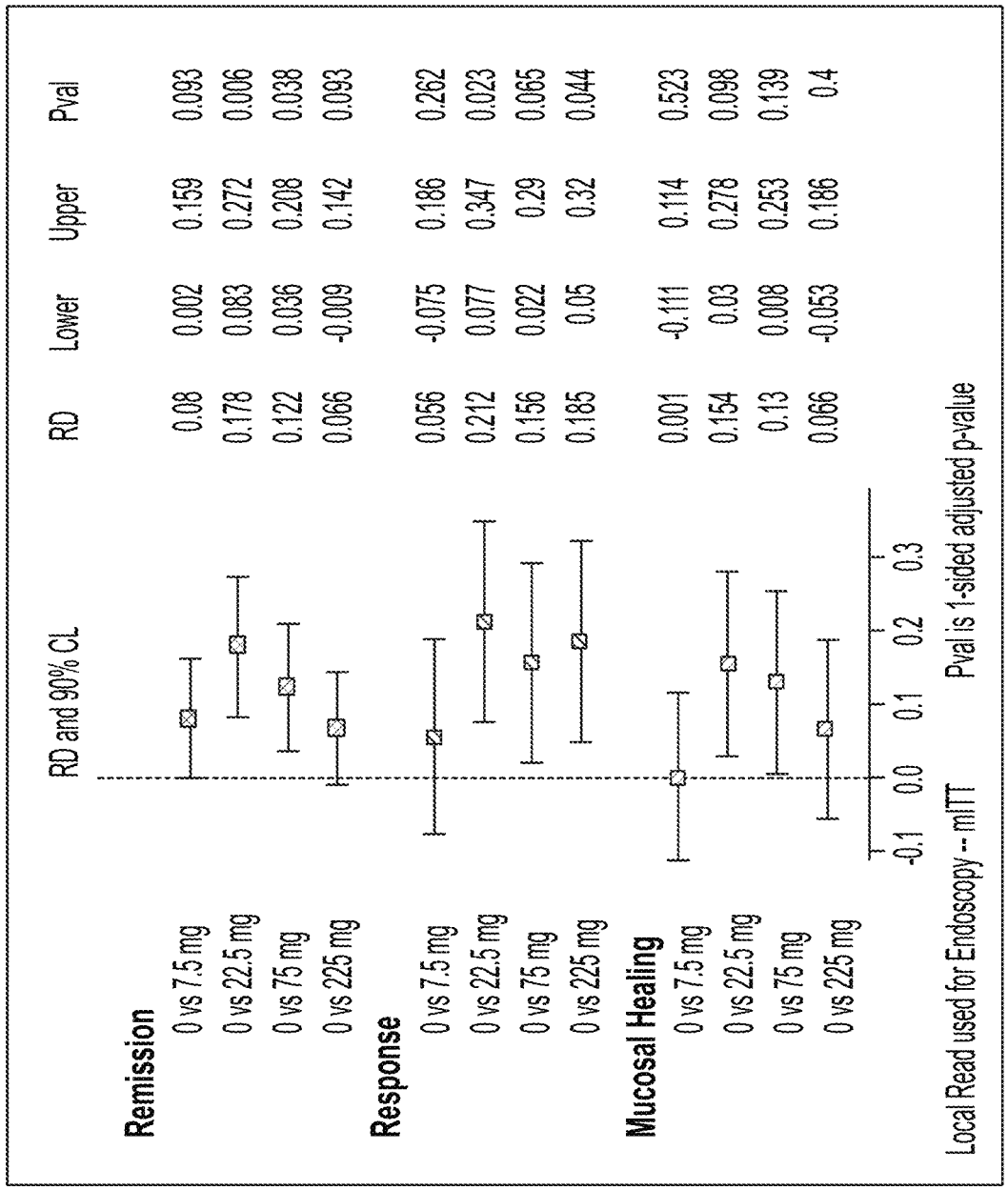
FIG. 5: Geometric mean (and 90% confidence interval) of percent change from baseline in soluble madcam (pmol/1) by treatment group at week 12 (mitt, observed cases).

The results corresponding to the local read follow a similar trend (FIG. 5). The effect sizes are, in general, higher than those using central read scores. Clinical Remission rates for 22.5 mg and 75 mg are statistically significant with effect sizes of 17.8% (p=0.006) and 12.2% (p=0.038), respectively. Clinical Response for 22.5 mg and 225 mg were also statistically significant with effect sizes of 21.2% (p=0.023) and 18.5% (p=0.044). The Clinical Response for 75 mg is marginally non-significant (p=0.065). None of the doses separated from placebo statistically in terms of Mucosal Healing possibly because of the high placebo rate (21.9%). Similar results are also observed in the PP population under these two analyses.

Key Secondary Efficacy Endpoints—Partial Mayo Score

Figure 6:
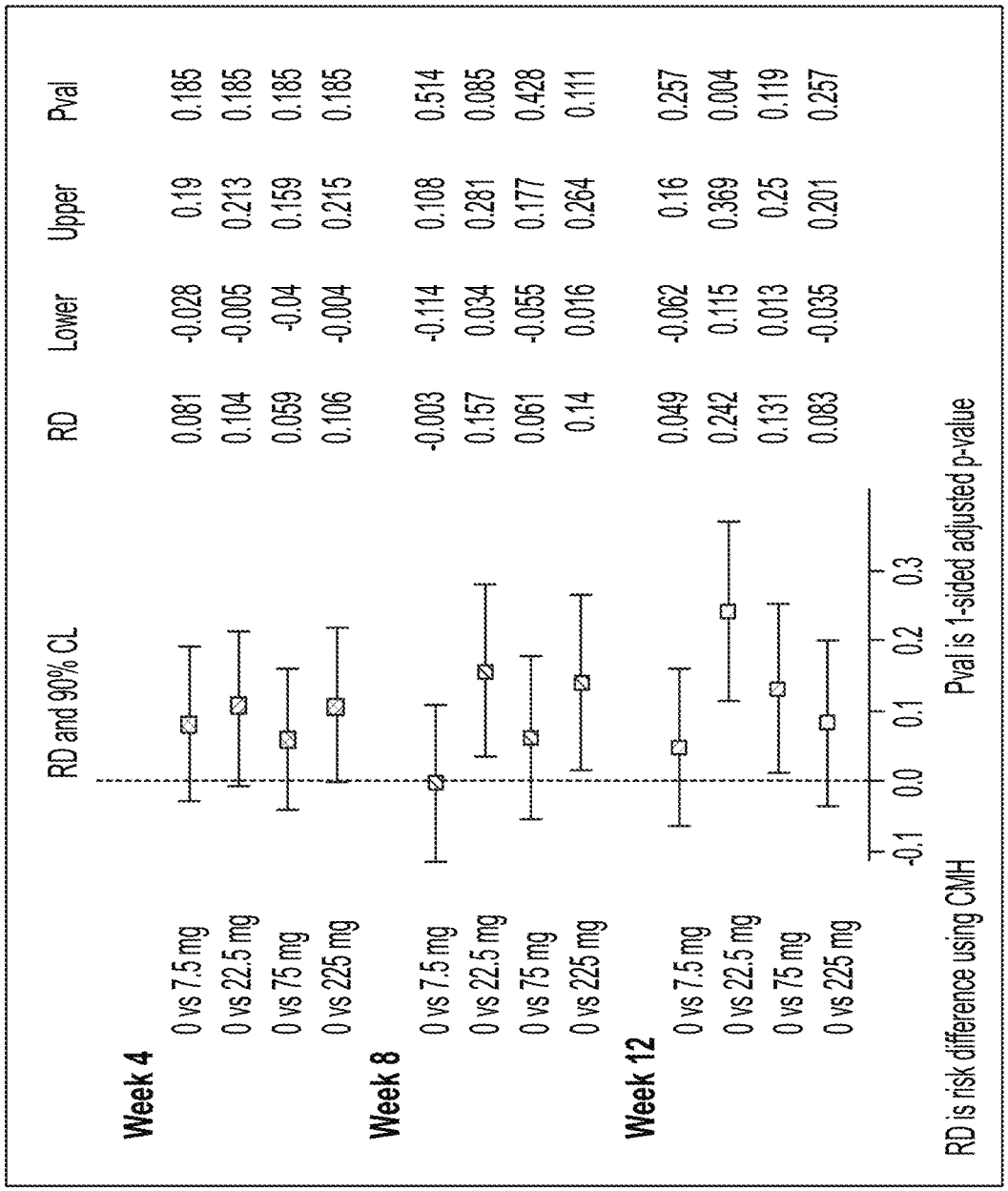
FIG. 6: Geometric mean (and 90% confidence interval) of percent change from baseline in hscrp (mg/dl) (mitt, week 0-12, observed cases).

FIG. 6 summarizes the proportion of subjects with decrease from baseline in Partial Mayo score of ≤2 with no individual subscore >1 at Weeks 4, 8, 12. These data were analyzed using the same CMH method that was used for the primary endpoint analysis. The results for the change from baseline in partial Mayo score at week 12 are consistent with the primary endpoint analysis: 22.5 mg differentiated from placebo (p=0.004) and 75 mg, although not significant, was the next closest effect size. At week 4 all four doses had shown almost similar effect sizes, however starting from week 8 they started to differentiate from placebo. Analysis results with PP population provided the same trend with slightly higher RD in each timepoint.

All the analyses presented above for primary and key secondary endpoints used binary endpoints. To support the above findings of clinical efficacy, change from baseline using the total Mayo score at week 12 was analyzed fitting an ANCOVA model. The results from ANCOVA using the central read data are presented in Table 5. The difference from placebo group vs. 22.5 mg appeared to be the highest followed by 225 mg, and all four treatment group were statistically different from placebo. These findings are similar to the analysis of Clinical Response, since response is determined based on change from baseline on Mayo score. The analyses using the local read are also consistent with these findings.

Figure 12:
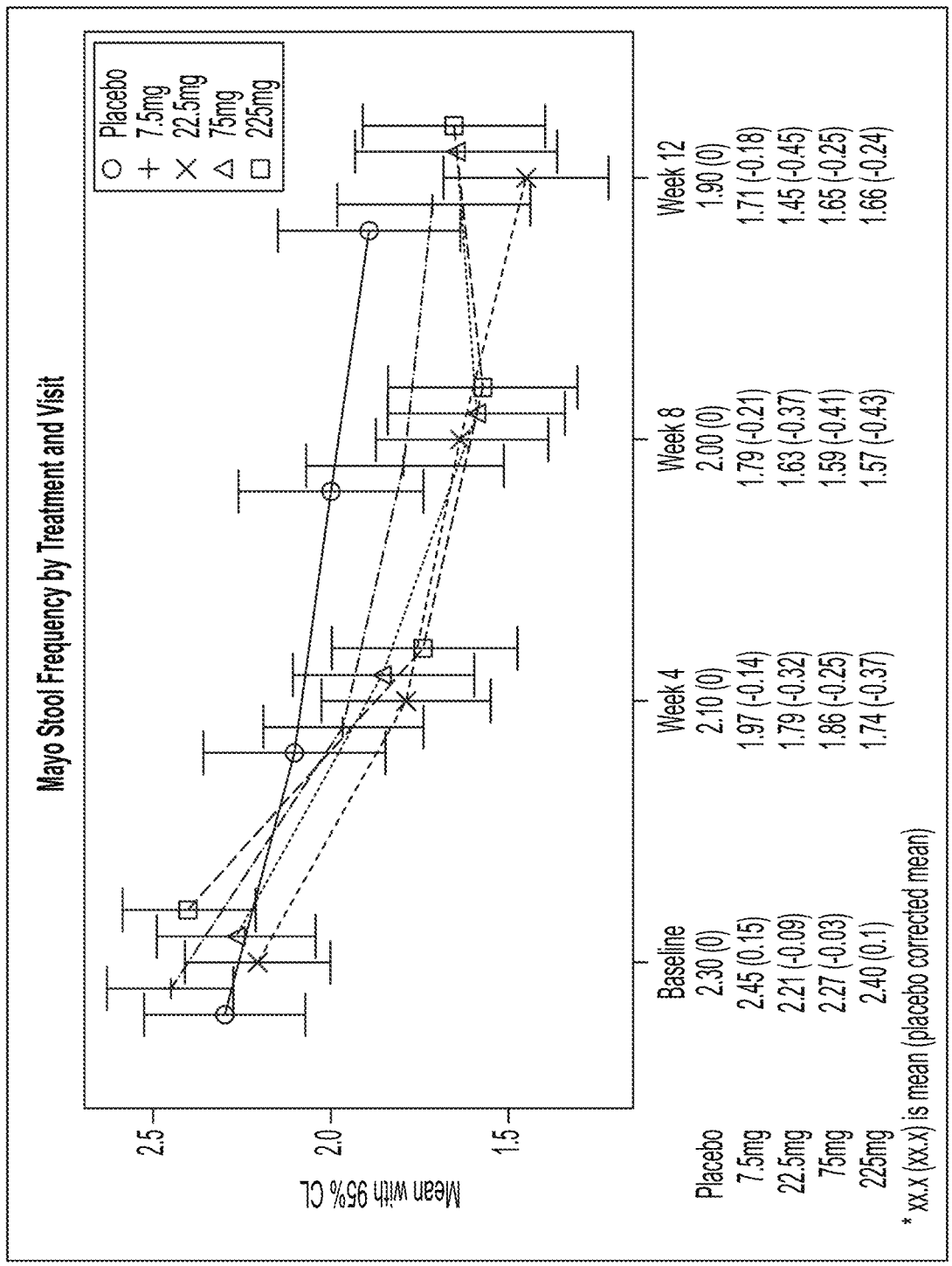
FIG. 12: Efficacy Table: Mayo stool frequency by treatment and visit.

FIG. 12 shows that randomization resulted in well-balanced stool frequency scores at baseline. All treatment arms were better than placebo by week 4, and the maximum effect at week 12 was observed in the 22.5 mg treatment arm. Stool frequency is a component of both the full Mayo score and the partial Mayo score. It is reported daily and normalized to pre-morbid values and graded on a scale of 0-3. A score of 0 indicates that the stool frequency the same as the pre-morbid value; a score of 1 indicates 1-2 more stools/day than normal; a score of 2 indicates 3-4 mores stools/day than normal; and a score of 3 indicates >4 more stools than normal each day. Data for each subject represents the mean of 3 values prior to the assessment date. Each point on the graph is the mean (SEM) for a treatment at an evaluation day. In the data table, the parenthetical value adjacent to the mean is the placebo-corrected mean, i.e. the mean minus the corresponding placebo value.

Figure 13:
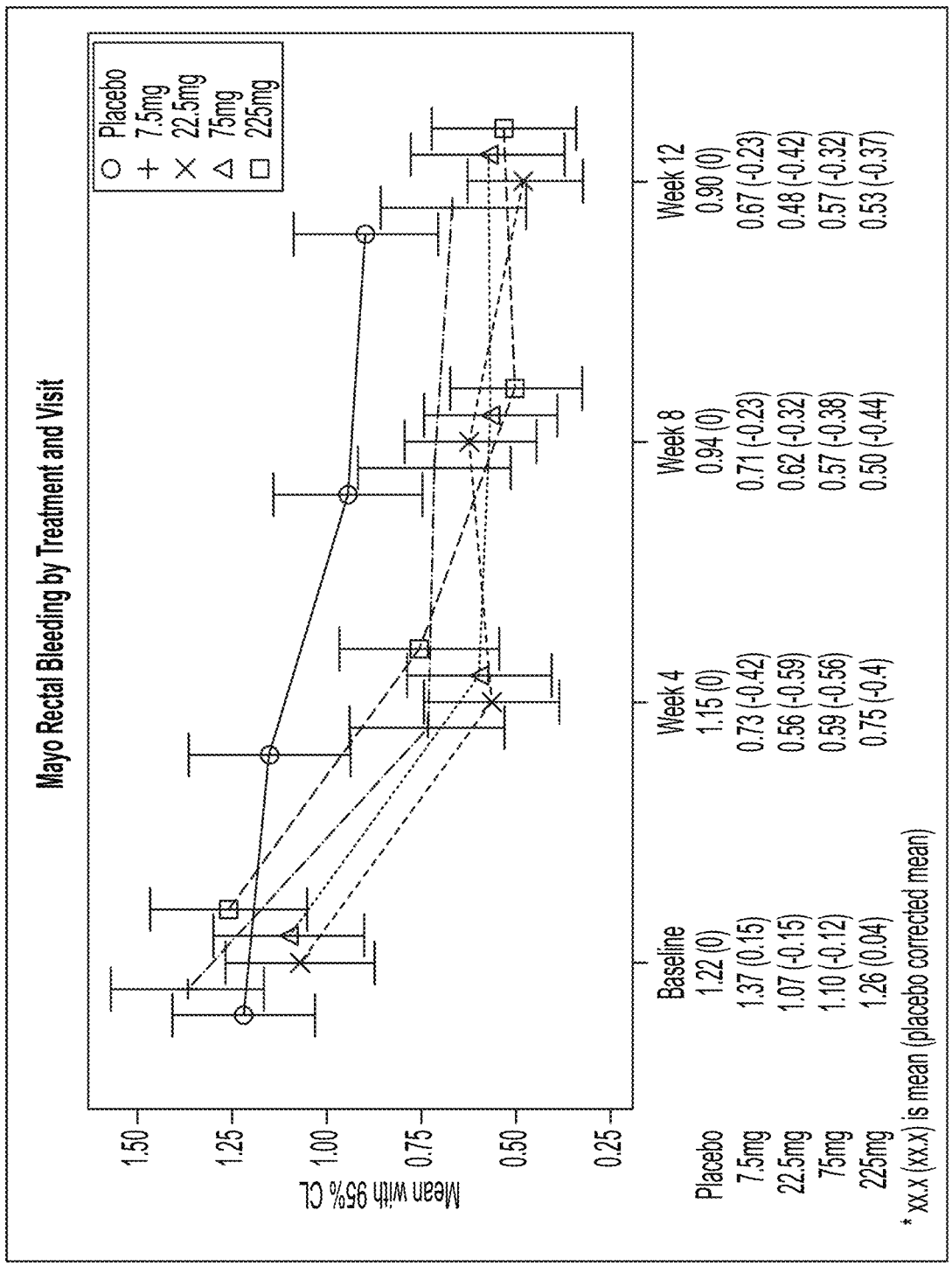
FIG. 13: Efficacy Table: Mayo rectal bleeding by treatment and visit.

FIG. 13 shows that that randomization resulted in well-balanced rectal bleeding scores at baseline. All treatment arms were better than placebo by week 4, and this effect was sustained through week 12, with the greatest effect at that visit seen in the 22.5 mg arm. Rectal bleeding is a component of both the full Mayo score and the partial Mayo score. It is reported daily and graded on a scale of 0-3. A score of 0 indicates no bleeding; a score of 1 indicates that there was visible blood with stool <50% of the time; a score of 2 indicates visible blood with the stool ≥50% of the time; and a score of 3 indicates passage of blood alone, without stool. Data for each subject represents the mean of 3 values prior to the assessment date. Each point on the graph is the mean (SEM) for a treatment at an evaluation day. In the data table, the parenthetical value adjacent to the mean is the placebo-corrected mean, i.e. the mean minus the corresponding placebo value.

Figure 14:
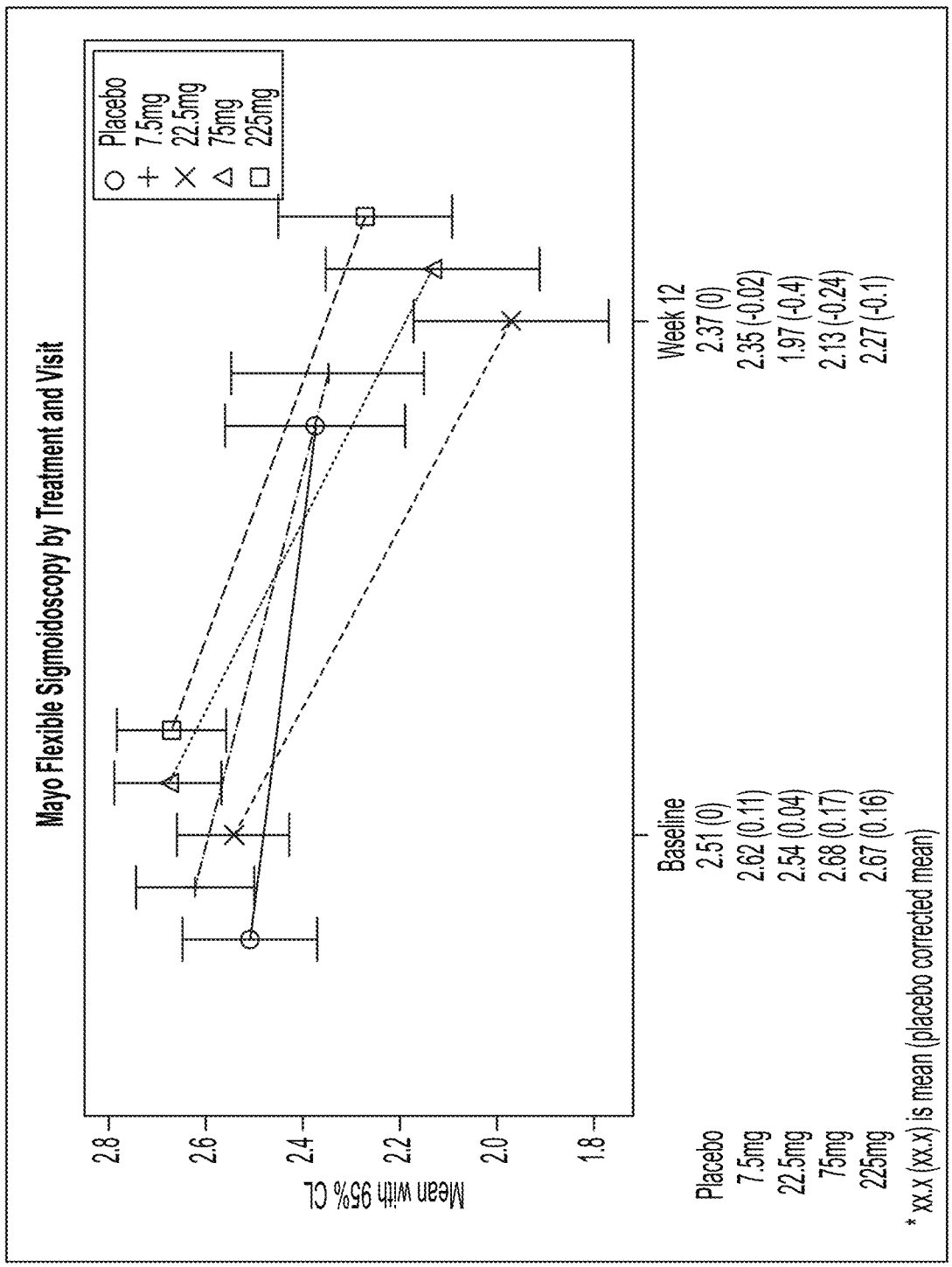
FIG. 14: Efficacy Table: Mayo flexible sigmoidoscopy by treatment and visit.

FIG. 14 shows that randomization resulted in well-balanced flexible sigmoidoscopy scores at baseline. All treatment arms were better than placebo at week 12, and the greatest effect at that visit seen in the 22.5 mg arm. Flexible sigmoidoscopy is a component of the full Mayo score. It was performed prior the baseline visit and immediately prior to the week 12 visit. It is scored on a scale of 0-3. A score of 0 indicates normal colonic mucosa or inactive disease; a score of 1 indicates mild disease characterized by erythema, decreased vascular pattern, and/or mild friability; a score of 2 indicates Moderate disease characterized by marked erythema, absent vascular pattern, friability, and/or erosions; a score of 3 indicates severe disease with ulceration and spontaneous bleeding. Each point on the graph is the mean (SEM) for a treatment at the evaluation day. In the data table, the parenthetical value adjacent to the mean is the placebo-corrected mean, i.e. the mean minus the corresponding placebo value.

Figure 15:
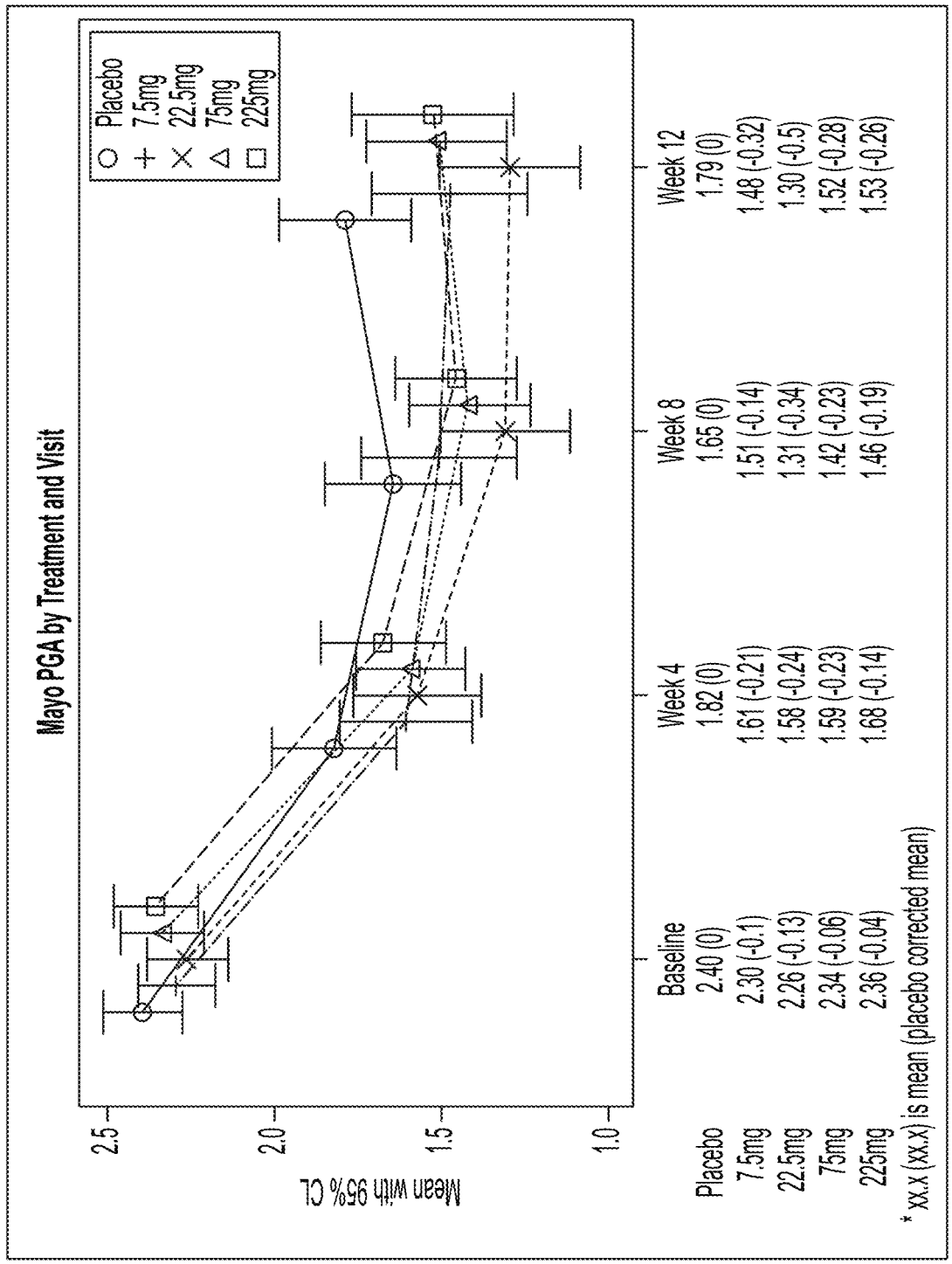
FIG. 15: Efficacy table: Mayo PGA by treatment and visit.

FIG. 15 shows that randomization resulted in well-balanced PGA scores at baseline. As expected from the protocol, subjects' disease was considered moderate to severe at baseline. All treatment arms were better than placebo at week 12, and the greatest effect at that visit seen in the 22.5 mg arm. The Physician's Global Assessment is a component of both the full Mayo score and the partial Mayo score. It reflects the subjective assessment of the treating physician taking into account all aspects of the subject's ulcerative colitis. It is scored on a scale of 0-3. A score of 0 indicates that the subject is normal; a score of 1 indicates mild disease; a score of 2 indicates Moderate disease; a score of 3 indicates severe disease. Each point on the graph is the mean (SEM) for a treatment at the evaluation day. In the data table, the parenthetical value adjacent to the mean is the placebo-corrected mean, i.e. the mean minus the corresponding placebo value.

TABLE 5

Change from Baseline in Total Mayo score at Week 12 (ANCOVA, Central Read)

Based on ANCOVA Model*

| Treatment | Estimate | Difference from Placebo | 90% CI |
|---|---|---|---|
| Placebo | −1.53 | | |
| 7.5 mg | −2.41 | −0.88 | (−1.623, −0.145) |
| 22.5 mg | −3.06 | −1.53 | (−2.254, −0.809) |
| 75 mg | −2.65 | −1.12 | (−1.845, −0.390) |
| 225 mg | −2.80 | −1.27 | (−2.016, −0.533) |

*Model includes treatment, baseline Total Mayo score and anti-TNF status as fixed effects.

Example 6 Exploratory Endpoint—SCCAI

Figure 7:
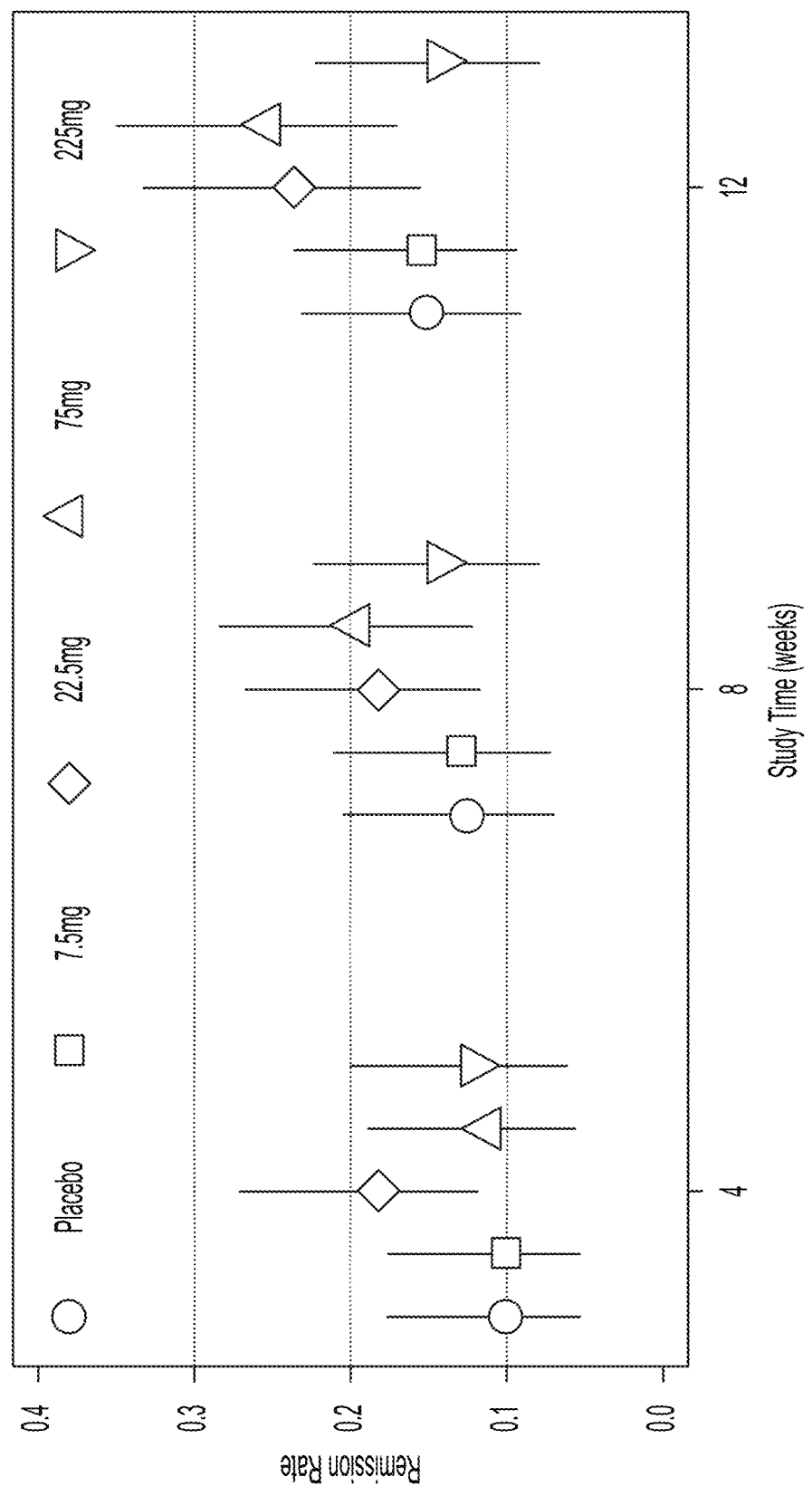

Clinical Remission based on another pre-specified scoring system, the Simple Clinical Colitis Activity Index (SCCAI), was derived as a check for consistency of clinical effect (Table 6). SCCAI does not include endoscopy. The Clinical Remission at a given time point based on SCCAI is defined as a total SCCAI score <2. The observed remission rates (with treatment failure approach) and the corresponding 90% confidence intervals at week 4, 8, and 12 are plotted in FIG. 7. At all-time points, the remission rates corresponding to doses 22.5 mg and 75 mg are higher than the other two doses, and over time, these two doses separate further. The SCCAI results at week 12 are consistent with Clinical Remission results based on Mayo score.

TABLE 6

Simple Clinical Colitis Activity Index (SCCAI) Scores

| | 0 | 1 | 2 | 3 | 4 |
|---|---|---|---|---|---|
| Bowel Frequency (day) | 1-3 | 4-6 | 7-9 | >9 | |
| Bowel Frequency (night) | 1-3 | 4-6 | | | |
| Urgency of Defecation | — | Hurry | Immediately | Incontinence | |
| Blood in Stool | — | Trace | Occasionally frank | Usually frank | |
| General well-being | Very well | Slightly below par | Poor | Very Poor | Terrible |
| Arthritis, pyoderma gangrenosum, eruthema, nodosum, uveitis | | 1 per manifestation | | | |

Example 7 Safety

There was no evidence of a safety signal observed in this study. The safety population consisted of 357 subjects who were randomized and received at least one dose of study drug. Subjects were analyzed by treatment received. Subject disposition is presented in Table 7. There were 2 subjects that received different treatment from that assigned for all 3 doses. Both were assigned to the 22.5 mg dose group and both received 75 mg. Adverse events were slightly more common in drug treated (162/284=57%) than placebo-treated subjects (39/73=53%), although there was no clear evidence of relationship to dose (Table 7).

TABLE 7

Subject Disposition for Safety (Weeks 0-12)

| | Placebo | mAb 7.16.6 7.5 mg | mAb 7.16.6 22.5 mg | mAb 7.16.6 75 mg | mAb 7.16.6 225 mg |
|---|---|---|---|---|---|
| Subject Evaluable for Adverse Events | 73 | 71 | 70 | 73 | 70 |
| Number of AEs | 83 | 120 | 79 | 85 | 117 |
| Subjects with AEs | 39 (53.4) | 40 (56.3) | 36 (51.4) | 43 (58.9) | 43 (61.4) |
| Subjects Discontinued due to AEs | 2 (2.7) | 5 (7.0) | 0 | 3 (4.1) | 1 (1.4) |
| Subjects with SAEs | 4 (5.5) | 10 (14.1) | 1 (1.4) | 3 (4.1) | 3 (4.3) |
| Deaths | 0 | 1 (1.4) | 0 | 0 | 0 |

Discontinuations

There were 21 discontinuations during the treatment phase, including 12 due to adverse event drop outs (Table 8). Most of the 12 adverse event drop outs were due to worsening of ulcerative colitis (7) and other GI events (3). The majority of these events occurred in the 7.5 mg (n=6) arm during the first 30 days of the study. There was no evidence of a drug or dose response.

TABLE 8

Discontinuations Due to Adverse Events

| | Placebo | mAb 7.16.6 7.5 mg | mAb 7.16.6 22.5 mg | mAb 7.16.6 75 mg | mAb 7.16.6 225 mg |
|---|---|---|---|---|---|
| N | 73 | 71 | 70 | 73 | 70 |
| Ulcerative Colitis | 1 | 4 | 0 | 2 | 0 |
| Other GI | 1 | 2 | 0 | 0 | 0 |
| Other | 0 | 0 | 0 | 1 | 1 |

Deaths

There was one death during this study. A 30 year old woman who received 7.5 mg was diagnosed with adenocarcinoma of the colon 30 days after the first dose of study drug. Prior to study entry, the patient experienced a marked weight loss over a short period of time with a BMI at screening of 15.8 kg/m². The pre-study colonoscopy was abnormal with a stenotic area in the rectum, but biopsy did not show dysplasia. The subject had a further 10% weight loss within the first four weeks on study drug. Repeat sigmoidoscopy revealed more significant stenosis, and biopsy of the stenotic lesion at that time showed adenocarcinoma. She discontinued study drug, and died from metastatic colon cancer 3 months later. The cancer was considered present before study entry despite the negative biopsy, and that it was unlikely that this fatal adverse event was associated with the use of the study drug. The e-DMC also agreed on this causality.

Serious Adverse Events

The frequency of serious adverse events was highest in the 7.5 mg treatment arm (n=10), but all other arms, including placebo, had similar SAE frequencies reported (n=1-4). There were 26 serious adverse events in 22 subjects. The most common SAE was ulcerative colitis, reported by 9 subjects followed by migraine, reported by 2 subjects. Other gastrointestinal SAEs (one event each) included abdominal pain, adenocarcinoma of the colon, anal abscess, anal fissure, appendicitis, diarrhea, constipation, C. difficile infection and vomiting. Other, non-gastrointestinal SAEs (one event each) included complicated migraine, migraine, epilepsy, extremity pain, retinal artery embolism, vasovagal syncope, pulmonary embolism and tension headache.

Protocol Specific Medically Important Events

Over the course of the study, a very active surveillance program was in place to evaluate any risk of PML and myocarditis. Neither of these events was observed.

Adverse Events

Overall, mAb 7.16.6 appeared well-tolerated. The frequency of adverse events, while slightly higher in drug-(57%) than placebo-treated (53%) subjects, did not increase with dose. The most common adverse events by system organ class (SOC) were Infections and Infestations, Gastrointestinal disorders, Nervous System Disorders, Musculoskeletal disorders and General Disorders and Administration Site Conditions (Table 9)

TABLE 9

Most Common Adverse Events by System Organ Class

| | Placebo | mAb 7.16.6 7.5 mg | mAb 7.16.6 22.5 mg | mAb 7.16.6 75 mg | mAb 7.16.6 225 mg |
|---|---|---|---|---|---|
| N | 73 | 71 | 70 | 73 | 70 |
| Any AE | 39 (53%) | 40 (56%) | 36 (51%) | 43 (59%) | 43 (61%) |
| Infections and Infestations | 13 (18%) | 13 (18%) | 12 (17%) | 17 (23%) | 17 (24%) |
| Gastrointestinal Disorders | 14 (19%) | 21 (30%) | 9 (13%) | 9 (12%) | 12 (17%) |
| Nervous System Disorders | 8 (11%) | 8 (11%) | 8 (11%) | 6 (8%) | 15 (21%) |
| Musculoskeletal Disorders | 7 (10%) | 10 (14%) | 11 (16%) | 8 (11%) | 7 (10%) |
| General and Administration Site | 5 (7%) | 7 (10%) | 7 (10%) | 11 (15%) | 8 (11%) |

Outside of the gastrointestinal tract and related tissues, MAdCAM is constitutively found in breast, nasal tissue and spleen. No adverse events were reported for breast or spleen. The incidence of nasopharyngitis and upper respiratory tract infections were not different among treatment groups (Table 10).

TABLE 10

Nasopharyngitis and Upper Respiratory Tract Infections

| | Placebo | mAb 7.16.6 7.5 mg | mAb 7.16.6 22.5 mg | mAb 7.16.6 75 mg | mAb 7.16.6 225 mg |
|---|---|---|---|---|---|
| N | 73 | 71 | 70 | 73 | 70 |
| Nasopharyngitis | 3 (4.1%) | 0 | 3 (4.3%) | 5 (6.8%) | 4 (5.7%) |
| Upper Respiratory Tract Infection | 1 (1.4%) | 2 (2.8%) | 2 (2.9%) | 1 (1.4%) | 2 (2.9%) |

Figure 16:
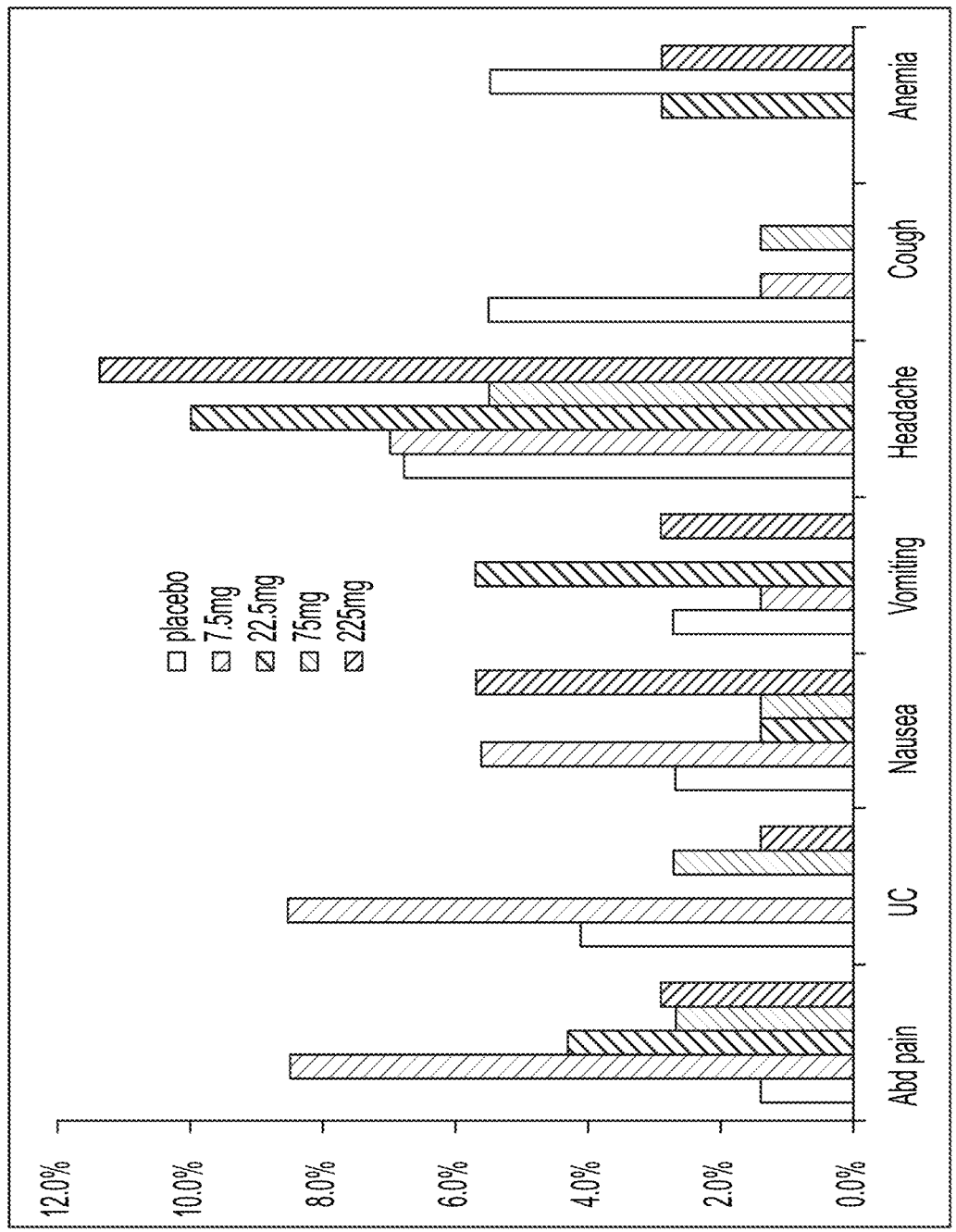
FIG. 16: Most common adverse events by treatment group.

Common adverse events (those that were observed in at least 4 subjects in 1 treatment arm) were abdominal pain, ulcerative colitis, nausea, vomiting, headache, cough and anemia. The most common AE was headache, reported by up to 10% of subjects, followed by abdominal pain and ulcerative colitis. There was no evidence of a dose effect for any of these events (Table 11 and FIG. 16).

Injection site reactions reported as erythema, pain, swelling and burning sensation were uncommon, observed more frequently in the 225 mg treatment arm (10%) but were evenly distributed throughout the other treatment arms (3-4%) including placebo. mAb 7.16.6 appears safe and well-tolerated in this patient population.

TABLE 11

Adverse Events that occurred in 4 or more subjects in at least one treatment group

| | Placebo | mAb 7.16.6 7.5 mg | mAb 7.16.6 22.5 mg | mAb 7.16.6 75 mg | mAb 7.16.6 225 mg |
|---|---|---|---|---|---|
| N | 73 | 71 | 70 | 73 | 70 |
| Gastrointestinal Disorders | | | | | |
| Abdominal pain | 1 (1.4%) | 6 (8.5%) | 3 (4.3%) | 2 (2.7%) | 2 (2.9%) |
| Colitis Ulcerative | 3 (4.1%) | 6 (8.5%) | 0 | 2 (2.7%) | 1 (1.4%) |
| Nausea | 2 (2.7%) | 4 (5.6%) | 1 (1.4%) | 1 (1.4%) | 4 (5.7%) |
| Vomiting | 2 (2.7%) | 1 (1.4%) | 4 (5.7%) | 0 | 2 (2.9%) |
| Nervous System Disorders | | | | | |
| Headache | 5 (6.8%) | 5 (7.0%) | 7 (10%) | 4 (5.5%) | 8 (11.4%) |
| Respiratory, Thoracic and Mediastinal Disorders | | | | | |
| Cough | 4 (5.5%) | 1 (1.4%) | 0 | 1 (1.4%) | 0 |
| Blood and Lymphatic System Disorders | | | | | |
| Anemia | 0 | 0 | 2 (2.9%) | 4 (5.5%) | 2 (2.9%) |

Example 8 Biomarkers 8.1 Protein Biomarkers Identified by Serum Protein Profiling Background. Blood and tissue samples were collected at various time points in all dose groups and used to measure a panel of proteins using Olink Biosciences highly multiplexed protein assay platform. The concentrations of 202 proteins were measured using this sensitive and accurate assay platform, and were compared between samples taken prior to treatment to samples taken 4 weeks and 12 weeks after initial dosage. Biomarkers that predict response to treatment are analyzed by correlating the starting concentration of a single or multiple proteins from samples taken prior to treatment, as well as the change in the protein concentration from baseline to week-4 or week-12. These protein data are analyzed together with data from RNA, genotyping, and cell population data. Results of protein assays showing deviance from their respective control value are shown in Tables 12 and 13. Anti-MAdCAM antibody was administered every 4 weeks.

Methods. Serum proteins from patients enrolled in the MAdCAM UC POC study were measured from samples taken prior to treatment and at 4 weeks and 12 weeks during the dosing period of treatment using Olink Biosciences proximity extension assay platform. In total, proteins were measured from 937 serum samples collected from 331 subjects at 3 time points during the 12-week treatment period Three commercial assays, the Proseek Multiplex CVD I$^{96 \times 96}$, Proseek Multiplex INF I$^{96 \times 96}$, and Proseek Multiplex ONC v2 I$^{96 \times 96}$, were used to measure 202 unique proteins in the study serum samples by Olink.

Results. Many proteins have a different concentration at 4 weeks and 12 weeks during the dosing period of the anti-MAdCAM treatment compared to starting concentration values. Proteins with the largest median difference between pretreatment and 4 weeks post anti-MAdCAM treatment compared to pretreatment and week 4 of the placebo arm are summarized in Table 12. Shown is the median change and quartile 1, quartile 3 values for each group for each marker. The data are analyzed for biomarkers of response using statistical modeling.

TABLE 12

Median (Q3, Q1) Change from Baseline to Week 4

| Analyte | Placebo | 7.5 | 22.5 | 75 | 225 |
|---|---|---|---|---|---|
| CHI3L1 | −1.95 (25.00, −31.63) | −20.16 (25.61, −35.70) | −17.63 (4.94, −33.63) | −15.71 (21.89, −28.50) | −8.58 (20.06, −24.93) |
| CXCL1 | −3.89 (9.54, −20.13) | −4.58 (11.83, −16.65) | −10.34 (5.17, −20.30) | −14.85 (−1.84, −28.03) | −9.54 (3.23, −26.99) |
| CXCL13 | 1.26 (24.31, −14.67) | −9.51 (9.07, −29.01) | −9.48 (10.59, −23.04) | −4.99 (11.96, −25.70) | 4.13 (28.10, −27.03) |
| CXCL9 | −7.81 (14.51, −35.12) | −18.71 (22.18, −42.01) | −22.56 (8.61, −41.31) | −23.96 (4.64, −40.60) | −22.27 (1.39, −37.93) |
| Dkk-1 | −3.99 (15.49, −19.28) | 0.06 (16.80, −16.76) | −13.74 (18.74, −25.17) | −8.77 (13.07, −21.21) | −3.15 (25.81, −16.84) |
| EGF | −3.46 (45.02, −43.18) | 4.93 (43.71, −32.74) | −8.14 (25.60, −26.39) | −15.08 (40.81, −49.55) | −1.71 (38.78, −45.73) |
| EN-RAGE | 7.33 (56.57, −31.02) | −14.25 (13.78, −41.29) | −10.59 (30.17, −43.61) | −7.25 (41.81, −34.19) | −5.37 (35.54, −44.62) |
| EPO | 0.00 (9.72, −23.19) | 0.00 (7.50, −22.81) | −10.30 (3.66, −33.64) | −4.08 (10.74, −43.33) | 0.00 (22.11, −15.80) |
| IL-17C | −2.96 (10.42, −17.44) | 6.00 (26.52, −10.94) | −11.47 (15.50, −27.53) | −15.17 (18.03, −41.43) | −6.57 (33.21, −25.05) |
| IL-6 | −3.36 (40.05, −44.00) | −19.69 (21.54, −48.43) | −20.72 (10.36, −48.96) | −23.66 (1.80, −42.36) | −5.86 (28.05, −33.00) |
| IL-7 | 1.47 (29.44, −26.21) | −1.10 (33.39, −19.12) | −9.97 (8.82, −25.80) | −14.29 (15.05, −29.43) | −1.54 (22.17, −24.30) |
| MIP-1 alpha | −2.68 (21.97, −26.94) | 0.00 (30.66, −18.09) | −14.38 (7.56, −34.21) | −8.00 (34.94, −23.88) | −6.28 (29.78, −34.02) |
| MMP-1 | −4.86 (14.27, −20.04) | −2.93 (17.33, −14.56) | −9.59 (1.03, −19.42) | −16.51 (2.07, −39.61) | −4.02 (10.87, −19.54) |
| MMP-10 | −1.60 (13.90, −29.34) | −6.51 (21.19, −25.74) | −17.39 (0.55, −37.26) | −16.67 (0.78, −35.66) | −17.58 (8.30, −33.66) |
| MMP-12 | −5.75 (12.24, −33.84) | −8.73 (9.44, −26.97) | −22.98 (14.41, −44.81) | −25.63 (−4.39, −53.48) | −24.65 (11.48, −42.62) |
| MMP-3 | 1.48 (22.10, −19.63) | −2.68 (5.85, −16.76) | −11.35 (4.22, −30.34) | −7.80 (7.63, −25.55) | −8.58 (4.87, −27.97) |
| NT-pro-BNP | −1.02 (39.78, −27.99) | −0.58 (48.20, −36.15) | 2.36 (39.48, −31.01) | 16.67 (57.75, −31.37) | −3.57 (29.03, −28.57) |
| PTPN22 | 0.75 (50.09, −35.11) | −20.18 (10.04, −45.65) | −13.75 (23.70, −39.95) | −14.14 (17.69, −35.54) | −9.44 (28.16, −41.54) |
| PTX3 | −0.48 (25.88, −25.77) | −8.06 (23.09, −25.26) | −12.52 (17.08, −30.33) | −3.91 (13.89, −27.81) | −14.36 (14.01, −28.72) |
| RETN | −0.39 (32.85, −30.26) | −10.61 (5.99, −28.49) | −14.82 (7.65, −39.54) | −20.16 (14.81, −35.87) | −15.09 (11.87, −24.74) |
| TNFRSF4 | −3.65 (15.07, −20.77) | −7.54 (7.86, −23.17) | −9.27 (11.71, −20.94) | −9.03 (5.54, −22.90) | −7.54 (8.36, −23.13) |
| TRANCE | 0.28 (23.61, −20.51) | 5.77 (28.54, −14.57) | −9.03 (28.00, −22.67) | −4.15 (19.94, −30.71) | −3.39 (25.50, −13.05) |

Proteins with the largest median difference between pretreatment and 12 weeks post anti-MAdCAM treatment compared to pretreatment and week 12 of the placebo arm are summarized in Table 13. Shown is the median change and quartile 1, quartile 3 values for each group. The data are analyzed for biomarkers of response using statistical modeling.

In addition, in collaboration with the IBD node, additional value can be extracted by mining of the data in comparison to other IBD datasets, to further our understanding of this disease, of known or novel therapeutic protein evaluations of these samples are proposed.

In particular, three protein biomarkers—fecal calprotectin, sMAdCAM, and hsCRP, are particularly predictive of patients' responses to treatment. The protein levels change in response to treatment and changes in protein concentrations from baseline to week 4 or baseline to week 12 correlate to clinical endpoints (e.g. clinical response at week 12), and can be used to predict clinical response or to identify patient sub-populations particularly suitable for this treatment.

TABLE 13

Median (Q3-Q1) Change from Baseline to Week 12

| Analyte | Placebo | 7.5 | 22.5 | 75 | 225 |
|---|---|---|---|---|---|
| AR | −3.90 (38.05, −27.26) | −0.81 (29.75, −27.97) | −11.52 (6.65, −30.90) | −11.28 (9.34, −37.48) | −6.36 (25.97, −32.12) |
| CXCL11 | −4.02 (44.22, −29.39) | −13.82 (24.79, −45.53) | −11.49 (15.95, −31.02) | −17.59 (5.45, −50.02) | −8.28 (33.53, −39.93) |
| CXCL13 | 4.04 (34.29, −20.35) | −9.17 (33.74, −36.63) | −14.92 (11.17, −35.17) | −19.13 (16.65, −39.70) | 0.09 (36.23, −24.46) |
| EPO | 0.00 (29.87, −18.57) | −8.33 (16.67, −32.10) | −8.67 (4.28, −39.22) | −12.24 (7.63, −50.34) | 0.00 (19.43, −29.97) |
| FGF-21 | 3.14 (104.21, −42.53) | −14.94 (56.76, −59.23) | −10.87 (50.72, −46.12) | −28.47 (38.39, −53.07) | −12.94 (40.77, −44.02) |
| GH | −2.72 (90.77, −60.85) | −3.49 (148.16, −52.25) | −28.80 (47.88, −65.95) | −17.44 (70.68, −72.99) | 2.00 (289.50, −46.32) |
| IL-6 | 2.70 (65.41, −29.83) | −7.58 (37.48, −37.93) | −8.34 (40.83, −41.95) | −10.81 (41.33, −38.34) | 8.46 (47.52, −26.48) |
| IL-7 | 7.82 (25.16, −21.08) | −6.07 (27.92, −22.81) | −12.46 (15.57, −25.44) | −7.68 (10.89, −34.13) | −4.96 (27.23, −25.69) |
| IL-8 | −5.99 (32.25, −42.53) | −12.47 (36.70, −34.79) | −3.98 (23.66, −30.93) | −26.05 (10.03, −38.57) | −10.72 (35.40, −26.76) |
| MMP-1 | 8.32 (25.24, −20.78) | −13.94 (0.56, −30.32) | −16.99 (−0.46, −35.64) | −19.10 (−0.42, −40.72) | −5.85 (9.26, −24.47) |
| MMP-10 | −5.51 (15.56, −27.01) | −4.35 (56.89, −26.81) | −15.44 (0.22, −36.73) | −17.44 (13.49, −41.79) | −15.96 (18.43, −35.37) |
| MMP-3 | −1.44 (21.54, −22.11) | −5.13 (27.04, −20.34) | −15.41 (8.21, −28.68) | −9.29 (13.38, −31.32) | −9.87 (13.78, −27.95) |
| OSM | −7.91 (21.34, −34.03) | −14.16 (46.45, −40.66) | −25.57 (8.70, −48.30) | −17.47 (27.55, −47.53) | −18.97 (11.26, −42.30) |
| PTPN22 | −3.41 (47.62, −35.30) | −5.30 (40.20, −37.23) | −8.91 (25.42, −44.02) | −16.54 (27.03, −45.28) | −12.12 (48.40, −42.82) |
| REG-4 | 5.52 (17.65, −15.43) | −6.12 (22.29, −14.69) | −9.80 (8.67, −20.02) | −9.53 (17.44, −27.27) | 1.29 (26.69, −16.90) |
| RETN | 1.98 (28.28, −35.97) | −3.32 (31.14, −25.40) | −13.08 (11.71, −32.64) | −10.31 (24.38, −36.80) | −9.73 (16.54, −28.48) |
| VEGF-A | 2.35 (24.11, −23.81) | −7.21 (17.15, −23.86) | −8.57 (8.32, −26.15) | −10.22 (17.22, −32.92) | −2.14 (22.37, −17.17) |

Figure 8:
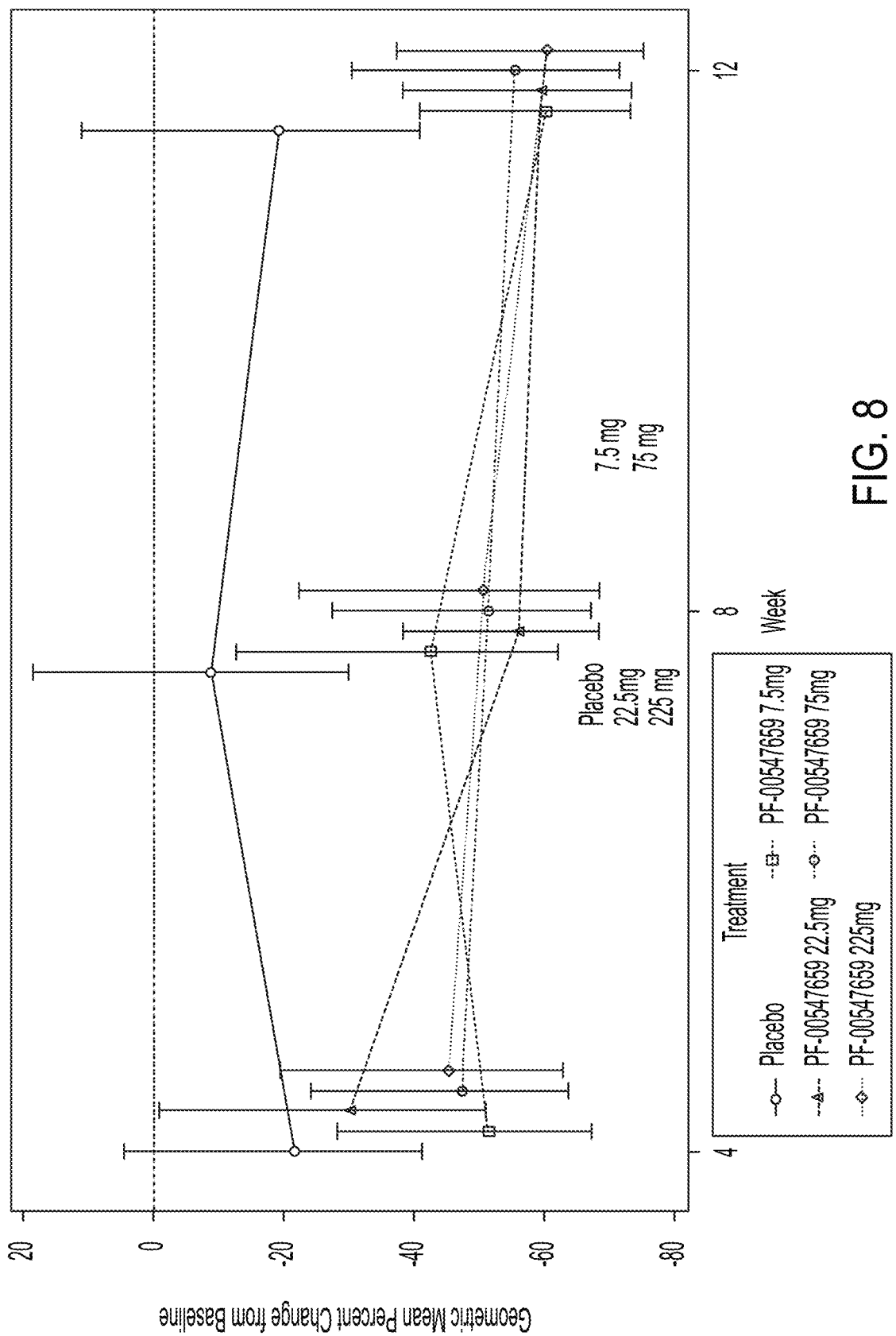

Fecal Calprotectin. The estimates (and 90% CI) for change from baseline in fecal calprotectin data are summarized in FIG. 8. There was robust decline in the fecal calprotectin values from baseline for the active arms at week 4 which continued to decline at week 8 and 12. As evident from FIG. 8 the placebo arm showed less decline compared with active arms. At week 12, geometric means for % change from baseline were −19% (decrease), −60% (decrease), −59% (decrease), −55% (decrease), and −60% (decrease) for placebo, 7.5 mg, 22.5 mg, 75 mg and 225 mg dose, respectively.

Figure 9:
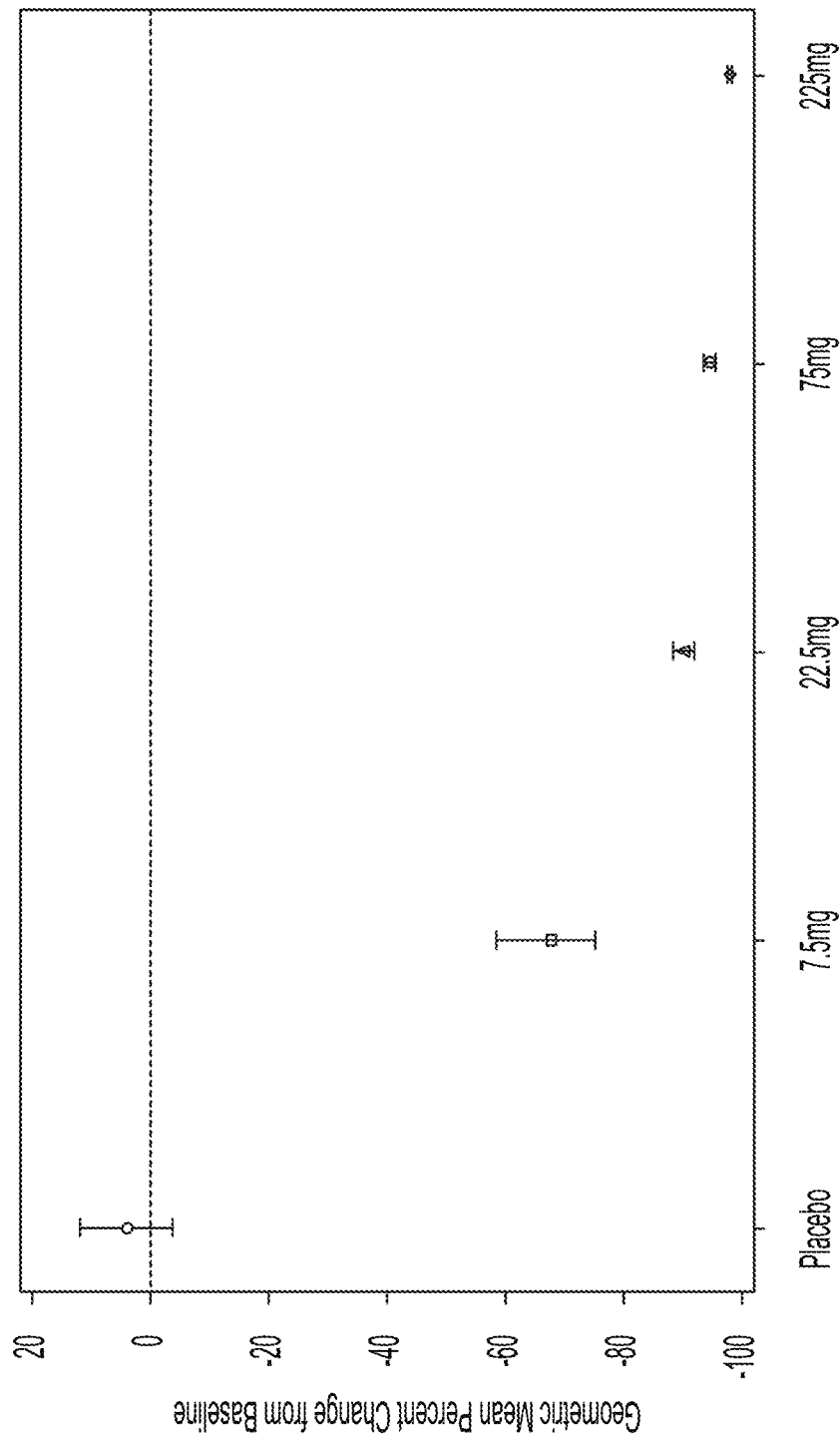
Figure 10:
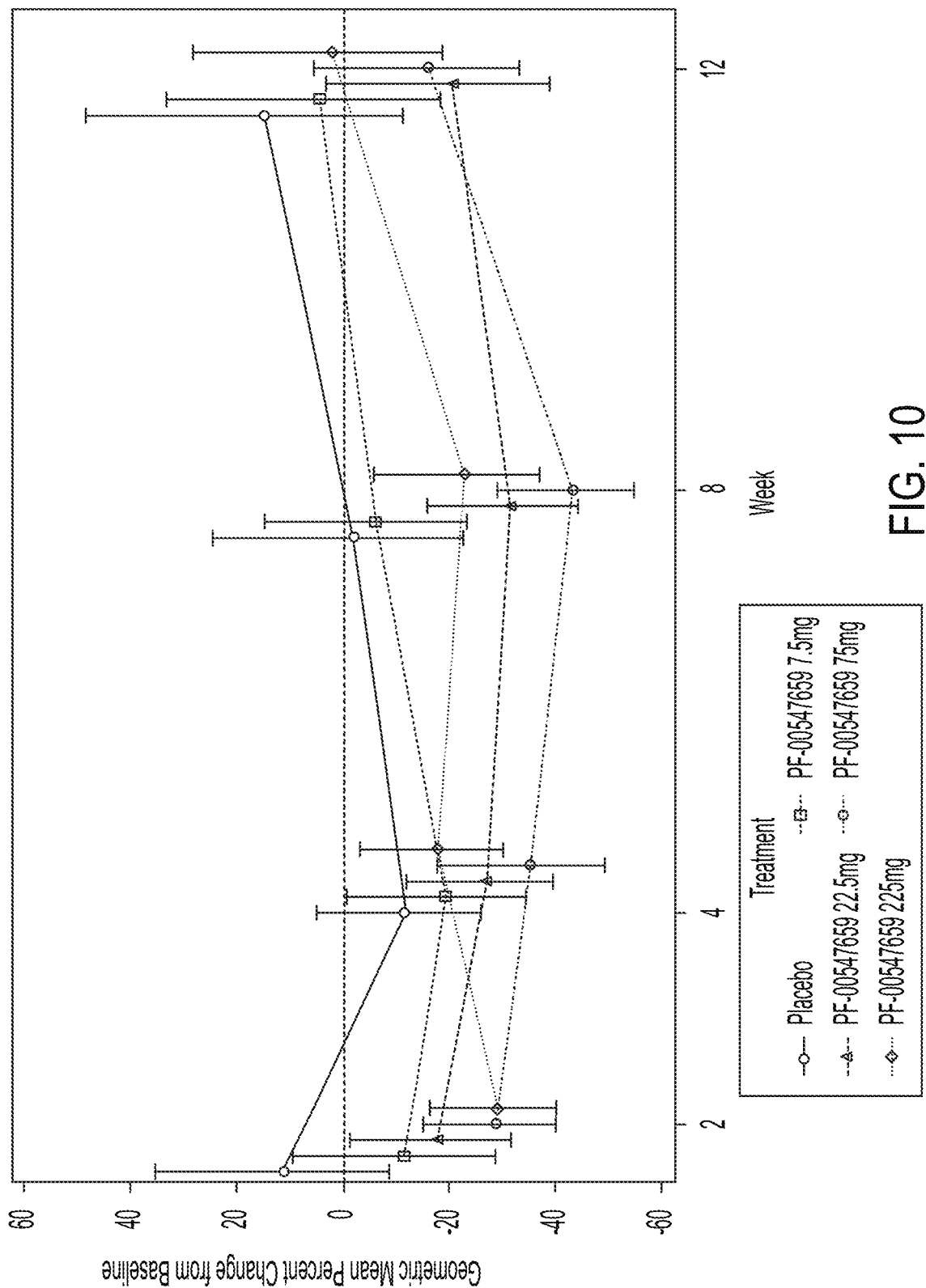
Figure 11A:
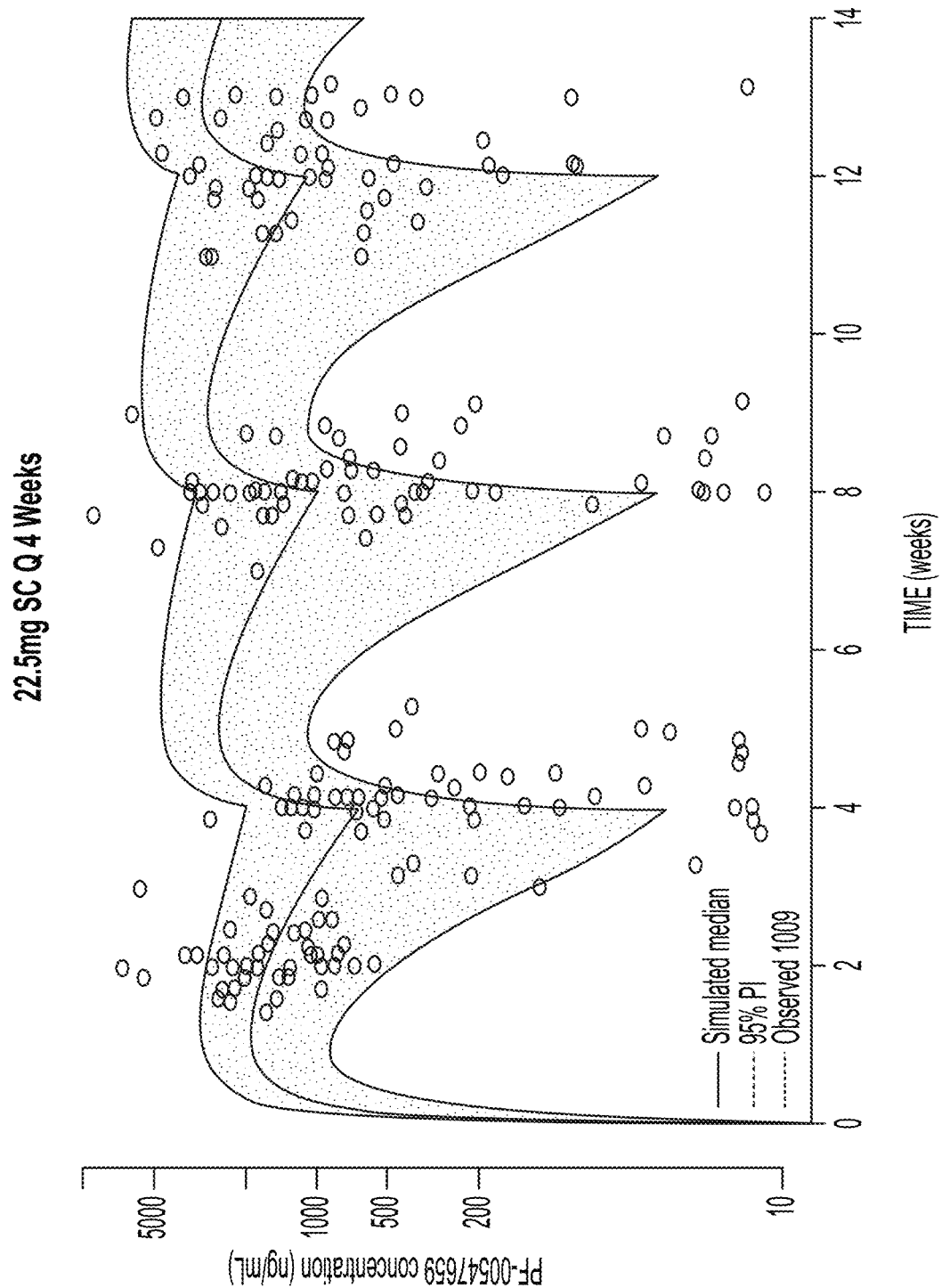
FIG. 11A, FIG. 11B, FIG. 11C, and FIG. 11D: Observed (red) serum mAb 7.16.6 concentrations compared to model predictions (black, median and 95% prediction interval), by treatment group.
Figure 11B:
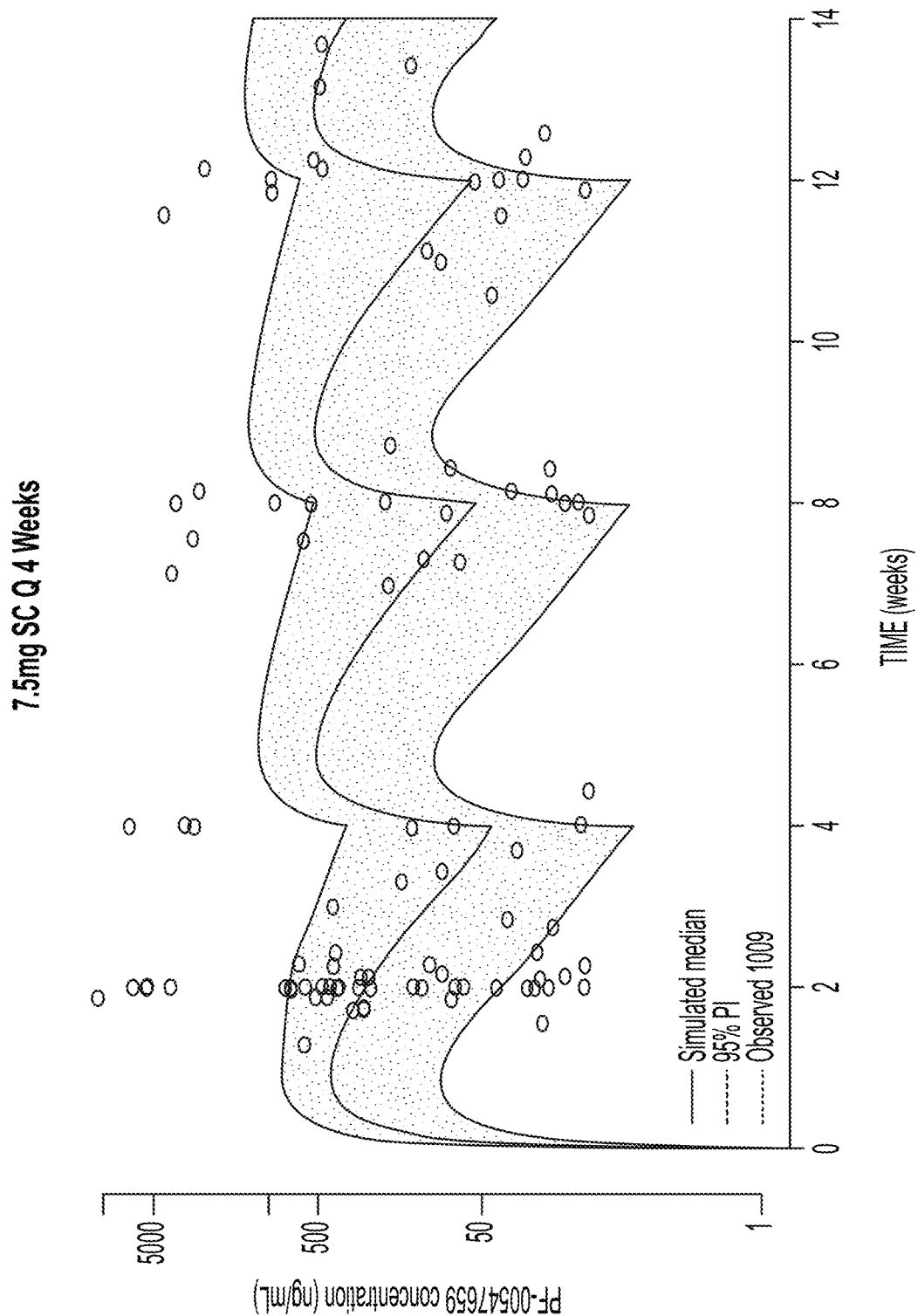
Figure 11C:
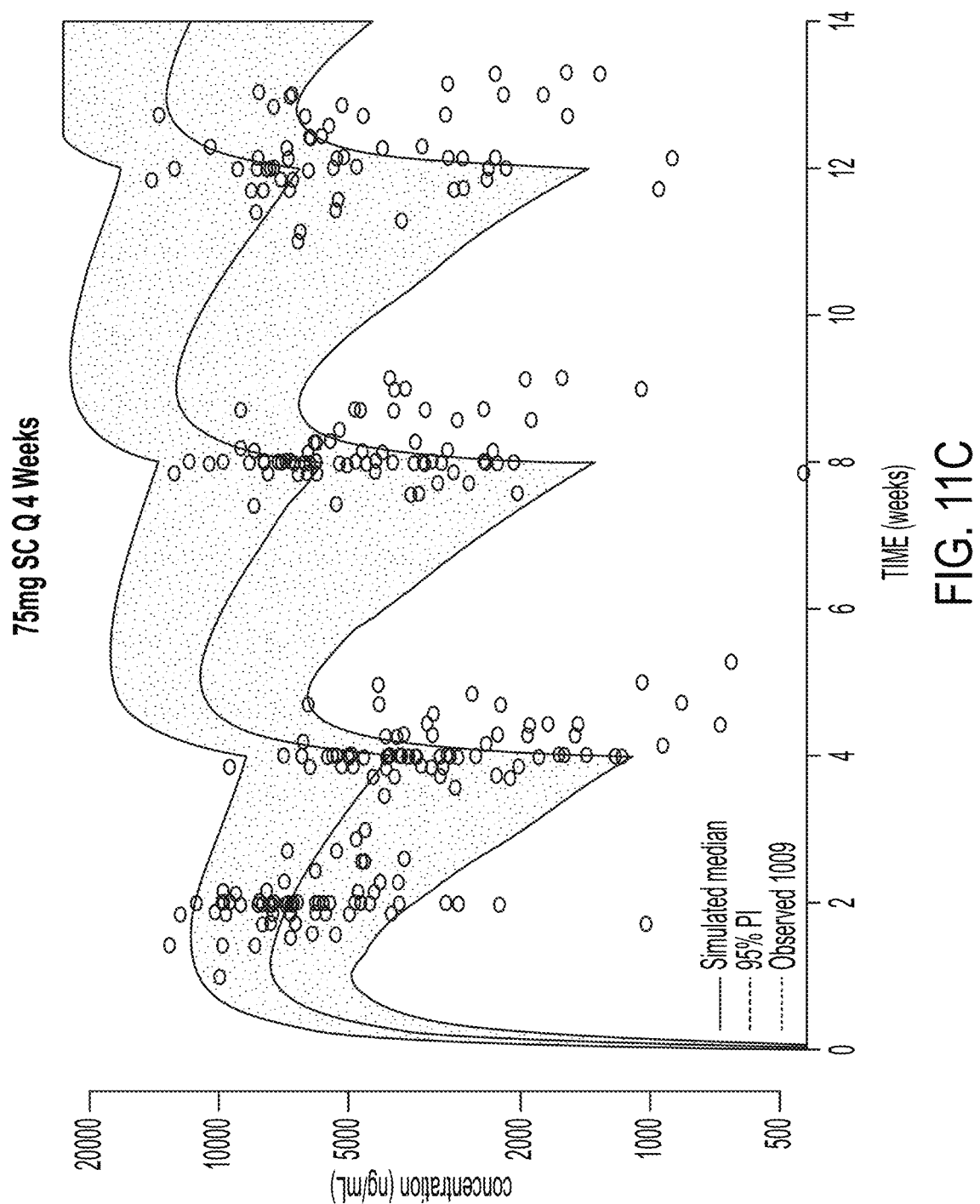
Figure 11D:
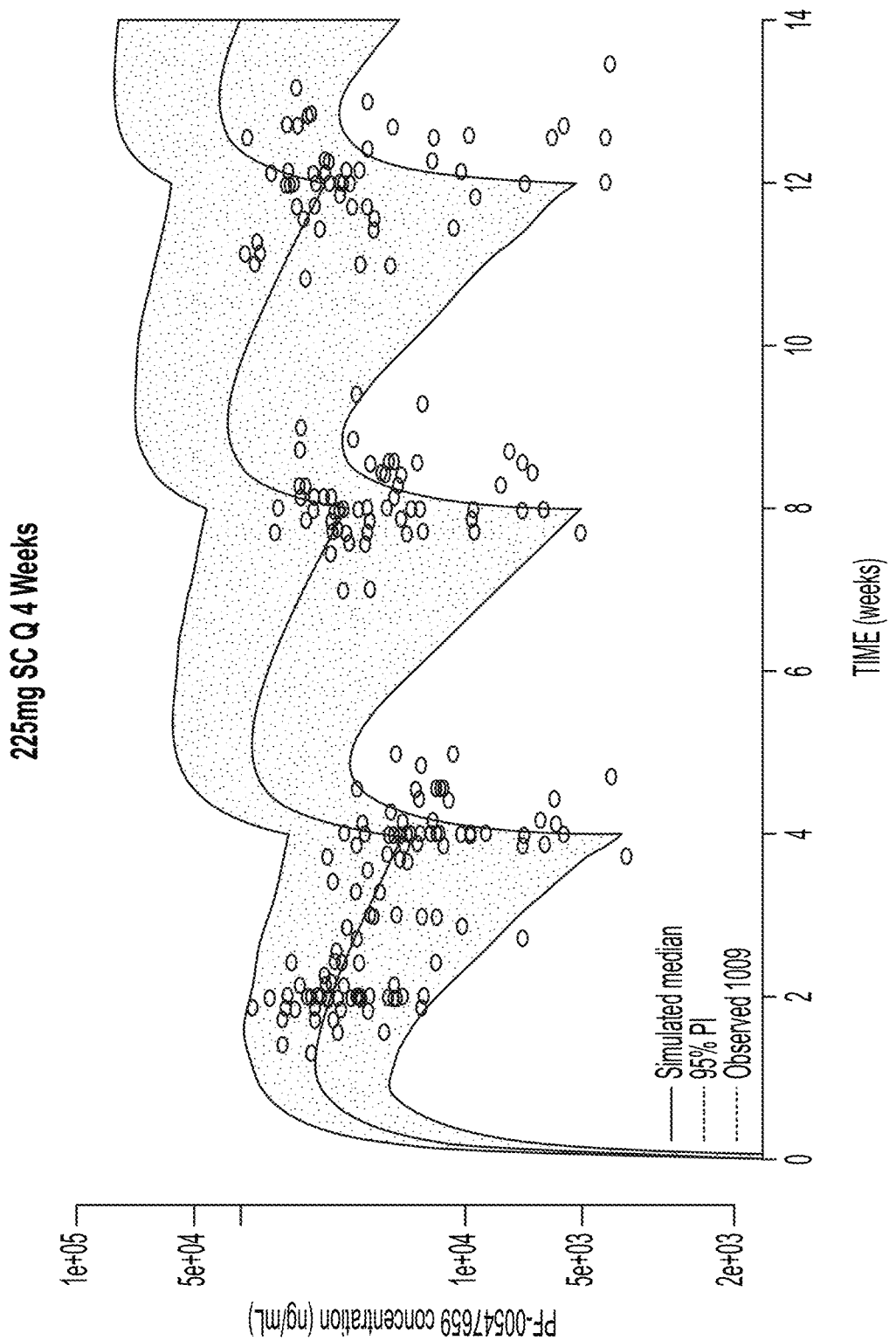

Soluble MAdCAM (sMAdCAM). The estimates (and 90% CI) for change from baseline in sMAdCAM data are summarized in FIG. 9. Consistent with predictions during the design of the study, sMAdCAM showed very robust and monotonic decline across the dose range, levelling off at doses >=22.5 mg. At week 12, geometric means for % change from baseline were 4% (increase), −68% (decrease), −90% (decrease), −94% (decrease), and −98% (decrease), for placebo, 7.5 mg, 22.5 mg, 75 mg, and 225 mg dose, respectively.

hsCRP. The estimates (and 90% CI) for change from baseline in hsCRP data are summarized in FIG. 10. There was some decline in the hsCRP values from baseline for the active arms at week 4 which continued to decline through week 8, except for the 7.5 mg dose group, which did not show much change. Active treatment arms showed a trend to return towards baseline by week 12, although consistent with clinical findings, the greatest and most persistent reductions were observed in the 22.5 mg and 75 mg groups. As evident from FIG. 2A, FIG. 2B, FIG. 2C, and FIG. 2D, the placebo arm did not show much change over time. At week 12, geometric means for percent change from baseline were 15% (increase), 5% (increase), −20% (reduction), −16% (reduction), and 2% (increase) for placebo, 7.5 mg, 22.5 mg, 75 mg, and 225 mg dose, respectively.

8.2 RNA Biomarkers Identified by Gene Expression Profiling for MAdCAM UC

Background. Blood and tissue biopsy samples were collected at various time points in all dose groups and used to measure the global transcriptome using a RNA-seq technology platform. RNA-seq is an unbiased gene expression profiling technology that allows the simultaneous and unbiased measurement of transcript levels of virtually all transcripts present in a given cell or tissue type. Transcriptomes were sequenced at a read depth of ~40 Million paired end reads per sample which allows for a detailed transcript analysis of >15,000 genes including the respective isoforms. Samples taken prior to treatment were compared to samples taken 4 weeks and 12 weeks after treatment and a statistical analysis was performed to identify transcript changing at the various dose levels across these sampling timepoints. Biomarkers that predict response to treatment are analyzed by correlating the starting concentration of a single or multiple transcripts from samples taken prior to treatment, as well as the change in the transcript expression level from baseline to 4 weeks or 12 weeks. These gene expression data are also analyzed together with data from protein and cell population data.

Methods. Blood and tissue RNA from patients enrolled in the MAdCAM UC study were measured from samples taken prior to treatment and at 4 weeks and 12 weeks during the dosing period of treatment using the Illumina RNA-seq technology platform that consists of a TruSeq mRNA stranded sequencing library generation followed by an analysis of this library using a Illumina HiSeq 2000 or 4000 series sequencer. In total, transcript expression in blood was measured for 320 patients at baseline and week 12. 256 patients from this group also had transcript analyses performed at week 4. For the tissue biopsy sample analysis 126 subjects had inflamed tissue biopsies analyzed at the screening visit and at week 12.

Results. Many transcripts show a different gene expression level at 4 weeks and 12 weeks during the dosing period of the anti-MAdCAM treatment compared to starting gene expression values at baseline (or screening visit). See, Table 15. In particular, expression change in CCR9 (e.g., expression change at week 12 from baseline) is believed to correlates with clinical efficacy.

| GeneID | HUGO_geneid | GeneID | HUGO_geneid | GeneID | HUGO_geneid | GeneID | HUGO_geneid |
|---|---|---|---|---|---|---|---|
| ENSG00000173585 | CCR9 | ENSG00000139514 | SLC7A1 | ENSG00000214105 | CTD-2116F7 | ENSG00000205502 | C2CD4B |

-continued

| GeneID | HUGO_geneid | GeneID | HUGO_geneid | GeneID | HUGO_geneid | GeneID | HUGO_geneid |
|---|---|---|---|---|---|---|---|
| ENSG00000122882 | ECD | ENSG00000072134 | EPN2 | ENSG00000179348 | GATA2 | ENSG00000269290 | RP11-869B15 |
| ENSG00000228061 | Z83001 | ENSG00000186469 | GNG2 | ENSG00000242611 | AC093627 | ENSG00000134709 | HOOK1 |
| ENSG00000211793 | TRAV9-2 | ENSG00000261087 | KB-1460A1 | ENSG00000231748 | RP11-227H15 | ENSG00000158715 | SLC45A3 |
| ENSG00000096070 | BRPF3 | ENSG00000128833 | MYO5C | ENSG00000202314 | SNORD6 | ENSG00000239305 | RNF103 |
| ENSG00000241484 | ARHGAP8 | ENSG00000140743 | CDR2 | ENSG00000151136 | BTBD11 | ENSG00000006210 | CX3CL1 |
| ENSG00000199933 | Y_RNA | ENSG00000214797 | RP11-1036E20 | ENSG00000242444 | RP11-320N7 | ENSG00000155016 | CYP2U1 |
| ENSG00000237361 | RP11-269C23 | ENSG00000130950 | NUTM2F | ENSG00000176928 | GCNT4 | ENSG00000153064 | BANK1 |
| ENSG00000116212 | LRRC42 | ENSG00000143554 | SLC27A3 | ENSG00000252071 | snoU13 | ENSG00000173208 | ABCD2 |
| ENSG00000042980 | ADAM28 | ENSG00000178055 | PRSS42 | ENSG00000110719 | TCIRG1 | ENSG00000235652 | RP11-545I5 |
| ENSG00000013288 | MAN2B2 | ENSG00000088035 | ALG6 | ENSG00000254287 | RP11-44K6 | ENSG00000155719 | OTOA |
| ENSG00000152894 | PTPRK | ENSG00000163751 | CPA3 | ENSG00000180771 | SRSF8 | ENSG00000172575 | RASGRP1 |
| ENSG00000135318 | NT5E | ENSG00000069188 | SDK2 | ENSG00000085788 | DDHD2 | ENSG00000101134 | DOK5 |
| ENSG00000258742 | RP11-862G15 | ENSG00000107771 | CCSER2 | ENSG00000073146 | MOV10L1 | ENSG00000169762 | TAPT1 |
| ENSG00000173114 | LRRN3 | ENSG00000153902 | LGI4 | ENSG00000170989 | S1PR1 | ENSG00000025800 | KPNA6 |
| ENSG00000199032 | MIR425 | ENSG00000258096 | RP11-474P2 | ENSG00000198919 | DZIP3 | ENSG00000164466 | SFXN1 |
| ENSG00000211717 | TRBV10-1 | ENSG00000204632 | HLA-G | ENSG00000148468 | FAM171A1 | ENSG00000166707 | ZCCHC18 |
| ENSG00000225760 | RP11-365P13 | ENSG00000265263 | RP11-135L13 | ENSG00000268950 | AC114494 | ENSG00000156515 | HK1 |
| ENSG00000237990 | CNTN4-AS1 | ENSG00000104472 | CHRAC1 | ENSG00000181029 | TRAPPC5 | ENSG00000136504 | KAT7 |
| ENSG00000272379 | RP1-257A7 | ENSG00000185339 | TCN2 | ENSG00000253773 | KB-1047C11 | ENSG00000140009 | ESR2 |
| ENSG00000253293 | HOXA10 | ENSG00000163082 | SGPP2 | ENSG00000132388 | UBE2G1 | ENSG00000232274 | RP11-782C8 |
| ENSG00000235304 | RP11-265P11 | ENSG00000249459 | ZNF286B | ENSG00000247796 | CTD-2366F13 | ENSG00000268313 | AC119673 |
| ENSG00000022556 | NLRP2 | ENSG00000104918 | RETN | ENSG00000125826 | RBCK1 | ENSG00000082014 | SMARCD3 |
| ENSG00000198668 | CALM1 | ENSG00000259363 | CTD-2054N24 | ENSG00000133816 | MICAL2 | ENSG00000203401 | AC009061 |
| ENSG00000270457 | RP11-467C18 | ENSG00000115998 | C2orf42 | ENSG00000112782 | CLIC5 | ENSG00000174469 | CNTNAP2 |
| ENSG00000066405 | CLDN18 | ENSG00000227042 | RP6-1O2 | ENSG00000211788 | TRAV13-1 | ENSG00000171298 | GAA |
| ENSG00000261186 | RP11-341N2 | ENSG00000268205 | CTC-444N24 | ENSG00000142910 | TINAGL1 | ENSG00000168646 | AXIN2 |
| ENSG00000127152 | BCL11B | ENSG00000270674 | RP11-216F19 | ENSG00000114120 | SLC25A36 | ENSG00000119414 | PPP6C |
| ENSG00000070404 | FSTL3 | ENSG00000130489 | SCO2 | ENSG00000169228 | RAB24 | ENSG00000173918 | C1QTNF1 |
| ENSG00000159423 | ALDH4A1 | ENSG00000143457 | GOLPH3L | ENSG00000237505 | RP11-76N22 | ENSG00000106537 | TSPAN13 |
| ENSG00000140092 | FBLN5 | ENSG00000184307 | ZDHHC23 | ENSG00000132704 | FCRL2 | ENSG00000086189 | DIMT1 |
| ENSG00000229776 | C4B-AS1 | ENSG00000251606 | CTD-2215E18 | ENSG00000260093 | RP11-1E4 | ENSG00000171914 | TLN2 |
| ENSG00000271954 | RP11-427H3 | ENSG00000225407 | CTD-2384B11 | ENSG00000030582 | GRN | ENSG00000079691 | LRRC16A |
| ENSG00000169436 | COL22A1 | ENSG00000164543 | STK17A | ENSG00000238121 | LINC00426 | ENSG00000104660 | LEPROTL1 |
| ENSG00000151623 | NR3C2 | ENSG00000213853 | EMP2 | ENSG00000105270 | CLIP3 | ENSG00000134954 | ETS1 |
| ENSG00000174791 | RIN1 | ENSG00000145687 | SSBP2 | ENSG00000198954 | KIAA1279 | ENSG00000250548 | RP11-47I22 |
| ENSG00000186265 | BTLA | ENSG00000052126 | PLEKHA5 | ENSG00000235488 | JARID2-AS1 | ENSG00000076984 | MAP2K7 |
| ENSG00000177459 | C8orf47 | ENSG00000182511 | FES | ENSG00000158079 | PTPDC1 | ENSG00000188818 | ZDHHC11 |
| ENSG00000187416 | LHFPL3 | ENSG00000154479 | CCDC173 | ENSG00000198963 | RORB | ENSG00000129270 | MMP28 |

-continued

| GeneID | HUGO_geneid | GeneID | HUGO_geneid | GeneID | HUGO_geneid | GeneID | HUGO_geneid |
|---|---|---|---|---|---|---|---|
| ENSG00000101892 | ATP1B4 | ENSG00000155093 | PTPRN2 | ENSG00000030419 | IKZF2 | ENSG00000100065 | CARD10 |
| ENSG00000138617 | PARP16 | ENSG00000149308 | NPAT | ENSG00000068354 | TBC1D25 | ENSG00000158195 | WASF2 |
| ENSG00000261211 | RP1-80N2 | ENSG00000162129 | CLPB | ENSG00000211797 | TRAV17 | ENSG00000233125 | ACTBP12 |
| ENSG00000019995 | ZRANB1 | ENSG00000133639 | BTG1 | ENSG00000197111 | PCBP2 | ENSG00000119508 | NR4A3 |
| ENSG00000227215 | RP11-445L13__B | ENSG00000137502 | RAB30 | ENSG00000112182 | BACH2 | ENSG00000186591 | UBE2H |
| ENSG00000099204 | ABLIM1 | ENSG00000271783 | RP11-533E19 | ENSG00000006432 | MAP3K9 | ENSG00000200227 | RNA5SP197 |
| ENSG00000242861 | RP11-285F7 | ENSG00000230928 | RP11-34A14 | ENSG00000203364 | RP11-370F5 | ENSG00000103343 | ZNF174 |
| ENSG00000211879 | TRAJ10 | ENSG00000105472 | CLEC11A | ENSG00000233225 | AC004987 | ENSG00000259728 | LINC00933 |
| ENSG00000269018 | AP001362 | ENSG00000154511 | FAM69A | ENSG00000100979 | PLTP | ENSG00000122741 | DCAF10 |
| ENSG00000177425 | PAWR | ENSG00000196323 | ZBTB44 | ENSG00000012983 | MAP4K5 | ENSG00000185736 | ADARB2 |
| ENSG00000207585 | MIR181D | ENSG00000211880 | TRAJ9 | ENSG00000125868 | DSTN | ENSG00000113263 | ITK |

8.3 Cell Biomarkers Identified by FACS.

B7 integrin FACS assay. The frequency and expression of surface B7 marker in lymphocyte subsets are assessed by a whole blood FACS assay. Aliquots (100 μL) of sodium heparin blood are incubated with 30 uL of the antibody cocktail (CD45RO-FITC, B7-integrin or rat IgG2a isotype control-PE, CD4-PerCPCy5.5, CD27-APC, and CD3-APC-H7; all from BD) at room temperature for 30 minutes. To each tube 1 mL of 1×BD PharmLyse solution are added, shaken by hand and incubated for 30 minutes at room temperature whilst being protected from light for 30 minutes. Lyzed blood is acquired by FACSCanto II within 2 hours of preparation. Cytometer is set to acquire most of sample per tube. Expression of surface B7 protein in the subset is quantified as standard unit MESF (Molecules of Equivalent Soluble Fluorochrome) with BD QuantiBrite-PE as a calibrator.

MAdCAM is expressed on the endothelial cells of the gut and on gut-associated lymphoid tissue. Anti-MAdCAM blocks the interaction between β7+ expressing cells and the ligand MAdCAM, thereby blocking extravasation of β7+ expressing cells from circulation to the gut. Treatment with anti-MAdCAM therefore increases α4β7+ cells in the circulation. Blood samples are taken at baseline, Week 8 and Week 12, and α4β7+ central memory T cells are measured by fluorescence activated cell sorting (FACS). Percent 07+ data are reported as % CD4+ expressing cells that also expressed b7, absolute number (cells/μL) and MESF (Molecules of Equivalent Soluble Fluorochrome) which is the unit measure of 07 protein expression on central memory T cells are also measured. The FACS parameters are analyzed using a linear mixed model using change from baseline as response, and treatment, status of anti-TNF experience, concomitant IS therapy, baseline, visit, and treatment by visit interaction as fixed effects and subjects as random effect. Circulating b7+ central memory CD4+T-lymphocytes are believed to increase at Weeks 8 and 12 in anti-MAdCAM treated patients in a dose-dependent manner. The fold changes for % β7+ central memory T cell are expected to be statistically significant for all doses at Weeks 8 and 12. Increases in the absolute number of β7+ central memory T cells and in MESF are also expected to be significantly higher for all doses of anti-MAdCAM groups compared with placebo at Weeks 8 and 12.

8.4 Genetic Biomarkers Identified by Genotyping.

Genome-wide genotype data was generated for all subjects using the Pfizer custom Illumina array. This custom chip is largely based on the Illimuna OmniExpressExome chip design that aims to covers most exonic variation that exists in the genome. Additional content beyond the OmniExpressExome chips aims to covers additional variants known to be associated with disease in multi-ethnic cohorts based on previous studies. Both sample-level and genotype-level quality control will be conducted based on the following criteria:

Sample-Level
  Sample call rate check—Samples with <95% call rate are removed.
  Sample gender check—Samples with genders discordant to the self-reported gender are removed. Gender is defined by the homozygosity rate on the X chromosome. For males, homozygosity rate must be >=0.8, and for females, this should be <=0.2. Typically, fewer than 0.5% of samples have gender mismatch.
  Sample heterozygosity rate—Samples with heterozygosity rate >3 standard deviations above the mean are removed.
  Sample relatedness check—For pairs with a PI_HAT score >0.1875, the sample with the lower call rate is removed.
Genotype-Level
  SNP call rate check: SNPs with <95% call rate will be removed.
  SNP marker duplicate check: Duplicate SNPs on the chip are removed. The SNP with the higher call rate is retained.

Analysis of Genotypic Data. Two genetic analyses are conducted. First, candidate SNPs are analyzed to assess the association with clinical efficacy at week 12. In particular, rs11171739 is analyzed, as rs11171739 is a SNP that has been suggested as potentially associated with expression levels of the MADCAM1 gene. Second, a gene score is constructed based on a combination of top genetic variants known to be associated with Ulcerative Colitis based on publically available data, to test for an association of this gene score with clinical response to MadCAM. The gene score is calculated based on a weighted sum of risk alleles for UC. Weights will be based on known effect size of each risk allele. A gene score is calculated for each individual subject and then tested for association in a linear regression model for various measures of clinical efficacy.

All analyses include ancestry as a covariate to avoid detection of signals that are associated with ancestry rather than drug response. Ancestry is represented by a quantitative vector for each subject representing their values along a number of principal components and included in the above regression model as a substitution for race as covariates.

Example 9 Pharmacokinetics, Target Coverage and Anti-Drug Antibody

Exposure was consistent with that observed in the FIH study (A7281001, Ulcerative Colitis) and adequately predicted by the preliminary population pharmacokinetic model describing target mediated drug disposition.

Mean observed Ctrough values at week 12 were 435 ng/ml, 1334 ng/ml, 5567 ng/ml, and 19860 ng/ml at doses of 7.5 mg, 22.5 mg, 75 mg, and 225 mg, respectively. These serum concentrations corresponded to suppression of soluble MAdCAM (geometric mean percent change from baseline at week 12) of 68, 90, 94, and 98 respectively, consistent with model predictions during the design of the study.

Generally, PK levels serum concentrations in the present Study were similar to those observed in separate, Crohn's disease study, using the same therapeutic antibody at corresponding doses.

Of 758 ADA samples from 282 subjects on active treatment analyzed up to week 12, 709 were reported negative. Forty-nine ADA samples from 29 subjects were confirmed positive; 7 subjects on 7.5 mg, 6 subjects on 22.5 mg, 9 subjects on 75 mg, and 7 subjects on 225 mg. Twelve subjects had confirmatory positive ADAs at baseline. Nine subjects out of the 12 subjects with confirmatory positive ADAs at baseline were positive post baseline (3 subjects on 7.5 mg, 1 subject on 22.5 mg, 4 subjects on 75 mg, and 1 subject on 225 mg), with no indication of treatment boosted ADA response (i.e., greater ADA titer post-treatment as compared with Baseline). Out of the 709 samples reported negative, 396 (~56%) were considered inconclusive and 313 (~44%) were confirmed negative based on measured serum concentrations being >LLOQ (>10 ng/mL) and BLQ (<10 ng/mL), respectively. Note: out of the 313 values BLOQ, 245 were pre dose measurements.

The overall confirmatory positive rate was approximately 6.4% with titers generally low and close to the cut-off (4.64), with none being higher than 11.86.

Preliminary evaluation of PK data in subjects with confirmatory positive ADAs post-baseline indicate no discernable effect of positive ADAs on exposure, safety or efficacy. This evaluation was conducted based on all available data from subjects with post-baseline confirmatory positive ADAs (n=26).

Example 10 Crohn's Disease

Background. Inhibition of white blood cell (WBC) translocation from the bloodstream to the intestine is a promising new approach to the management of Inflammatory Bowel Disease. OPERA was a randomized, multicenter double-blind, placebo-controlled study of safety and efficacy of mAb 7.16.6 in subjects with Crohn's disease (CD).

Methods. Adults ages 18-75, with active moderate to severe CD (CDAI 220-450) and a history of failure or intolerance to anti-TNF and/or immunosuppressant drugs were eligible if they had hsCRP >3.0 mg/L and ulcers on colonoscopy. Subjects were randomized to placebo, 22.5 mg, 75 mg or 225 mg arms. The primary end point was CDAI-70 response at week 8 or 12. Secondary end points were remission and CDAI-100 response and safety. Disease biomarkers studied were blood $\beta7+CD4+$ central memory T-cell level (frequency and $\beta7$ expression) by FACS, CRP, and soluble MAdCAM.

Results. 267 subjects were enrolled. While CDAI-70 response was not significantly different from placebo for any treatment, remission appears to be higher in subjects with higher baseline CRP (CRP >18). The median CRP at baseline was 18 mg/L across all groups. Soluble MAdCAM in treated, but not control subjects decreased significantly at week 2 compared with baseline, in a dose-related manner, and remained low during the study. Circulating $07+CD4+$ central memory T-lymphocytes increased at weeks 8 and 12, in PF treated subjects in a dose-dependent manner. Baseline characteristics and subset of efficacy results are in Table 14.

TABLE 14

| Patient Characteristics and subset of Efficacy Results at Week 12 | | | | |
|---|---|---|---|---|
| Value | Placebo | 22.5 mg | 75 mg | 225 mg |
| N | 63 | 67 | 64 | 68 |
| Age, yrs (mean sd) | 34.4 (11.1) | 37.0 (13.1) | 34.7 (10.6) | 35.9 (1.0) |
| CD Duration years (median, range) | 10.5 (.8-51.8) | 11.5 (1.9-38.1) | 8.2 (0-36.5) | 12.4 (0-30.5) |
| Baseline CDAI (mean, sd) | 313 (61) | 308 (71) | 324 (65) | 316 (64) |
| *Response 70 week 12 (se) | 59% (9.0%) | 62% (9.0%) | 65% (9.0%) | 58% (8.9%) |
| *Remission week 12 (se) | 23% (8.3%) | 27% (9.1%) | 28% (9.7%) | 29% (9.3%) |
| # Remission week 12 with baseline CRP >18 (se) | 14% (7.6%) | 37% (11%) | 24% (9.2%) | 39% (10.2%) |

*analysis using a generalized linear mixed model;
reporting proportions for subset analysis.

mAb 7.16.6 appears safe and well-tolerated in this patient population. Most common adverse events were related to the underlying disease, with no evidence of a dose response in any AE group.

Conclusions. The primary endpoint was not met because of a high placebo response, mAb 7.16.6 was pharmacologically active as shown by a dose-related increase in circulating $\beta7+$ T lymphocytes and a sustained dose-related decrease in MAdCAM. Subjects with higher baseline CRP had the best response to mAb 7.16.6. No safety signal was observed in this study.

Example 11 RNA Biomarkers for Crohn's Disease

Blood-derived RNA from patients enrolled in the MAdCAM CD study were measured from samples taken prior to treatment and at 12 weeks during the dosing period of treatment using the Illumina RNA-seq technology platform that consists of a TruSeq mRNA stranded sequencing library generation followed by an analysis of this library using a Illumina HiSeq 2000 or 4000 series sequencer. In total, transcript expression in blood was measured for 91 patients at baseline and week 12.

Many transcripts show a different gene expression level at 12 weeks during the dosing period of the anti-MAdCAM treatment compared to starting gene expression values at baseline. Transcripts for the statistically 200 most significant changes across the different dose levels between baseline and 12 weeks post anti-MAdCAM treatment are summarized in Table 16. Shown is the Average fold-change (AveFC) at each dose level followed by the significance of change across the treatment doses (PValueTrt). The first two columns show the Ensemble GeneID and the HUGO Gene Nomenclature Committee (HGNC) GeneID, respectively.

TABLE 16

| GeneID | HUGO_geneid | Ave FCPIc | Ave FC22.5 mg | Ave FC75 mg | Ave FC225 mg | PValueTrt |
|---|---|---|---|---|---|---|
| ENSG00000173585 | CCR9 | 1.03 | 2.78 | 2.8 | 3.72 | 1.09E−06 |
| ENSG00000122882 | ECD | 1.01 | 1.15 | 1.17 | 1.26 | 0.000246618 |
| ENSG00000228061 | Z83001 | 0.89 | 0.76 | 1.03 | 2.21 | 0.000486282 |
| ENSG00000211793 | TRAV9-2 | 0.96 | 1.23 | 1.25 | 1.54 | 0.000523789 |
| ENSG00000096070 | BRPF3 | 0.94 | 1.11 | 1.09 | 1.12 | 0.000685442 |
| ENSG00000241484 | ARHGAP8 | 1.07 | 0.71 | 2.33 | 0.94 | 0.000696011 |
| ENSG00000199933 | Y_RNA | 1.2 | 0.4 | 1.11 | 0.99 | 0.000756798 |
| ENSG00000237361 | RP11-269C23 | 1.36 | 0.4 | 1.52 | 0.81 | 0.000774542 |
| ENSG00000116212 | LRRC42 | 0.94 | 1.02 | 1.1 | 1.06 | 0.000859972 |
| ENSG00000042980 | ADAM28 | 0.99 | 1.49 | 1.18 | 1.32 | 0.001007256 |
| ENSG00000013288 | MAN2B2 | 0.95 | 1.08 | 1.08 | 1.06 | 0.001067193 |
| ENSG00000152894 | PTPRK | 0.89 | 1.58 | 1.64 | 1.67 | 0.001260717 |
| ENSG00000135318 | NT5E | 0.95 | 1.48 | 1.36 | 1.46 | 0.001263122 |
| ENSG00000258742 | RP11-862G15 | 0.73 | 1.54 | 2.14 | 1.5 | 0.001420644 |
| ENSG00000173114 | LRRN3 | 0.99 | 1.47 | 1.65 | 1.96 | 0.001531031 |
| ENSG00000199032 | MIR425 | 0.79 | 1.7 | 1.99 | 1.27 | 0.001780671 |
| ENSG00000211717 | TRBV10-1 | 0.64 | 1.66 | 1.15 | 1.79 | 0.001916056 |
| ENSG00000225760 | RP11-365P13 | 0.75 | 1.32 | 1.52 | 2.12 | 0.001961883 |
| ENSG00000237990 | CNTN4-AS1 | 0.43 | 1.97 | 0.78 | 1.28 | 0.002022301 |
| ENSG00000272379 | RP1-257A7 | 0.85 | 1.19 | 1.04 | 1.15 | 0.002148923 |
| ENSG00000253293 | HOXA10 | 1.24 | 0.57 | 1.78 | 1.74 | 0.002166659 |
| ENSG00000235304 | RP11-265P11 | 0.85 | 3.08 | 0.99 | 1.6 | 0.00222768 |
| ENSG00000022556 | NLRP2 | 0.85 | 1.1 | 1.19 | 1.2 | 0.002261611 |
| ENSG00000198668 | CALM1 | 1.01 | 1.07 | 1.08 | 1.17 | 0.002273075 |
| ENSG00000270457 | RP11-467C18 | 0.77 | 0.73 | 1.78 | 1.04 | 0.002373273 |
| ENSG00000066405 | CLDN18 | 1.29 | 1.14 | 0.64 | 0.41 | 0.002517879 |
| ENSG00000261186 | RP11-341N2 | 0.62 | 1.52 | 1.52 | 1.68 | 0.002548039 |
| ENSG00000127152 | BCL11B | 1.04 | 1.27 | 1.43 | 1.55 | 0.002616038 |
| ENSG00000070404 | FSTL3 | 1.22 | 0.86 | 0.9 | 0.91 | 0.002644189 |
| ENSG00000159423 | ALDH4A1 | 1.23 | 0.98 | 1.11 | 0.99 | 0.002683581 |
| ENSG00000140092 | FBLN5 | 0.96 | 1.37 | 1.15 | 1.51 | 0.002690708 |
| ENSG00000229776 | C4B-AS1 | 0.67 | 0.95 | 1.99 | 1.05 | 0.002797063 |
| ENSG00000271954 | RP11-427H3 | 1.01 | 1.14 | 1.21 | 1.27 | 0.002805773 |
| ENSG00000169436 | COL22A1 | 0.99 | 1.16 | 0.46 | 1.73 | 0.002848158 |
| ENSG00000151623 | NR3C2 | 1.06 | 1.38 | 1.45 | 1.61 | 0.002849267 |
| ENSG00000174791 | RIN1 | 1.28 | 0.92 | 0.95 | 1.04 | 0.002881754 |
| ENSG00000186265 | BTLA | 0.89 | 1.37 | 1.3 | 1.41 | 0.003047031 |
| ENSG00000177459 | C8orf47 | 0.7 | 1.81 | 1.79 | 2.06 | 0.003056796 |
| ENSG00000187416 | LHFPL3 | 0.95 | 0.7 | 2.15 | 1.26 | 0.003155561 |
| ENSG00000101892 | ATP1B4 | 0.84 | 0.81 | 0.96 | 1.86 | 0.003204539 |
| ENSG00000138617 | PARP16 | 0.93 | 1.1 | 1.07 | 1.11 | 0.003212319 |
| ENSG00000261211 | RP1-80N2 | 1.1 | 0.56 | 0.62 | 0.88 | 0.003213729 |
| ENSG00000019995 | ZRANB1 | 0.93 | 1.04 | 1.24 | 1.09 | 0.003471657 |
| ENSG00000227215 | RP11-445L13_B | 0.83 | 0.72 | 1.19 | 1.83 | 0.003762178 |
| ENSG00000099204 | ABLIM1 | 0.99 | 1.23 | 1.33 | 1.44 | 0.003812623 |
| ENSG00000242861 | RP11-285F7 | 0.92 | 1.2 | 1.18 | 1.27 | 0.00385391 |
| ENSG00000211879 | TRAJ10 | 0.9 | 1.22 | 1.15 | 1.55 | 0.004114539 |
| ENSG00000269018 | AP001362 | 1.12 | 0.88 | 0.98 | 0.93 | 0.004126107 |
| ENSG00000177425 | PAWR | 0.8 | 1.55 | 1.49 | 1.52 | 0.004267517 |
| ENSG00000207585 | MIR181D | 0.97 | 0.88 | 1.18 | 2.14 | 0.004293059 |
| ENSG00000139514 | SLC7A1 | 1.12 | 1.23 | 1.51 | 1.4 | 0.004341246 |
| ENSG00000072134 | EPN2 | 0.95 | 1.28 | 1.16 | 1.29 | 0.004347329 |
| ENSG00000186469 | GNG2 | 0.95 | 1.04 | 1.15 | 1.12 | 0.004518505 |
| ENSG00000261087 | KB-1460A1 | 0.97 | 1.29 | 1.11 | 1.36 | 0.004556475 |
| ENSG00000128833 | MYO5C | 0.69 | 1.41 | 1.5 | 1.36 | 0.004857374 |
| ENSG00000140743 | CDR2 | 1.02 | 1.25 | 1.33 | 1.43 | 0.004860557 |
| ENSG00000214797 | RP11-1036E20 | 0.73 | 1.78 | 0.91 | 1.83 | 0.004897444 |
| ENSG00000130950 | NUTM2F | 1.18 | 0.99 | 2.26 | 0.78 | 0.004936165 |
| ENSG00000143554 | SLC27A3 | 1.19 | 0.95 | 1 | 1.02 | 0.004956338 |
| ENSG00000178055 | PRSS42 | 1.76 | 0.99 | 0.78 | 1.93 | 0.005050187 |
| ENSG00000088035 | ALG6 | 0.98 | 1.23 | 1.11 | 1.21 | 0.005140574 |
| ENSG00000163751 | CPA3 | 0.8 | 0.89 | 1.24 | 1.72 | 0.005162833 |

TABLE 16-continued

| GeneID | HUGO_geneid | Ave FCPIc | Ave FC22.5 mg | Ave FC75 mg | Ave FC225 mg | PValueTrt |
|---|---|---|---|---|---|---|
| ENSG00000069188 | SDK2 | 0.96 | 1.72 | 1.25 | 1.42 | 0.005304357 |
| ENSG00000107771 | CCSER2 | 0.99 | 1.15 | 1.18 | 1.33 | 0.005436005 |
| ENSG00000153902 | LGI4 | 1.26 | 0.59 | 1.48 | 1.77 | 0.005443687 |
| ENSG00000258096 | RP11-474P2 | 0.97 | 0.55 | 0.63 | 1.1 | 0.00548777 |
| ENSG00000204632 | HLA-G | 1.09 | 0.86 | 0.96 | 0.95 | 0.005641668 |
| ENSG00000265263 | RP11-135L13 | 0.92 | 1.29 | 1.18 | 1.27 | 0.00567792 |
| ENSG00000104472 | CHRAC1 | 1 | 1.1 | 1.03 | 1.18 | 0.005716345 |
| ENSG00000185339 | TCN2 | 1.25 | 0.81 | 0.98 | 0.94 | 0.005884412 |
| ENSG00000163082 | SGPP2 | 0.71 | 1.29 | 1.09 | 1.43 | 0.005962901 |
| ENSG00000249459 | ZNF286B | 0.86 | 1.45 | 1.5 | 1.7 | 0.006009146 |
| ENSG00000104918 | RETN | 1.15 | 0.74 | 0.84 | 0.68 | 0.006052469 |
| ENSG00000259363 | CTD-2054N24 | 0.9 | 1.96 | 1.02 | 1.56 | 0.006136195 |
| ENSG00000115998 | C2orf42 | 1.01 | 1.13 | 1.07 | 1.23 | 0.006174157 |
| ENSG00000227042 | RP6-1O2 | 1.19 | 0.77 | 2.13 | 1.09 | 0.006216609 |
| ENSG00000268205 | CTC-444N24 | 1.02 | 1.16 | 1.32 | 1.32 | 0.006365583 |
| ENSG00000270674 | RP11-216F19 | 0.75 | 1.35 | 1.34 | 1.4 | 0.006366766 |
| ENSG00000130489 | SCO2 | 1.19 | 0.86 | 0.91 | 0.96 | 0.006414512 |
| ENSG00000143457 | GOLPH3L | 0.97 | 1.21 | 1.09 | 1.2 | 0.006589479 |
| ENSG00000184307 | ZDHHC23 | 0.85 | 1.37 | 1.12 | 1.41 | 0.0065945 |
| ENSG00000251606 | CTD-2215E18 | 0.82 | 1.58 | 1.37 | 1.52 | 0.006612818 |
| ENSG00000225407 | CTD-2384B11 | 0.99 | 0.66 | 1.48 | 1.66 | 0.006715329 |
| ENSG00000164543 | STK17A | 0.94 | 1.06 | 1.1 | 1.1 | 0.006754285 |
| ENSG00000213853 | EMP2 | 1.81 | 1.15 | 0.56 | 0.89 | 0.006767302 |
| ENSG00000145687 | SSBP2 | 1.04 | 1.16 | 0.98 | 1.26 | 0.00694826 |
| ENSG00000052126 | PLEKHA5 | 0.93 | 1.2 | 1.41 | 1.34 | 0.007069869 |
| ENSG00000182511 | FES | 1.03 | 0.9 | 0.92 | 0.85 | 0.007179669 |
| ENSG00000154479 | CCDC173 | 1.84 | 0.9 | 2.97 | 1.57 | 0.007230053 |
| ENSG00000155093 | PTPRN2 | 0.82 | 1.1 | 0.9 | 0.92 | 0.007338188 |
| ENSG00000149308 | NPAT | 1.02 | 1.29 | 1.27 | 1.42 | 0.007393232 |
| ENSG00000162129 | CLPB | 1.2 | 1.02 | 1.14 | 1 | 0.00742556 |
| ENSG00000133639 | BTG1 | 0.96 | 1.1 | 0.99 | 1.12 | 0.007454085 |
| ENSG00000137502 | RAB30 | 1.01 | 1.22 | 1.29 | 1.51 | 0.007471691 |
| ENSG00000271783 | RP11-533E19 | 1.07 | 0.91 | 0.89 | 0.95 | 0.00751623 |
| ENSG00000230928 | RP11-34A14 | 0.69 | 0.66 | 0.84 | 1.7 | 0.007516599 |
| ENSG00000105472 | CLEC11A | 1.25 | 0.8 | 1.07 | 1.06 | 0.007564351 |
| ENSG00000154511 | FAM69A | 1.01 | 1.25 | 1.17 | 1.44 | 0.007640476 |
| ENSG00000196323 | ZBTB44 | 1.01 | 1.04 | 1.21 | 1.14 | 0.007807758 |
| ENSG00000211880 | TRAJ9 | 0.85 | 1.43 | 1.27 | 1.57 | 0.008095052 |
| ENSG00000214105 | CTD-2116F7 | 0.82 | 0.81 | 0.81 | 2.09 | 0.0081448 |
| ENSG00000179348 | GATA2 | 0.87 | 0.98 | 1.29 | 1.75 | 0.008166472 |
| ENSG00000242611 | AC093627 | 1.58 | 0.49 | 0.72 | 1.18 | 0.008176059 |
| ENSG00000231748 | RP11-227H15 | 0.82 | 1.62 | 0.97 | 1.75 | 0.008202576 |
| ENSG00000202314 | SNORD6 | 0.69 | 1.14 | 0.97 | 1.58 | 0.008220147 |
| ENSG00000151136 | BTBD11 | 1.02 | 1.17 | 1.29 | 1.3 | 0.008257908 |
| ENSG00000242444 | RP11-320N7 | 1.35 | 0.65 | 1.25 | 0.73 | 0.008328594 |
| ENSG00000176928 | GCNT4 | 0.73 | 1.47 | 1.41 | 1.83 | 0.008453853 |
| ENSG00000252071 | snoU13 | 1.17 | 0.9 | 2.53 | 1.68 | 0.008528728 |
| ENSG00000110719 | TCIRG1 | 1.05 | 0.91 | 0.97 | 0.9 | 0.008571047 |
| ENSG00000254287 | RP11-44K6 | 1.21 | 1.52 | 0.62 | 2.01 | 0.008794321 |
| ENSG00000180771 | SRSF8 | 1.04 | 1.15 | 1.29 | 1.34 | 0.008816577 |
| ENSG00000085788 | DDHD2 | 1.02 | 1.22 | 1.31 | 1.43 | 0.008825236 |
| ENSG00000073146 | MOV10L1 | 1.75 | 0.69 | 1.05 | 0.68 | 0.00893606 |
| ENSG00000170989 | S1PR1 | 0.99 | 1.22 | 1.3 | 1.45 | 0.009048333 |
| ENSG00000198919 | DZIP3 | 1.11 | 1.41 | 1.36 | 1.58 | 0.009078348 |
| ENSG00000148468 | FAM171A1 | 0.97 | 1.43 | 1.34 | 1.5 | 0.009100937 |
| ENSG00000268950 | AC114494 | 1.15 | 1.04 | 1.03 | 0.62 | 0.009334148 |
| ENSG00000181029 | TRAPPC5 | 1.07 | 0.72 | 1.01 | 0.77 | 0.009362384 |
| ENSG00000253773 | KB-1047C11 | 1.48 | 0.53 | 1.47 | 1.22 | 0.009369507 |
| ENSG00000132388 | UBE2G1 | 0.99 | 1.06 | 1.07 | 1.13 | 0.00937239 |
| ENSG00000247796 | CTD-2366F13 | 0.71 | 1.61 | 1.33 | 1.38 | 0.009405218 |
| ENSG00000125826 | RBCK1 | 1.03 | 0.91 | 0.92 | 0.91 | 0.009480962 |
| ENSG00000133816 | MICAL2 | 0.94 | 1.07 | 1.24 | 0.99 | 0.009674292 |
| ENSG00000112782 | CLIC5 | 0.87 | 1.82 | 1.44 | 1.39 | 0.009736685 |
| ENSG00000211788 | TRAV13-1 | 0.97 | 1.13 | 1.32 | 1.47 | 0.009896104 |
| ENSG00000142910 | TINAGL1 | 1.14 | 0.62 | 0.6 | 1.5 | 0.009900654 |
| ENSG00000114120 | SLC25A36 | 1.02 | 1.28 | 1.25 | 1.45 | 0.009933956 |
| ENSG00000169228 | RAB24 | 1.04 | 0.87 | 0.87 | 0.88 | 0.009950867 |
| ENSG00000237505 | RP11-76N22 | 1 | 0.75 | 1.8 | 0.54 | 0.009970281 |
| ENSG00000132704 | FCRL2 | 0.87 | 1.34 | 1.21 | 1.26 | 0.009982893 |
| ENSG00000260093 | RP11-1E4 | 1.55 | 1.15 | 0.85 | 0.71 | 0.009990035 |
| ENSG00000030582 | CRN | 1.1 | 0.85 | 0.97 | 0.9 | 0.0099985 |
| ENSG00000238121 | LINC00426 | 0.96 | 1.25 | 1.2 | 1.4 | 0.010001848 |
| ENSG00000105270 | CLIP3 | 0.69 | 1.43 | 1.34 | 1.13 | 0.010011938 |
| ENSG00000198954 | KIAA1279 | 1.04 | 1.23 | 1.2 | 1.36 | 0.010042834 |
| ENSG00000235488 | JARID2-AS1 | 1.06 | 1.45 | 1.76 | 0.85 | 0.010088905 |
| ENSG00000158079 | PTPDC1 | 0.83 | 1.61 | 1.15 | 1.43 | 0.010189169 |
| ENSG00000198963 | RORB | 1.65 | 0.65 | 1.04 | 2.09 | 0.010227448 |

TABLE 16-continued

| GeneID | HUGO_geneid | Ave FCPIc | Ave FC22.5 mg | Ave FC75 mg | Ave FC225 mg | PValueTrt |
|---|---|---|---|---|---|---|
| ENSG00000030419 | IKZF2 | 1.05 | 1.25 | 1.34 | 1.7 | 0.010258183 |
| ENSG00000068354 | TBC1D25 | 0.96 | 1.04 | 1.11 | 1.01 | 0.010284888 |
| ENSG00000211797 | TRAV17 | 1.02 | 1.08 | 1.27 | 1.49 | 0.01029392 |
| ENSG00000197111 | PCBP2 | 0.97 | 1.03 | 1.09 | 1.03 | 0.01029625 |
| ENSG00000112182 | BACH2 | 1 | 1.28 | 1.27 | 1.56 | 0.010410668 |
| ENSG00000006432 | MAP3K9 | 0.77 | 1.4 | 1.36 | 1.41 | 0.010424898 |
| ENSG00000203364 | RP11-370F5 | 0.85 | 0.77 | 1.25 | 1.61 | 0.010456719 |
| ENSG00000233225 | AC004987 | 1 | 1 | 1.59 | 0.99 | 0.010486902 |
| ENSG00000100979 | PLTP | 1.18 | 0.97 | 0.95 | 0.95 | 0.010538665 |
| ENSG00000012983 | MAP4K5 | 1.07 | 1.17 | 1.34 | 1.37 | 0.010567962 |
| ENSG00000125868 | DSTN | 1 | 1.1 | 1.12 | 1.23 | 0.010582106 |
| ENSG00000205502 | C2CD4B | 0.66 | 1.05 | 0.85 | 0.32 | 0.010612365 |
| ENSG00000269290 | RP11-869B15 | 0.91 | 1.36 | 1.13 | 1.25 | 0.010657968 |
| ENSG00000134709 | HOOK1 | 0.98 | 1.4 | 1.54 | 1.63 | 0.010785391 |
| ENSG00000158715 | SLC45A3 | 0.91 | 1.12 | 1.2 | 1.53 | 0.010938046 |
| ENSG00000239305 | RNF103 | 0.97 | 1.15 | 1.08 | 1.16 | 0.011105681 |
| ENSG00000006210 | CX3CL1 | 1.49 | 0.78 | 0.78 | 0.76 | 0.011150528 |
| ENSG00000155016 | CYP2U1 | 0.99 | 1.33 | 1.16 | 1.38 | 0.011171069 |
| ENSG00000153064 | BANK1 | 1.06 | 1.41 | 1.31 | 1.51 | 0.01121044 |
| ENSG00000173208 | ABCD2 | 0.98 | 1.29 | 1.43 | 1.61 | 0.011362037 |
| ENSG00000235652 | RP11-545I5 | 1.01 | 1.3 | 1.26 | 1.45 | 0.011369509 |
| ENSG00000155719 | OTOA | 1.17 | 0.55 | 1.65 | 1.11 | 0.011426115 |
| ENSG00000172575 | RASGRP1 | 1.03 | 1.33 | 1.38 | 1.53 | 0.0114595 |
| ENSG00000101134 | DOK5 | 0.77 | 1.69 | 1.45 | 0.84 | 0.01146101 |
| ENSG00000169762 | TAPT1 | 0.97 | 1.15 | 1.1 | 1.2 | 0.011533654 |
| ENSG00000025800 | KPNA6 | 0.99 | 1.07 | 1.11 | 1.13 | 0.011638238 |
| ENSG00000164466 | SFXN1 | 0.93 | 1.16 | 1.13 | 1.28 | 0.011641835 |
| ENSG00000166707 | ZCCHC18 | 0.66 | 1.74 | 0.93 | 1.31 | 0.011648599 |
| ENSG00000156515 | HK1 | 1.06 | 0.99 | 1.18 | 1.01 | 0.011657858 |
| ENSG00000136504 | KAT7 | 1.02 | 1.08 | 1.1 | 1.18 | 0.011689978 |
| ENSG00000140009 | ESR2 | 0.92 | 1.22 | 1.11 | 1.28 | 0.011693601 |
| ENSG00000232274 | RP11-782C8 | 0.89 | 2.84 | 0.97 | 1.04 | 0.011738618 |
| ENSG00000268313 | AC119673 | 1.1 | 1.15 | 1.3 | 1.39 | 0.011855655 |
| ENSG00000082014 | SMARCD3 | 1.02 | 0.82 | 0.87 | 0.78 | 0.0120148 |
| ENSG00000203401 | AC009061 | 0.91 | 1.38 | 0.43 | 0.66 | 0.012041957 |
| ENSG00000174469 | CNTNAP2 | 0.69 | 1.23 | 1.59 | 1.48 | 0.012122994 |
| ENSG00000171298 | GAA | 1.1 | 0.92 | 1.08 | 0.94 | 0.012274983 |
| ENSG00000168646 | AXIN2 | 0.97 | 1.37 | 1.38 | 1.47 | 0.012358987 |
| ENSG00000119414 | PPP6C | 0.99 | 1.02 | 1.04 | 1.08 | 0.012395358 |
| ENSG00000173918 | C1QTNF1 | 0.49 | 0.82 | 0.92 | 1.47 | 0.012444802 |
| ENSG00000106537 | TSPAN13 | 0.95 | 1.29 | 1.09 | 1.32 | 0.012574375 |
| ENSG00000086189 | DIMT1 | 1.01 | 1.18 | 1.17 | 1.33 | 0.012589631 |
| ENSG00000171914 | TLN2 | 1.21 | 1.03 | 1.47 | 0.86 | 0.012608958 |
| ENSG00000079691 | LRRC16A | 1.02 | 1.38 | 1.27 | 1.4 | 0.012651996 |
| ENSG00000104660 | LEPROTL1 | 0.99 | 1.15 | 1.06 | 1.22 | 0.012660081 |
| ENSG00000134954 | ETS1 | 1.09 | 1.22 | 1.36 | 1.61 | 0.012713575 |
| ENSG00000250548 | RP11-47I22 | 1.38 | 1.1 | 0.84 | 1.02 | 0.012727916 |
| ENSG00000076984 | MAP2K7 | 1 | 1.03 | 1.11 | 1.01 | 0.012759171 |
| ENSG00000188818 | ZDHHC11 | 1.09 | 1.32 | 0.69 | 1.24 | 0.012770316 |
| ENSG00000129270 | MMP28 | 0.7 | 1.44 | 1 | 1.67 | 0.012863978 |
| ENSG00000100065 | CARD10 | 0.8 | 1.72 | 1.36 | 2.44 | 0.012893298 |
| ENSG00000158195 | WASF2 | 0.98 | 1.03 | 1.1 | 1.01 | 0.012909471 |
| ENSG00000233125 | ACTBP12 | 0.81 | 1.61 | 0.99 | 1.67 | 0.013056053 |
| ENSG00000119508 | NR4A3 | 0.76 | 0.65 | 1.1 | 1.93 | 0.013057846 |
| ENSG00000186591 | UBE2H | 0.94 | 1.01 | 1.08 | 1.01 | 0.013131542 |
| ENSG00000200227 | RNA5SP197 | 1.11 | 0.51 | 1.24 | 1.25 | 0.013222414 |
| ENSG00000103343 | ZNF174 | 1.01 | 1.08 | 1.05 | 1.18 | 0.013301434 |
| ENSG00000259728 | LINC00933 | 1.61 | 0.55 | 1.61 | 1.34 | 0.013323112 |
| ENSG00000122741 | DCAF10 | 0.94 | 1 | 1.1 | 1.06 | 0.013326578 |
| ENSG00000185736 | ADARB2 | 0.48 | 1.38 | 1.5 | 0.92 | 0.013331051 |
| ENSG00000113263 | ITK | 1.02 | 1.27 | 1.29 | 1.51 | 0.013341612 |

The invention claimed is:

1. A method for treating ulcerative colitis in a patient comprising administering subcutaneously to the patient an initial dose of 22.5 mg of MAdCAM antagonist antibody comprising light chain SEQ ID NO: 1 and heavy chain SEQ ID NO: 2 once every 4 weeks for at least 12 weeks to achieve a clinical remission rate of at least 10% compared to baseline, wherein the clinical remission rate is determined using a MAYO score or a sccai score.

2. The method of claim 1, comprising administering to the patient one or more subsequent doses of 22.5 mg or 75 mg of MAdCAM antagonist antibody.

3. The method of claim 2, wherein a subsequent dose is administered between about 1 week and about 12 weeks after the initial dose.

4. The method of claim 3, wherein the subsequent dose is administered about 4 weeks after the initial dose.

5. The method of claim 1, wherein the patient is not taking a TNF antagonist or TNF inhibitor.

6. The method of claim 1, wherein the clinical remission rate is determined using the MAYO score.

7. The method of claim 1, wherein the clinical remission rate is determined using the sccai score.

8. A method for treating ulcerative colitis in a patient comprising administering subcutaneously to the patient a dose of 22.5 mg of MAdCAM antagonist antibody comprising a light chain CDR1 of SEQ ID NO:11; a light chain CDR2 of SEQ ID NO:12; and a light chain CDR3 of SEQ ID NO:13; and a heavy chain CDR1 of SEQ ID NO:14; a heavy chain CDR2 of SEQ ID NO:15; and a heavy chain CDR3 of SEQ ID NO:16, once every 4 weeks for at least 12 weeks to achieve a clinical remission rate of at least about 10% compared to baseline, wherein the clinical remission rate is determined using a MAYO score or a sccai score.

9. The method of claim 8, wherein the clinical remission rate is determined using a MAYO score.

10. The method of claim 8, wherein the clinical remission rate is determined using a sccai score.

* * * * *

UNITED STATES PATENT AND TRADEMARK OFFICE
CERTIFICATE OF CORRECTION

| | | |
|---|---|---|
| PATENT NO. | : 11,884,726 B2 | Page 1 of 1 |
| APPLICATION NO. | : 17/107228 | |
| DATED | : January 30, 2024 | |
| INVENTOR(S) | : Cataldi et al. | |

It is certified that error appears in the above-identified patent and that said Letters Patent is hereby corrected as shown below:

In the Claims

In Claim 3, Column 118, Line 61:
Delete "wherein a subsequent …"
Replace with -- wherein the subsequent … --

Signed and Sealed this
Twenty-second Day of April, 2025

Coke Morgan Stewart
*Acting Director of the United States Patent and Trademark Office*

SEQUENCE LISTING

<160> NUMBER OF SEQ ID NOS: 38

<210> SEQ ID NO 1
<211> LENGTH: 219
<212> TYPE: PRT
<213> ORGANISM: Artificial Sequence
<220> FEATURE:
<223> OTHER INFORMATION: Synthetic Construct

<400> SEQUENCE: 1

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Thr
            20                  25                  30

Asp Gly Thr Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Asn
                85                  90                  95

Ile Gln Leu Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 2
<211> LENGTH: 450
<212> TYPE: PRT
<213> ORGANISM: Artificial Sequence
<220> FEATURE:
<223> OTHER INFORMATION: Synthetic Construct

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Asn Trp Val Arg Gln Ala Pro Gly Gln Gly Leu Glu Trp Met
        35                  40                  45

Gly Trp Ile Ser Val Tyr Ser Gly Asn Thr Asn Tyr Ala Gln Lys Val
    50                  55                  60

Gln Gly Arg Val Thr Met Thr Ala Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Glu Gly Ser Ser Ser Gly Asp Tyr Tyr Tyr Gly Met Asp
            100                 105                 110

Val Trp Gly Gln Gly Thr Thr Val Thr Val Ser Ser Ala Ser Thr Lys
        115                 120                 125

```
Gly Pro Ser Val Phe Pro Leu Ala Pro Cys Ser Arg Ser Thr Ser Glu
            130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 3
<211> LENGTH: 112
<212> TYPE: PRT
<213> ORGANISM: Artificial Sequence
<220> FEATURE:
<223> OTHER INFORMATION: Synthetic Construct

<400> SEQUENCE: 3

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Thr
            20                  25                  30
```

Asp Gly Thr Thr Tyr Leu Tyr Trp Tyr Leu Gln Lys Pro Gly Gln Pro
            35                  40                  45

Pro Gln Leu Leu Ile Tyr Glu Val Ser Asn Arg Phe Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Asn
                 85                  90                  95

Ile Gln Leu Pro Trp Thr Phe Gly Gln Gly Thr Lys Val Glu Ile Lys
            100                 105                 110

<210> SEQ ID NO 4
<211> LENGTH: 124
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Gly Ile Asn Trp Val Arg Gln Ala Pro Gly Gln Gly Leu Glu Trp Met
         35                  40                  45

Gly Trp Ile Ser Val Tyr Ser Gly Asn Thr Asn Tyr Ala Gln Lys Val
     50                  55                  60

Gln Gly Arg Val Thr Met Thr Thr Ala Asp Thr Ser Thr Ser Thr Ala Tyr
 65                  70                  75                  80

Met Asp Leu Arg Ser Leu Arg Ser Asp Asp Thr Ala Val Tyr Tyr Cys
                 85                  90                  95

Ala Arg Glu Gly Ser Ser Ser Gly Asp Tyr Tyr Tyr Gly Met Asp
            100                 105                 110

Val Trp Gly Gln Gly Thr Thr Val Thr Val Ser Ser
            115                 120

<210> SEQ ID NO 5
<211> LENGTH: 107
<212> TYPE: PRT
<213> ORGANISM: Artificial Sequence
<220> FEATURE:
<223> OTHER INFORMATION: Synthetic Construct

<400> SEQUENCE: 5

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

-continued

```
<210> SEQ ID NO 6
<211> LENGTH: 101
<212> TYPE: PRT
<213> ORGANISM: Artificial Sequence
<220> FEATURE:
<223> OTHER INFORMATION: Synthetic Construct

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys
            100

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Cys Cys Val Glu Cys Pro Pro Cys Pro
1               5

<210> SEQ ID NO 8
<211> LENGTH: 109
<212> TYPE: PRT
<213> ORGANISM: Artificial Sequence
<220> FEATURE:
<223> OTHER INFORMATION: Synthetic Construct

<400> SEQUENCE: 8

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105

<210> SEQ ID NO 9
<211> LENGTH: 107
```

```
<212> TYPE: PRT
<213> ORGANISM: Artificial Sequence
<220> FEATURE:
<223> OTHER INFORMATION: Synthetic Construct

<400> SEQUENCE: 9

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 10
<211> LENGTH: 326
<212> TYPE: PRT
<213> ORGANISM: Artificial Sequence
<220> FEATURE:
<223> OTHER INFORMATION: Synthetic Construct

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 11
<211> LENGTH: 16
<212> TYPE: PRT
<213> ORGANISM: Artificial Sequence
<220> FEATURE:
<223> OTHER INFORMATION: Synthetic Construct

<400> SEQUENCE: 11

Lys Ser Ser Gln Ser Leu Leu His Thr Asp Gly Thr Thr Tyr Leu Tyr
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

Glu Val Ser Asn Arg Phe Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Met Gln Asn Ile Gln Leu Pro Trp Thr
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Ser Tyr Gly Ile Asn
1               5

<210> SEQ ID NO 15
<211> LENGTH: 17
<212> TYPE: PRT
<213> ORGANISM: Artificial Sequence
```

```
<220> FEATURE:
<223> OTHER INFORMATION: Synthetic Construct

<400> SEQUENCE: 15

Trp Ile Ser Val Tyr Ser Gly Asn Thr Asn Tyr Ala Gln Lys Val Gln
1               5                   10                  15
Gly

<210> SEQ ID NO 16
<211> LENGTH: 15
<212> TYPE: PRT
<213> ORGANISM: Artificial Sequence
<220> FEATURE:
<223> OTHER INFORMATION: Synthetic Construct

<400> SEQUENCE: 16

Glu Gly Ser Ser Ser Gly Asp Tyr Tyr Gly Met Asp Val
1               5                   10                  15

<210> SEQ ID NO 17
<211> LENGTH: 218
<212> TYPE: PRT
<213> ORGANISM: Artificial Sequence
<220> FEATURE:
<223> OTHER INFORMATION: Synthetic Construct

<400> SEQUENCE: 17

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Gln Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Ile Thr Phe Gly Gln Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 18
<211> LENGTH: 444
<212> TYPE: PRT
```

<213> ORGANISM: Artificial Sequence
<220> FEATURE:
<223> OTHER INFORMATION: Synthetic Construct

<400> SEQUENCE: 18

```
Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Thr Asn Ala
            20                  25                  30

Trp Met Ile Trp Val Arg Gln Ala Pro Gly Lys Gly Leu Glu Trp Val
        35                  40                  45

Gly Arg Ile Lys Arg Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Gly Val Ala Glu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
```

```
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
                420                 425                 430
Tyr Thr Gln Lys Ser Leu Ser Leu Ser Pro Gly Lys
                435                 440

<210> SEQ ID NO 19
<211> LENGTH: 218
<212> TYPE: PRT
<213> ORGANISM: Artificial Sequence
<220> FEATURE:
<223> OTHER INFORMATION: Synthetic Construct

<400> SEQUENCE: 19

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu Gln Ser
                20                  25                  30
Asn Gly Phe Asn Tyr Leu Asp Trp Tyr Leu Gln Lys Pro Gly Gln Ser
            35                  40                  45
Pro Gln Leu Leu Ile Tyr Leu Gly Ser Asn Arg Ala Ser Gly Val Pro
        50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Leu Gln Thr Ile Thr Phe Gly Gln Gly Thr Arg Leu Glu Ile Lys Arg
                100                 105                 110
Thr Val Ala Ala Pro Ser Val Phe Ile Phe Pro Pro Ser Asp Glu Gln
            115                 120                 125
Leu Lys Ser Gly Thr Ala Ser Val Val Cys Leu Leu Asn Asn Phe Tyr
        130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
                180                 185                 190
His Lys Val Tyr Ala Cys Glu Val Thr His Gln Gly Leu Ser Ser Pro
            195                 200                 205
Val Thr Lys Ser Phe Asn Arg Gly Glu Cys
        210                 215

<210> SEQ ID NO 20
<211> LENGTH: 444
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Lys Pro Gly Gly
1               5                   10                  15
Ser Leu Arg Leu Ser Cys Val Val Ser Gly Phe Thr Phe Thr Asn Ala
                20                  25                  30
```

-continued

Trp Met Ile Trp Val Arg Gln Ala Pro Gly Lys Gly Leu Glu Trp Val
         35                  40                  45

Gly Arg Ile Lys Arg Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Gly Gly Val Ala Glu Asp Tyr Trp Gly Gln Gly Thr
             100                 105                 110

Leu Val Thr Val Ser Ser Ala Ser Thr Lys Gly Pro Ser Val Phe Pro
         115                 120                 125

Leu Ala Pro Cys Ser Arg Ser Thr Ser Glu Ser Thr Ala Ala Leu Gly
 130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                 165                 170                 175

Ser Ser Gly Leu Tyr Ser Leu Ser Ser Val Val Thr Val Pro Ser Ser
             180                 185                 190

Asn Phe Gly Thr Gln Thr Tyr Thr Cys Asn Val Asp His Lys Pro Ser
         195                 200                 205

Asn Thr Lys Val Asp Lys Thr Val Glu Arg Lys Cys Cys Val Glu Cys
 210                 215                 220

Pro Pro Cys Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
                 245                 250                 255

Thr Cys Val Val Val Asp Val Ser His Glu Asp Pro Glu Val Gln Phe
             260                 265                 270

Asn Trp Tyr Val Asp Gly Val Glu Val His Asn Ala Lys Thr Lys Pro
         275                 280                 285

Arg Glu Glu Gln Phe Asn Ser Thr Phe Arg Val Val Ser Val Leu Thr
 290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                 325                 330                 335

Lys Gly Gln Pro Arg Glu Pro Gln Val Tyr Thr Leu Pro Pro Ser Arg
             340                 345                 350

Glu Glu Met Thr Lys Asn Gln Val Ser Leu Thr Cys Leu Val Lys Gly
         355                 360                 365

Phe Tyr Pro Ser Asp Ile Ala Val Glu Trp Glu Ser Asn Gly Gln Pro
 370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                 405                 410                 415

Gly Asn Val Phe Ser Cys Ser Val Met His Glu Ala Leu His Asn His
             420                 425                 430

Tyr Thr Gln Lys Ser Leu Ser Leu Ser Pro Gly Lys
         435                 440

-continued

```
<210> SEQ ID NO 21
<211> LENGTH: 214
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Ser Ile Ser Ser Tyr
            20                  25                  30

Leu Asn Trp Tyr Gln Gln Lys Pro Gly Lys Ala Pro Lys Val Leu Ile
        35                  40                  45

Phe Phe Val Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ile Pro Pro Ile
                85                  90                  95

Thr Phe Gly Gln Gly Thr Arg Leu Glu Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 448
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Asn Asn Ser
            20                  25                  30

Ala Met Thr Trp Val Arg Gln Ala Pro Gly Lys Gly Leu Glu Trp Val
        35                  40                  45

Ser Thr Thr Ser Gly Ser Gly Gly Thr Thr Tyr Tyr Ala Asp Ser Val
    50                  55                  60

Lys Gly Arg Phe Thr Ile Ser Arg Asp Ser Pro Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Ala Arg Gly Tyr Ser Tyr Gly Thr Thr Pro Tyr Glu Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Ser Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 23
<211> LENGTH: 214
<212> TYPE: PRT
<213> ORGANISM: Artificial Sequence
<220> FEATURE:
<223> OTHER INFORMATION: Synthetic Construct

<400> SEQUENCE: 23

Glu Ile Val Leu Thr Gln Ser Pro Asp Phe Gln Ser Val Thr Pro Lys
1               5                   10                  15
```

```
Glu Lys Val Thr Ile Thr Cys Arg Ala Ser Gln Arg Ile Gly Ser Ser
             20                  25                  30

Leu His Trp Tyr Gln Gln Lys Pro Asp Gln Ser Pro Lys Leu Leu Ile
         35                  40                  45

Lys Tyr Ala Ser Gln Ser Phe Ser Gly Val Pro Ser Arg Phe Ser Gly
     50                  55                  60

Ser Gly Ser Gly Thr Asn Phe Thr Leu Thr Ile Asn Gly Leu Glu Ala
65                  70                  75                  80

Glu Asp Ala Ala Thr Tyr Tyr Cys His Gln Ser Gly Arg Leu Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 446
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Val Glu Ser Gly Gly Gly Val Val Gln Pro Gly Arg
1               5                   10                  15

Ser Leu Arg Leu Ser Cys Ala Ala Ser Gly His Thr Phe Ser Ser Asp
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Tyr Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Lys Thr Tyr Thr Cys Asn Val Asp His Lys Pro
    195                 200                 205

Ser Asn Thr Lys Val Asp Lys Arg Val Glu Ser Lys Tyr Gly Pro Pro
210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Ala Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 25
<211> LENGTH: 214
<212> TYPE: PRT
<213> ORGANISM: Artificial Sequence
<220> FEATURE:
<223> OTHER INFORMATION: Synthetic Construct

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Ser Tyr
            20                  25                  30

Leu Asn Trp Phe Gln Gln Lys Pro Gly Lys Ala Pro Lys Leu Leu Ile
        35                  40                  45

Tyr Ala Ala Ser Gly Leu Lys Arg Gly Val Pro Ser Arg Phe Ser Gly
    50                  55                  60

Ser Gly Ser Gly Thr Asp Phe Thr Leu Thr Ile Arg Thr Leu Gln Pro
65                  70                  75                  80
```

Asp Asp Phe Ala Thr Tyr Ser Cys His Gln Ser Tyr Ser Leu Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 450
<212> TYPE: PRT
<213> ORGANISM: Artificial Sequence
<220> FEATURE:
<223> OTHER INFORMATION: Synthetic Construct

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Asn Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Val Tyr Tyr Cys
                85                  90                  95

Ala Arg Asp Ser Thr Ala Ile Thr Tyr Tyr Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

```
Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
    435                 440                 445

Gly Lys
450

<210> SEQ ID NO 27
<211> LENGTH: 221
<212> TYPE: PRT
<213> ORGANISM: Artificial Sequence
<220> FEATURE:
<223> OTHER INFORMATION: Synthetic Construct

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Thr Tyr Leu Ala Trp Tyr Gln Gln Lys Pro Arg Gln
        35                  40                  45

Pro Pro Lys Leu Leu Ile Tyr Trp Ala Ser Ile Arg Glu Tyr Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
            85                  90                  95

Tyr Tyr Ser Ile Pro Pro Leu Thr Phe Gly Gly Gly Thr Lys Val Glu
        100                 105                 110

Ile Lys Arg Thr Val Ala Ala Pro Ser Val Phe Ile Phe Pro Pro Ser
    115                 120                 125
```

Asp Glu Gln Leu Lys Ser Gly Thr Ala Ser Val Val Cys Leu Leu Asn
130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
                180                 185                 190

Tyr Glu Lys His Lys Val Tyr Ala Cys Glu Val Thr His Gln Gly Leu
                195                 200                 205

Ser Ser Pro Val Thr Lys Ser Phe Asn Arg Gly Glu Cys
210                 215                 220

<210> SEQ ID NO 28
<211> LENGTH: 451
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Asn
                20                  25                  30

Tyr Trp Ser Trp Ile Arg Gln Pro Ala Gly Lys Gly Leu Glu Trp Ile
            35                  40                  45

Gly Arg Ile Tyr Thr Ser Gly Gly Thr Asn Ser Asn Pro Ser Leu Arg
50                  55                  60

Gly Arg Val Thr Ile Leu Ala Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Arg Ile Thr Ile Ile Arg Gly Leu Ile Pro Ser Phe Phe Asp
                100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Lys Thr Tyr Thr Cys Asn
                195                 200                 205

Val Asp His Lys Pro Ser Asn Thr Lys Val Asp Lys Arg Val Glu Ser
            210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

```
Glu Asp Pro Glu Val Gln Phe Asn Trp Tyr Val Asp Gly Val Glu Val
            275                 280                 285
His Asn Ala Lys Thr Lys Pro Arg Glu Gln Phe Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Gly Leu Pro Ser Ser Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Gln Glu Glu Met Thr Lys Asn Gln Val Ser
        355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Arg Leu Thr Val
                405                 410                 415
Asp Lys Ser Arg Trp Gln Glu Gly Asn Val Phe Ser Cys Ser Val Met
            420                 425                 430
His Glu Ala Leu His Asn His Tyr Thr Gln Lys Ser Leu Ser Leu Ser
        435                 440                 445
Leu Gly Lys
    450

<210> SEQ ID NO 29
<211> LENGTH: 216
<212> TYPE: PRT
<213> ORGANISM: Artificial Sequence
<220> FEATURE:
<223> OTHER INFORMATION: Synthetic Construct

<400> SEQUENCE: 29

Asp Ile Gln Met Thr Gln Ser Pro Ser Ser Leu Ser Ala Ser Val Gly
1               5                   10                  15
Asp Arg Val Thr Phe Thr Cys Arg Ala Ser Gln Asn Ile Thr Asn Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Pro Arg Gly Val Pro Ser Arg Phe Arg Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Asn Pro Pro
                85                  90                  95
Glu Cys Gly Phe Gly Gln Gly Thr Thr Leu Asp Ile Lys Arg Thr Val
            100                 105                 110
Ala Ala Pro Ser Val Phe Ile Phe Pro Pro Ser Asp Glu Gln Leu Lys
        115                 120                 125
Ser Gly Thr Ala Ser Val Val Cys Leu Leu Asn Asn Phe Tyr Pro Arg
    130                 135                 140
Glu Ala Lys Val Gln Trp Lys Val Asp Asn Ala Leu Gln Ser Gly Asn
145                 150                 155                 160
Ser Gln Glu Ser Val Thr Glu Gln Asp Ser Lys Asp Ser Thr Tyr Ser
                165                 170                 175
```

```
Leu Ser Ser Thr Leu Thr Leu Ser Lys Ala Asp Tyr Glu Lys His Lys
            180                 185                 190
Val Tyr Ala Cys Glu Val Thr His Gln Gly Leu Ser Ser Pro Val Thr
            195                 200                 205
Lys Ser Phe Asn Arg Gly Glu Cys
        210                 215

<210> SEQ ID NO 30
<211> LENGTH: 452
<212> TYPE: PRT
<213> ORGANISM: Artificial Sequence
<220> FEATURE:
<223> OTHER INFORMATION: Synthetic Construct

<400> SEQUENCE: 30

Glu Val Gln Leu Leu Glu Ser Gly Gly Asp Leu Val Gln Pro Gly Gly
1               5                   10                  15
Ser Leu Arg Leu Ser Cys Ala Ala Ser Gly Phe Thr Phe Arg Ser Tyr
            20                  25                  30
Ala Met Asn Trp Val Arg Gln Ala Pro Gly Lys Gly Leu Glu Trp Val
        35                  40                  45
Ser Val Ile Ser Gly Arg Gly Thr Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Ala Ala Val Tyr Tyr Cys
                85                  90                  95
Ala Lys Ile Ala Val Ala Gly Glu Gly Leu Tyr Tyr Tyr Gly Met
            100                 105                 110
Asp Val Trp Gly Gln Gly Thr Thr Val Thr Val Ser Ser Ala Ser Thr
        115                 120                 125
Lys Gly Pro Ser Val Phe Pro Leu Ala Pro Cys Ser Arg Ser Thr Ser
130                 135                 140
Glu Asn Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
        195                 200                 205
Asn Val Asp His Lys Pro Ser Asn Thr Lys Val Asp Lys Arg Val Glu
    210                 215                 220
Ser Lys Tyr Gly Pro Pro Cys Pro Ser Cys Pro Ala Pro Glu Phe Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Glu Asp Pro Glu Val Gln Phe Asn Trp Tyr Val Asp Gly Val Glu
        275                 280                 285
Val His Asn Ala Lys Thr Lys Pro Arg Glu Glu Gln Phe Asn Ser Thr
    290                 295                 300
Tyr Arg Val Val Ser Val Leu Thr Val Leu His Gln Asp Trp Leu Asn
305                 310                 315                 320
```

```
Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 31
<211> LENGTH: 219
<212> TYPE: PRT
<213> ORGANISM: Artificial Sequence
<220> FEATURE:
<223> OTHER INFORMATION: Synthetic Construct

<400> SEQUENCE: 31

Asp Ile Val Met Thr Gln Thr Pro Leu Ser Leu Ser Val Thr Pro Gly
1               5                   10                  15

Gln Pro Ala Ser Ile Ser Cys Asn Ser Ser Gln Ser Leu Leu Leu Ser
            20                  25                  30

Asp Gly Lys Thr Tyr Leu Asn Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Ser Cys Met Gln Ser
                85                  90                  95

Ile Gln Leu Met Cys Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 32
<211> LENGTH: 453
<212> TYPE: PRT
<213> ORGANISM: Artificial Sequence
<220> FEATURE:
<223> OTHER INFORMATION: Synthetic Construct

<400> SEQUENCE: 32

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Ser Gly Trp Ser Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Ser Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365
```

```
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Arg Ser
            420                 425                 430

Val Met His Glu Ala Leu His Asn His Tyr Thr Gln Lys Ser Leu Ser
        435                 440                 445

Leu Ser Leu Gly Lys
    450

<210> SEQ ID NO 33
<211> LENGTH: 218
<212> TYPE: PRT
<213> ORGANISM: Artificial Sequence
<220> FEATURE:
<223> OTHER INFORMATION: Synthetic Construct

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Gly
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 34
<211> LENGTH: 452
<212> TYPE: PRT
<213> ORGANISM: Artificial Sequence
<220> FEATURE:
<223> OTHER INFORMATION: Synthetic Construct

<400> SEQUENCE: 34
```

-continued

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Tyr
            20                  25                  30

His Trp Asn Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Leu Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Val Arg Tyr Tyr Ala Ser Gly Ser Tyr Tyr Tyr Gly
            100                 105                 110

Leu Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415
```

```
Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450

<210> SEQ ID NO 35
<211> LENGTH: 219
<212> TYPE: PRT
<213> ORGANISM: Artificial Sequence
<220> FEATURE:
<223> OTHER INFORMATION: Synthetic Construct

<400> SEQUENCE: 35

Asp Ile Val Met Thr Gln Thr Pro Leu Ser Leu Ser Val Thr Pro Gly
1               5                   10                  15

Gln Pro Ala Ser Ile Ser Cys Lys Ser Asn Gln Ser Leu Leu Tyr Ser
            20                  25                  30

Asp Gly Lys Thr Tyr Leu Phe Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 36
<211> LENGTH: 450
<212> TYPE: PRT
<213> ORGANISM: Artificial Sequence
<220> FEATURE:
<223> OTHER INFORMATION: Synthetic Construct

<400> SEQUENCE: 36

Gln Val Gln Leu Val Gln Ser Gly Ala Glu Val Lys Lys Pro Gly Ala
1               5                   10                  15

Ser Val Lys Val Ser Cys Glu Ala Ser Gly Tyr Thr Phe Thr Ser Tyr
            20                  25                  30

Gly Ile Asp Trp Val Arg Gln Ala Pro Gly Gln Gly Leu Glu Trp Met
        35                  40                  45
```

-continued

```
Gly Trp Ile Ser Val Tyr Ser Gly Asn Thr Asn Tyr Ala Gln Lys Leu
 50                  55                  60

Gln Gly Arg Val Thr Met Ser Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Glu Gly Ser Ser Ser Gly Asp Tyr Tyr Tyr Gly Met Asp
            100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
            195                 200                 205

Val Asp His Lys Pro Ser Asn Thr Lys Val Asp Lys Thr Val Glu Arg
210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450
```

```
<210> SEQ ID NO 37
<211> LENGTH: 214
<212> TYPE: PRT
<213> ORGANISM: Artificial Sequence
<220> FEATURE:
<223> OTHER INFORMATION: Synthetic Construct

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Ser Cys Gln His Ser Asp Asn Leu Ser Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 38
<211> LENGTH: 443
<212> TYPE: PRT
<213> ORGANISM: Artificial Sequence
<220> FEATURE:
<223> OTHER INFORMATION: Synthetic Construct

<400> SEQUENCE: 38

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Arg Gly Ala Tyr His Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Ser
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440
```